(12) United States Patent
Ajjawi et al.

(10) Patent No.: US 9,765,126 B2
(45) Date of Patent: Sep. 19, 2017

(54) COMPOSITIONS AND METHODS FOR MODULATING BIOMASS PRODUCTIVITY

(71) Applicant: Synthetic Genomics, Inc., La Jolla, CA (US)

(72) Inventors: Imad Ajjawi, La Jolla, CA (US); Moena Aqui, San Diego, CA (US); Leah Soriaga, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/506,575

(22) Filed: Oct. 3, 2014

(65) Prior Publication Data

US 2015/0191515 A1 Jul. 9, 2015

Related U.S. Application Data

(60) Provisional application No. 61/887,226, filed on Oct. 4, 2013.

(51) Int. Cl.

| *C07K 14/405* | (2006.01) |
| *C12N 1/12* | (2006.01) |
| *C12N 15/79* | (2006.01) |
| *C12N 15/82* | (2006.01) |
| *C12P 1/00* | (2006.01) |
| *C12P 7/64* | (2006.01) |
| *C12P 13/04* | (2006.01) |
| *C12P 19/00* | (2006.01) |
| *C12P 19/34* | (2006.01) |
| *C12P 21/00* | (2006.01) |

(52) U.S. Cl.
CPC .............. *C07K 14/405* (2013.01); *C12N 1/12* (2013.01); *C12N 15/79* (2013.01); *C12N 15/8261* (2013.01); *C12P 1/00* (2013.01); *C12P 7/64* (2013.01); *C12P 7/649* (2013.01); *C12P 13/04* (2013.01); *C12P 19/00* (2013.01); *C12P 19/34* (2013.01); *C12P 21/00* (2013.01); Y02E 50/13 (2013.01)

(58) Field of Classification Search
None
See application file for complete search history.

(56) References Cited

U.S. PATENT DOCUMENTS

| 6,782,035 B1 | 8/2004 | Nakamura et al. |
| 7,157,621 B2 | 1/2007 | Allen et al. |
| 7,294,759 B2 | 11/2007 | Allen et al. |
| 7,635,800 B2 | 12/2009 | Ratcliffe et al. |
| 7,868,229 B2 | 1/2011 | Ratcliffe et al. |
| 2003/0167526 A1 | 9/2003 | Lowe et al. |
| 2007/0199107 A1 | 8/2007 | Ratcliffe et al. |
| 2008/0163397 A1 | 7/2008 | Ratcliffe et al. |
| 2010/0184130 A1 | 7/2010 | Koprowski et al. |
| 2010/0319086 A1 | 12/2010 | Shen et al. |
| 2011/0099665 A1 | 4/2011 | Shen et al. |
| 2011/0138499 A1 | 6/2011 | Zhang et al. |
| 2012/0137382 A1 | 5/2012 | Repetti et al. |
| 2013/0333074 A1 | 12/2013 | Mock et al. |

FOREIGN PATENT DOCUMENTS

| WO | WO 2008/021021 A2 | 2/2008 |
| WO | WO 2011/097261 A1 | 8/2011 |
| WO | WO 2012/047970 A1 | 4/2012 |

OTHER PUBLICATIONS

International Search Report issued Mar. 19, 2015, regarding PCT/US2014/059198.
Database Geneseq [Online] "Corn HAP3 CCAAT-binding transcription factor (G3435) B domain.", Nov. 1, 2007, XP002766744, retrieved from EBI accession No. GSP:AJF57842, Database accession No. AJF57842, * sequence *.
Database JPO Proteins [Online], "JP 2011087577-A/3380:Transcription Factors.", Aug. 24, 2012, XP002766745, retrieved from EBI accession No. JPOP:DJ761664 Database accession No. DJ761664 * sequence *.
Database UniProt [Online]: "SubName: Full= Transcription factor ECO:00003131EMBL:EFN54996.1}; Flags: Fragment;", Nov. 30, 2010, XP002766743, retrieved from EBI accession No. Uniprot: E1ZGU1 Database accession No. E1ZGU1 * sequence *.
Supplementary Partial European Search Report issued on Feb. 21, 2017, regarding EP 14 85 1126.
Ballif et al.: "Over-expression of HAP3b enhances primary root elongation in Arabidopsis"; Plant Physiol and Biochem 49: 579-583, 2011.
Becker et al.: "A cDNA encoding a human CCAAT-binding protein cloned by functional complementation in yeast"; Proc. Natl. Acad. Sci. USA 88:1968-1972, 1991.
Bromberg et al.: "Snap predicts effect of mutations on protein function"; Bioinformatics 24: 2397-2398 (2008).
Calvenzani et al.: "Interactions and CCAAT-Binding of Arabidopsis thaliana NF-Y Subunits"; PLOS ONE 7: e42902, 2012.
Courchesne et al.: "Enhancement of lipid production using biochemical, genetic and transcription factor engineering approaches"; J. Biotechnol 141:31-41, 2009.
Edwards et al.: "Multiple Genes Encoding the Conserved CCAAT-Box Transcription Factor Complex Are Expressed in Arabidopsis"; Plant Physiol. 117:1015-1022, 1998.
Guo et al.: "Protein tolerance to random amino acid change"; Proc Natl Acad Sci 101: 9205-9210.

(Continued)

Primary Examiner — Marsha Tsay
(74) Attorney, Agent, or Firm — DLA Piper LLP (US)

(57) ABSTRACT

The disclosure generally relates to methods and materials for modulating cell productivity. In particular, the present disclosure provides polynucleotides encoding transcription factor proteins that when overexpressed in microorganisms result in increased in productivity, such as increased biomass productivity. Also disclosed are methods of using the genetically engineered host strains to modulate or increase productivity of host cells such as, for example, algal or heterokont cells. Genetically engineered host cells, such as algal and heterokont cells having increased biomass productivity and bioproducts derived from such host cells are also disclosed.

16 Claims, 7 Drawing Sheets

(56) References Cited

OTHER PUBLICATIONS

Gusmaroli et al.: "Regulation of novel members of the Arabidopsis thaliana CCAAT-binding nuclear factor Y subunits"; Gene 283:41-48, 2002.

Harun et al.: "Bioprocess engineering of microalgae to produce a variety of consumer products"; Renewable and Sustainable Energy Reviews 14: 1037-1047, 2010.

Kumimoto et al.: "The Nuclear Factor Y subunits NF-YB2 and NF-YB3 play additive roles in the promotion of flowering by inductive long-day photoperiods in Arabidopsis"; (2008) Planta 228:709-723.

Kwong et al.: "Leafy COTYLEDON1-Like Defines a Class of Regulators Essential for Embryo Development"; The Plant Cell 15:5-18, 2003.

Laloum et al.: "CCAAT-box binding transcription factors in plants: Y so many?"; Trends in Plant Science 18: 157-, 2012.

Lee et al.: "Arabidopsis LEAFY COTYLEDON1 represents a functionally specialized subunit of the CCAAT binding transcription factor"; Proc. Natl. Acad. Sci. 100: 2152-2156, 2003.

Li et al.: "Evolutionary variation of the CCAAT-binding transcription factor NF-Y"; Nucl Acids Res 20: 1087-1091, 1992.

Lotan et al.: "Arabidopsis LEAFY COTYLEDON1 Is Sufficient to Induce Embryo Development in Vegetative Cells"; Cell 93:1195-1205, 1998.

Mayer et al.: "Linking enzyme sequence to function using conserved property difference locator to identify and annotate positions likely to control specific functionality"; BMC Bioinformatics, Nov. 30, 2005, 6: 284. 9 pages.

Mu et al.: "LEAFY COTYLEDON1 Is a Key Regulator of Fatty Acid Biosynthesis in in Arabidopsisip$^{1[C][W][OA]}$"; Plant Physiol. 148: 1042-1054, 2008.

Nelson et al.: "Plant nuclear factor Y (NF-Y) B subunits confer drought tolerance and lead to improved corn yields on water-limited acres"; Proc. Natl. Acad. Sci 104: 16450-16455.

Ng and Henikoff: "SIFT: Predicting amino acid changes that affect protein function"; Nucl Acids Res 31: 3812-3814.

Perez-Rodriguez et al.: "Pln TFDB: updated content and new features of the plant transcription factor database"; (2010) Nucl. Acids Res. 38 (Suppl 1): D822-D827.

Petroni et al,: "The promiscuous life of plant Nuclear Factor Y transcription factors"; The Plant Cell 24: 4777-4792, 2012.

Reva et al.: "Predicting the functional impact of protein mutations: application to cancer genomics"; Nucl Acids Res 39: e118.

Shen et al.: "Expression of ZmLEC1 and ZmWRl1 increases seed oil production in maize"; Plant Physiol. 153: 980-987, 2010.

Tavtigian et al.: "In silico analysis of missense substitutions using sequence-alignment based methods"; Human Mutation 29: 1327-1336, 2008.

Weselake et al.: "Increasing the flow of carbon into seed oil"; Biotechnol Adv 27: 866-878, 2009.

Xie et al.: "Duplication and functional diversification of HAP3 genes leading to the origin of the seed-developmental regulatory gene, LEAFY COTYLEDON1 (LEC1), in nonseed plant genomes"; Mol. Biol. Evol. 25(8): 1581-1592.

```
Arabidopsis-LEC1      1  MERGAPFSHYQLPKSISELNLDQHSNNPTPMTSSVVVAGAGDKNNGIVVQQQPPCVAREQ
EMRE1EUKT264674       1  ----------------------------------------MDAAGANEGGRVGGA----GVEEVREQ
At4g14540-NF-YB3      1  ----------------------------------------MDDNDSGGHKDGGN------ASAREQ
At2g38880-NF-YB1      1  ----------------------------------------MDPSSPG--DGGE----SGGSVREQ
At5g47640-NF-YB2      1  ----------------------------------------MDDRDSGGQNGNNQNGQSSISAREQ
                                 DNA-binding              Subunit interaction
                                 ==========                ====================
Arabidopsis-LEC1     61  DQYKPIANVIRIMRKTLPSHAKISDDAKETIQECVSEFISFITGEANERCQQEQRKTIT
EMRE1EUKT264674      25  DRYLPIANVSRIMKKALPANAKIAKDAKETVQECVSEFISFITSEASDKCQQEKRKTING
At4g14540-NF-YB3     23  DRYLPIANVSRIMKKALPANAKISKDAKETVQECVSEFISFITGEASDKCQEKRKTING
At2g38880-NF-YB1     23  DRYLPIANVSRIMKKALPFNKKICKDAKTVQECVSEFISFITSEASDKCQEKRKTING
At5g47640-NF-YB2     29  DRYLPIANVSRIMKKALPANAKISKDAKETQECVSEFISFTGEASDKCQEKRKTING Arabidopsis-LEC1    121  DDLLWAMKLGFNVVPITVERYREDT SGSALRGEPPSLRQTYGGNGIGFHGPSH
EMRE1EUKT264674      85  DDLLWAMTLGFKYVEPLKHYLVLYREVKGGEKADGGKK-GKSEGTQVTSSAAGPVT
At4g14540-NF-YB3     83  DDLLWAMTLGFEDYVEPLKVYLMREEC----------------TTGRQGDKEG
At2g38880-NF-YB1     83  DDLLWAMATLGFEDYVEPLKYLARYREETN--------------VLFIPWDWLLT
At5g47640-NF-YB2     89  DDLLWAMTLGFEDYVEPLKVYLRREEC----------------GLGRPQTGGEV Arabidopsis-LEC1    181  GLPPPGPYGYGMLDQSMVMGGGRYYQNGSSQDESSVGGGSSSSINGMPAFDHYGQYK
EMRE1EUKT264674     144  GTALAEPQGDSRVESTESSSPEQQHESAGRAVSRQPFS------------------
At4g14540-NF-YB3    128  GGGGGGAGSGSGAPMYGGGVTTMGHQGHHFS--------------------------
At2g38880-NF-YB1    128  HHLLMQLEGNKGSKSGDSNRDAGGGVGEEMPSW------------------------
At5g47640-NF-YB2    134  GEHQRDAVGDGGGFYGGGQYHQHEQLHQQNHMYGATGGGSDSGGGAASGRTRT-
```

FIG. 1

REQDRYLPIANISRIMKKSLPANAKIAKDAKETVQECVSEFISFITSEASDKCQQE
1     7    13  17   23   28   34    41       50,51,52

KRKTINGDDLLWAMSTLGFDKYVEPLKHYLVKYRE                (SEQ ID NO:4)
57  62,63,64    72         83    91

FIG. 4
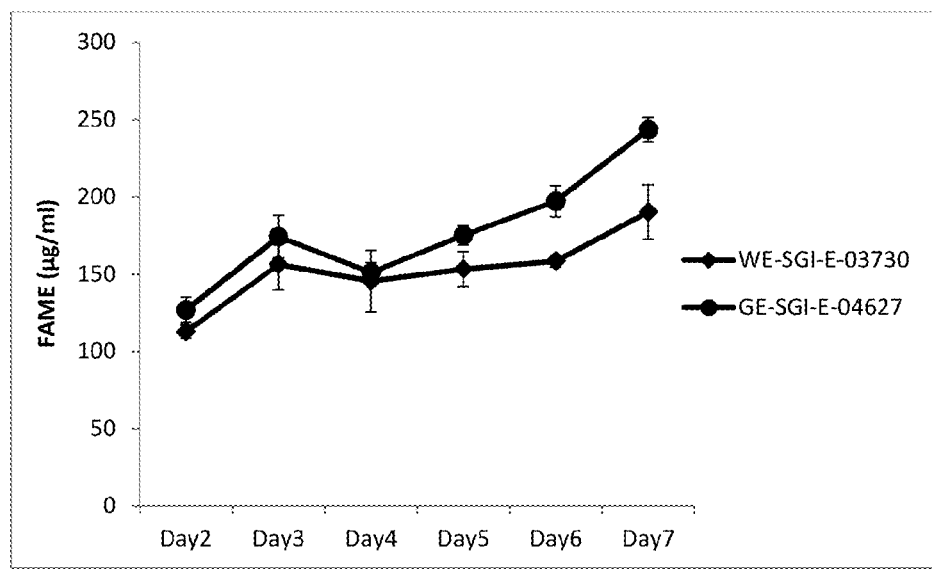
FIG. 4A
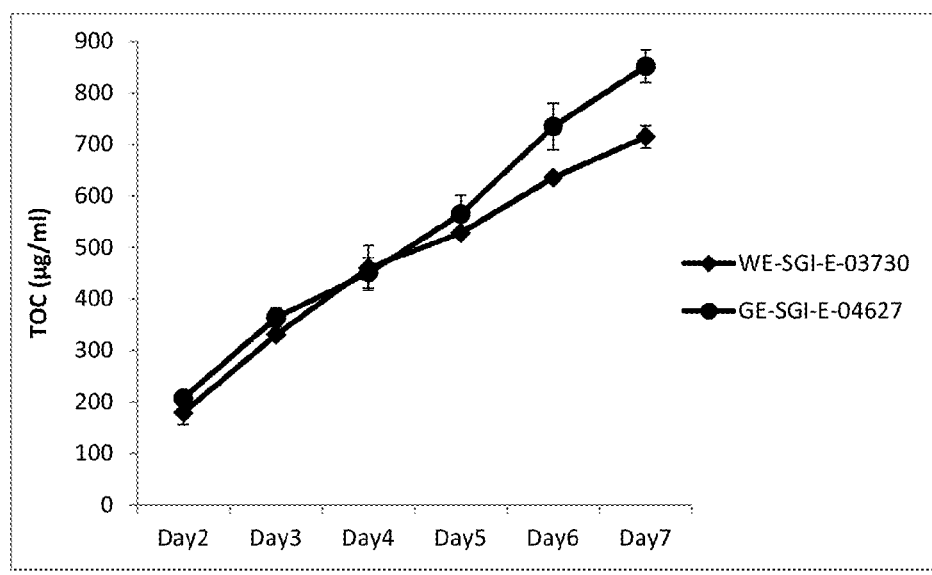
FIG. 4B

COMPOSITIONS AND METHODS FOR MODULATING BIOMASS PRODUCTIVITY

CROSS-REFERENCE TO RELATED APPLICATIONS

This application claims benefit of priority under 35 U.S.C. §119(e) of U.S. Ser. No. 61/887,226 filed 4 Oct. 2013, the entire contents of which are incorporated herein by reference in their entireties.

FIELD OF THE INVENTION

The present application relates generally to the field of molecular biology and genetics. Specifically, this application relates to methods and materials involved in modulating biomass productivity in microorganisms such as, for example, microalgae. This application further provides recombinant microorganisms such as microalgae having increased productivity.

INCORPORATION OF SEQUENCE LISTING

The material in the accompanying sequence listing is hereby incorporated by reference into this application. The accompanying sequence listing text file, name SGI1720_1WO_Sequence_Listing, was created on 3 Oct. 2014, and is 81 kb. The file can be accessed using Microsoft Word on a computer that uses Windows OS.

BACKGROUND OF THE INVENTION

Transcription factors can modulate gene expression, either increasing or decreasing (inducing or repressing) the rate of transcription. This modulation results in differential levels of gene expression at various developmental stages, in different growth phases and cell types, and in response to different exogenous (e.g., environmental) and endogenous stimuli throughout the life cycle of the organism. Because transcription factors are key controlling elements of biological pathways, altering the expression levels of one or more transcription factors can change entire biological pathways in an organism.

Transcriptional regulation of most eukaryotic genes occurs through the binding of transcription factors to sequence specific binding sites in their promoter regions. Many of these protein binding sites have been conserved through evolution and are found in the promoters of diverse eukaryotic organisms. One such feature that shows a high degree of conservation is the CCAAT-box (Edwards et al, *Plant Physiol.* 117:1015-1022, 1998). The CCAAT family of transcription factors, also be referred to as the "CART", "CAAT-box" or "CCAAT-box" family, are characterized by their ability to bind to a CCAAT-box element in the upstream region of a gene, typically located 80 to 300 bp 5' from a transcription start site (Gelinas et al., *Nature* 313: 323-325, 1985). This cis-acting regulatory element is found in all eukaryotic species and is estimated to be present in the promoter and/or enhancer regions of approximately 30% of genes (see, e.g. Bucher and Trifonov, *J. Biomol. Struct. Dyn.* 5: 1231-1236, 1988; Bucher, *J. Mol. Biol.* 212:563-578, 1990). The CCAAT-box element can function in either orientation, and can operate alone or in cooperation with other cis regulatory elements (Tasanen et al., *J. Biol. Chem.* 267:11513-11519, 1992).

CCAAT-box binding proteins constitute a large family of transcription factors first identified in yeast and named HAP for Heme-Activation Protein. They combine to form a heteromeric protein complex that activates transcription by binding to CCAAT boxes in eukaryotic promoters. In plants, CCAAT binding transcription factors are thought to bind DNA as heterotrimers composed of HAP2-like, HAP3-like and HAP5-like subunits. The HAP heterotrimer is also referenced in the scientific literature as the CCAAT box binding factor (CBF) or Nuclear Factor Y (NF-Y), which comprises an NF-YA subunit (corresponding to the HAP2-like subunit), an NF-YB subunit (corresponding to the HAP3-like subunit) and an NF-YC subunit (corresponding to the HAP5-like subunit) (Mantovani et al., *Nucl. Acids Res.* 20: 1087-1091, 1992; Mantovani, *Gene* 239:15-27, 1999; Gusmaroli et al., *Gene* 264:173-185, 2001; Gusmaroli et al., *Gene* 283:41-48, 2002). HAP2-, HAP3- and HAP5-like proteins have two highly conserved sub domains, one that functions in subunit interaction and the other that acts in a direct association with DNA. Outside of these two regions, HAP-like proteins can be quite divergent in sequence and in overall length. Throughout the disclosure, the HAP terminology is used for the NF-YB subunit, and in particular, the term "HAP3-like protein" or "HAP3 protein" is used, but other names such as CBF-A and NF-YB are interchangeable and denote the same protein. The NF-Y terminology is most commonly used herein for HAP3 partners, for example, and its transcription factor complex partners of HAP3 (NF-YB) are referred to herein as "NF-YA" (HAP2) and "NF-YC" (HAP5)".

In yeast, there is a single gene for each HAP subunit (e.g., HAP2, HAP3, and HAP5), and the HAP proteins are involved in the transcriptional control of metabolic processes such as the regulation of catabolic derepression of cyc1 and other genes involved in respiration (Becker et al., *Proc. Natl. Acad. Sci. USA* 88:1968-1972, 1991). In contrast, multiple forms of each HAP homolog have been identified in plants (Edwards et al, 1998, supra; Gusmaroli et al., 2002, supra). The general domain structure of HAP3-like proteins has been documented in great detail (see, e.g. U.S. Pat. No. 7,868,229; Lotan et al., *Cell* 93:1195-1205, 1998). HAP3-like proteins contain an amino-terminal A domain, a central B domain and a carboxy-terminal C domain. There is very little sequence similarity between different HAP3-like protein family members (paralogs) in the A and C domains; it is therefore widely assumed that the A and C domains could provide a degree of functional specificity to each member of the HAP3-like protein subfamily.

Generally, HAP3-like proteins comprise a "conserved protein-protein and DNA-binding interaction module" within their histone fold motif or "HFM" (Gusmaroli et al., *Gene* 283:41-48, 2002). The HFM, which is reported to be required for HAP function (Edwards et al., *Plant Physiol.* 117:1015-1022, 1998), is within the larger highly conserved B domain (Lee et al., *Proc. Natl. Acad. Sci.* 100: 2152-2156, 2003) which is responsible for both DNA binding and subunit association. According to Gusmaroli et al., 2002, supra "all residues that constitute the backbone structure of the HFMs are conserved, and residues such as AtNF-YB-10 [At3g53340; an *Arabidopsis* HAP3-like protein] N38, K58, and Q62, involved in CCAAT-binding, and E67 and E75, involved in NF-YA association (Maity and de Crombrugghe, *Trends Biochem Sci.* 23:174-178, 1998; Zemzoumi et al., *J. Mol. Biol.* 286:327-337, 1999), are maintained".

Leafy cotyledon1 (LEC1), one of ten HAP3-like proteins encoded by the *Arabidopsis thaliana* genome, has been identified as a central regulator that affects embryogenesis (as does the related "LEC1-like" or "L1L" protein (Kwong et al. *The Plant Cell* 15:5-18, 2003) and oil accumulation in maize embryos (U.S. Pat. No. 7,294,759). Like other HAP3-like proteins, LEC1 has three domains: an amino terminal A domain, a central B domain, and a carboxyl terminal C (Harada et al., *Proc. Natl. Acad. Sci* 100(4): 2152-2156, 2003). The B domain typically includes about 90 residues and often has a conserved signature sequence of 7 residues of Met Pro Ile Ala Asn Val Ile (MPIANVI), sometimes referred to as the PIANO motif. The LEC1 and L1L proteins also have sixteen conserved amino acids within the B domain that differ from the amino acids at the same positions of the B domain in other HAP3-like proteins, which are known as the "non-LEC1-type" HAP3-like proteins (Kwong et al., 2003, supra; Lee et al., 2003, supra). Molecular and genetic analysis revealed non-LEC1 like HAP3-like protein family members of higher plants to be involved in the control of diverse biological processes including drought tolerance (Nelson et al. *Proc. Natl. Acad. Sci* 104: 16450-16455) and timing of flowering (U.S. Pat. No. 7,868,229).

Microalgae have recently attracted considerable interest owing to numerous consumer products and applications that can be produced from these organisms. The microalgae-based product portfolio stretches from biomass production for food and animal feed to valuable products extracted from microalgal biomass, including triglycerides which can be converted into biodiesel. For most of these applications, the production process is moderately economically viable and the market is developing. With the development of advanced culture and screening techniques, microalgal biotechnology can help meet the high demands of food, pharmaceutical, and energy industries.

SUMMARY OF THE INVENTION

The present application describes the discovery of genes that, when overexpressed in eukaryotic micooroganisms such as algae and heterokonts, confer increased productivity on the micooroganisms.

In one aspect the present invention provides isolated or recombinant nucleic acid molecules that encode polypeptides that include amino acid sequences having at least 65%, at least 70%, at least 75%, at least 80%, at least 85%, at least 90%, at least 95%, at least 96%, at least 97%, at least 98%, or at least 99% identity to a HAP3-like protein B domain selected from the group consisting of SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 29-119 of SEQ ID NO:26, amino acids 26-116 of SEQ ID NO:28, amino acids 23-113 of SEQ ID NO:30, amino acids 26-116 of SEQ ID NO:32, amino acids 20-110 of SEQ ID NO:34, amino acids 16-106 of SEQ ID NO:36, amino acids 24-114 of SEQ ID NO:38, amino acids 21-111 of SEQ ID NO:40, amino acids 29-119 of SEQ ID NO:42, amino acids 20-110 of SEQ ID NO:44, amino acids 20-110 of SEQ ID NO:46, amino acids 9-96 of SEQ ID NO:50, and amino acids 16-106 of SEQ ID NO:52. The amino acid sequences can comprise, for example, a non-LEC1 type HAP3-like protein B domain. The non-LEC1 type HAP3-like protein B domain amino acid sequence in some examples can include the amino acid motif of SEQ ID NO:2 or SEQ ID NO:3. Alternatively, a non-LEC1 type HAP3-like protein B domain can include the amino acid sequence motif of SEQ ID NO:61 or SEQ ID NO:62. The isolated or recombinant nucleic acid molecules can encode polypeptides with at least 50%, at least 55%, at least 60%, at least 65%, at least 70%, at least 75%, at least 80%, at least 85%, at least 90%, at least 95%, at least 96%, at least 97%, at least 98%, or at least 99% identity to a HAP3-like polypeptide of a plant or microbial species, such as, for example, a non-LEC1-type HAP3-like polypeptide of a plant, microalga or heterokont species. For example, the nucleic acid molecules provided herein encode polypeptides having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 SEQ ID NO:34, SEQ ID NO:36, SEQ ID NO:38, SEQ ID NO:40, SEQ ID NO:50, or SEQ ID NO:52.

The isolated or recombinant nucleic acid molecules provided herein can in some examples have nucleotide sequences that are different from (i.e., not 100% identical to) a nucleotide sequence of a naturally-occurring gene and/or the isolated or recombinant nucleic acid molecule can comprise a cDNA that lacks one or more introns present in the naturally-occurring gene.

Further, an isolated or recombinant nucleic acid molecule as disclosed herein, when expressed in a microbial cell, can confer higher productivity on the microbial cell. For example, expression of a nucleic acid molecule as disclosed herein in a genetically engineered microalgal or heterokont cell can result in the genetically engineered microalgal or heterokont cell having higher productivity when compared with a control cell that does not express the nucleic acid molecule, for example, the genetically engineered microalgal or heterokont cell can demonstrate a higher growth rate, greater biomass accumulation or productivity, or higher rate or level of production of a biomolecule such as, for example, a lipid, protein, polymer, pigment, or carbohydrate, including an alcohol, as compared with a control or wild-type cell.

In particular examples, provided herein are isolated or recombinant nucleic acid molecules that include a nucleic acid sequence encoding a polypeptide, such as a HAP3-like protein, having at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or SEQ ID NO:24, or to a functional fragment of any thereof, in which the polypeptide includes a HAP3-like protein B domain having at least 85%, at least 90%, at least 95%, at least 96%, at least 97%, at least 98%, or at least 99% identity to SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, or amino acids 26-116 of SEQ ID NO:24.

Also provided herein is nucleic acid molecule having at least about 30%, 35%, 40%, or 45% nucleotide sequence identity, and in some examples at least about 50%, at least about 55%, at least about 60%, at least about 65%, at least about 70%, at least about 75%, or at least about 80% sequence identity, for example at least about 85%, at least about 90%, at least about 95% or at least about 97% or more sequence identity, to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:49, and SEQ ID NO:51, or to a region or fragment of any of these sequences. For example, a nucleic acid molecule as provided herein can in some examples have at least 50%, at least 55%, at least 60%, at least 65%, at least 70%, at least 75%, or at least 80% sequence identity, for example at least 85%, at least 90%, at least 95%, or at least 97% sequence identity to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21, or SEQ ID NO:23. The nucleic acid molecule can encode a HAP3-like polypeptide, such as any disclosed herein, for example, a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to a HAP3-like polypeptide, including a non-LEC1-type HAP3-like protein, including a microbial non-LEC1-type HAP3-like protein, such as for example, to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, or SEQ ID NO:52. In further examples, a nucleic acid molecule as provided herein can have at least 85%, at least 90%, at least 95%, or at least 97% sequence identity to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:33, SEQ ID NO:35, SEQ ID NO:37, SEQ ID NO:39, SEQ ID NO:49, and SEQ ID NO:51 or a complement of any thereof, thereof, including a complement of a portion of any of the foregoing sequences that can be provided, for example, in an RNAi or antisense RNA construct. Further provided are isolated or recombinant nucleic acid molecules comprising nucleic acid sequences which are an interfering RNA to any of the nucleotide sequences provided herein. Also included are nucleic acid molecules encoding variants of HAP3-like proteins, and recombinant HAP3-like polypeptides encoded by any of the recombinant nucleic acid molecules provided herein.

Also provided herein are nucleic acid molecules that encode a NF-YC polypeptide having at least 65%, at least 70%, at least 75%, or at least 80% sequence identity, for example at least 85%, at least 90%, at least 95%, at least 96%, or at least 97%, at least 98%, at least 99%, or 100% identity to SEQ ID NO:64, SEQ ID NO:65, SEQ ID NO:66, or SEQ ID NO:68. The polypeptide can be a NF-YC polypeptide. In some examples, the nucleic acid molecules can have at least 50%, at least 55%, at least 60%, at least 65%, at least 70%, at least 75%, or at least 80% sequence identity, for example at least 85%, at least 90%, at least 95%, or at least 97% sequence identity to SEQ ID NO:63.

Further provided herein are nucleic acid molecules that encodes a NF-YA polypeptide having at least 65%, at least 70%, at least 75%, or at least 80% sequence identity, for example at least 85%, at least 90%, at least 95%, at least 96%, or at least 97%, at least 98%, at least 99%, or 100% identity to SEQ ID NO:70. The polypeptide can be a NF-YA polypeptide. In some examples, the nucleic acid molecule can have, in some examples, at least 50%, at least 55%, at least 60%, at least 65%, at least 70%, or at least 75%, or at least 80% sequence identity, for example at least 85%, at least 90%, at least 95%, or at least 97% sequence identity to SEQ ID NO:69.

The invention also provides nucleic acid constructs comprising a nucleic acid sequence as provided herein operably linked to one or more sequences that can regulate or mediate transcription, translation, or integration of nucleotide sequences into a host genome. Further included are vectors that comprise a nucleic acid molecule as provided herein.

Another aspect of the invention is a recombinant microorganism that includes a non-native nucleic acid molecule encoding a polypeptide that includes an amino acid sequence having at least 65%, at least 70%, at least 75%, at least 80%, at least 85%, at least 90%, at least 95%, at least 96%, at least 97%, at least 98%, or at least 99% identity to a HAP3-like protein B domain selected from the group consisting of: SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 26-116 of SEQ ID NO:34, amino acids 20-110 of SEQ ID NO:36, amino acids 16-106 of SEQ ID NO:38, amino acids 24-114 of SEQ ID NO:38, amino acids 21-111 of SEQ ID NO:40, amino acids 29-119 of SEQ ID NO:42, amino acids 20-110 of SEQ ID NO:44, amino acids 20-110 of SEQ ID NO:46, amino acids 6-96 of SEQ ID NO:50, and amino acids 16-106 of SEQ ID NO:52. The polypeptide encoded by the non-native nucleic acid molecule is preferably a HAP3-like protein, such as a polypeptide having at least 50% identity to a naturally-occurring HAP3-like protein of a plant or microorganism, e.g., an alga or heterokont. In various examples, the recombinant microorganism includes a non-native gene encoding a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:50, or SEQ ID NO:52. The recombinant microorganism can exhibit higher productivity than is exhibited by a control cell substantially identical to the recombinant microorganism that includes the non-native gene encoding a polypeptide having a HAP3-like protein B domain-homologous sequence, with the exception that the control cell does not include a non-native gene encoding a polypeptide having a HAP3-like protein B domain sequence. For example, expression of the non-native gene in an algal or heterokont cell can result in the algal or heterokont cell producing a greater amount of biomass or a greater amount of one or more biomolecules, such as, without limitation, a lipid, a terpenoid, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant.

Another aspect of the invention is a recombinant microorganism that includes a non-native nucleic acid molecule encoding a polypeptide that includes an amino acid sequence having at least 65%, at least 70%, at least 75%, at least 80%, at least 85%, at least 90%, at least 95%, at least 96%, at least 97%, at least 98%, or at least 99% identity to a non-LEC1 type HAP3-like protein B domain selected from the group consisting of: SEQ ID NO:4, amino acids 27-117 of SEQ ID NO:8; amino acids 23-113 of SEQ ID NO:10;

amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 26-116 of SEQ ID NO:34, amino acids 20-110 of SEQ ID NO:36, amino acids 16-106 of SEQ ID NO:38, amino acids 24-114 of SEQ ID NO:38, amino acids 21-111 of SEQ ID NO:40, amino acids 6-96 of SEQ ID NO:50, and amino acids 16-106 of SEQ ID NO:52. The polypeptide encoded by the non-native nucleic acid molecule is preferably a non-LEC1 type HAP3-like protein, such as a polypeptide having at least 50% identity to a naturally-occurring non-LEC1 type HAP3-like protein of a plant or microorganism, e.g., an alga or heterokont. In various examples, the recombinant microorganism includes a non-native gene encoding a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, or SEQ ID NO:52. The recombinant microorganism can exhibit higher productivity than is exhibited by a control cell substantially identical to the recombinant microorganism that includes the non-native gene encoding a polypeptide having a HAP3-like protein B domain-homologous sequence, with the exception that the control cell does not include a non-native gene encoding a polypeptide having a HAP3-like protein B domain sequence.

A recombinant microorganism having a non-native gene encoding a polypeptide having a HAP3-like protein B domain can comprise, e.g., any of the nucleic acid molecules encoding a polypeptide that includes a HAP3-like B domain, including a non-LEC1 type HAP3-like B domain, as described herein. The nucleic acid sequence can encode a polypeptide that is heterologous (of a different species) with respect to the recombinant host cell or organism or homologous (of the same species) with respect to the recombinant host cell or organism. The nucleic acid molecule can encode a variant of a naturally-occurring polypeptide that may be either homologous or heterologous with respect to the host cell or organism.

In various examples, the non-native gene encodes a non-LEC type HAP3-like polypeptide that is derived from an algal species or a polypeptide having at least 65% identity to or example, a microorganism can comprise a non-native gene encoding a non-LEC type HAP3-like polypeptide having at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, or SEQ ID NO:40. The polypeptide encoded by the non-native gene can include a non-LEC type HAP3-like B domain. For example, the The polypeptide encoded by the non-native gene can include an amino acid motif of SEQ ID NO:2, SEQ ID NO:3, SEQ ID NO:61, or SEQ ID NO:62. Alternatively or in addition, the polypeptide encoded by the non-native gene can include a non-LEC type HAP3-like B domain having at least 65%, at least 70%, at least 75%, at least 80%, at least 85%, at least 90%, at least 95%, at least 96%, at least 97%, at least 98%, or at least 99% identity to a non-LEC1 type HAP3-like protein B domain selected from the group consisting of: SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 26-116 of SEQ ID NO:34, amino acids 20-110 of SEQ ID NO:36, amino acids 16-106 of SEQ ID NO:38, amino acids 24-114 of SEQ ID NO:38, and amino acids 21-111 of SEQ ID NO:40.

Further provided is a recombinant microorganism that includes a non-native nucleic acid molecule encoding a polypeptide that includes an amino acid sequence having at least 65%, at least 70%, at least 75%, at least 80%, at least 85%, at least 90%, at least 95%, at least 96%, at least 97%, at least 98%, or at least 99% identity to a a polypeptide having at least 65%, at least 70%, at least 75%, or at least 80% sequence identity, for example at least 85%, at least 90%, at least 95%, at least 96%, or at least 97%, at least 98%, at least 99%, or 100% identity to SEQ ID NO:64, SEQ ID NO:65, SEQ ID NO:66, or SEQ ID NO:68. The polypeptide can by an NF-YC protein.

Further provided is a recombinant microorganism that includes a non-native nucleic acid molecule encoding a polypeptide that includes an amino acid sequence having at least 65%, at least 70%, at least 75%, at least 80%, at least 85%, at least 90%, at least 95%, at least 96%, at least 97%, at least 98%, or at least 99% identity to SEQ ID NO:70. The polypeptide can by an NF-YA protein.

Also contemplated are recombinant microorganisms that include non-native genes encoding any combination of a HAP3-like protein as disclosed herein, an NF-YC protein as disclosed herein, and an NF-YA protein as disclosed herein. A host cell that includes a non-native gene as provided herein that encodes a HAP3-like or HapY polypeptide, homolog, or variant can further include one or more additional non-native genes that may confer any trait of interest, such as, but not limited to, traits relating to production of biomolecules of interest, such as one or more proteins, pigments, alcohols, or lipids. For example, a recombinant microorganism as provided herein can include non-native genes encoding a non-LEC1 type HAP3-like protein as described herein.

Suitable host cells to be modified using the materials and methods according to the present invention include, but are not limited to, bacteria, protists, microalgae, phytoplankton, heterokonts, fungi, and protozoa. Heterokont species considered for use in the invention include, but are not limited to, Bacillariophytes and Eustigmatophytes, as well as Labrinthulids and Thraustochytrids, such as, for example, species of *Labryinthula, Thraustochytrium, Schizochytrium, Ulkenia*, or *Aplanochytrium, Aurantiochytrium, Japonochytrium, Diplophrys*, or *Ulkenia*.

Algal species suitable for the method of the invention include microalgae such as, for example, species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris,*

*Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*. Non-limiting examples of exemplary species include, for instance, eustigmatophytes or diatoms such as, for example, a species of any of the genera *Amphora, Chaetoceros, Cyclotella, Eustigmatos, Fragilaropsis, Monodus, Nannochloropsis, Navicula, Nitzschia, Phoedactylum, Thalassiosira,* or *Vischeria*.

A microorganism that includes a non-native gene encoding a polypeptide having a HAP3-like B domain as provided herein, such as, for example, a non-LEC1-type HA3-like B domain, or an NF-YC or NF-YA protein as disclosed herein, can have improved productivity when compared with a control microorganism that does not include the non-native gene encoding a HAP3-like B domain containing polypeptide, NF-YC protein, or NF-YA protein. Higher productivity can be demonstrated, for example, by measuring growth rates or total organic carbon (TOC) or ash free dry weight accumulation, or by quantitating any of various biomolecules produced by the recombinant microorganism (such as for example, one or more lipids, polymers, proteins, pigments, carbohydrates, etc.).

Also provided herein are methods of producing biomass or at least one bioproduct by culturing microbial cells having a modulated growth characteristic, such as the recombinant host cells disclosed herein. The methods include culturing a microbial cell as disclosed herein that includes a non-native gene encoding a HAP3-like protein, or an NF-YC or NF-YA protein, as such as a nucleic acid molecule as disclosed herein that encodes a HapY protein or HAP3-like protein, or an NF-YC or NF-YA protein, in a suitable medium to provide an algal culture and recovering biomass or at least one bioproduct from the culture. The method can optionally include inducing expression of the non-native gene that encodes the HAP3-like protein or NF-YC or NF-YA protein. The microorganism in some examples can be a microalga. The algal culture can be a photoautotrophic culture. Non-limiting examples of products that can be made using the methods include biomass, lipids, polyketides, terpenoids, pigments, antioxidants, vitamins, nucleotides, nucleic acids, amino acids, carbohydrates, alcohols, hormones, cytokines, peptides, proteins, or a polymers.

BRIEF DESCRIPTION OF THE DRAWINGS

FIG. 1 is a sequence alignment of the *Nannochloropsis gaditana* HapY (SEQ ID NO:6), *Arabidopsis thaliana* LEC1 (At1g21970; SEQ ID NO:48); *Arabidopsis thaliana* NF-YB1 (SEQ ID NO:44), *Arabidopsis thaliana* NF-YB2 (SEQ ID NO:42), *Arabidopsis thaliana* NF-YB3 (At4g14540; SEQ ID NO:46).

FIGS. 4A, 4B, and 4C illustrate the results of experiments assessing productivity level of the recombinant cell line GE-4627 in a constant light productivity assay (see, e.g. Example 2). The graphs represent the relative amounts of fatty acid methyl esters (FAME) and total organic carbon (TOC) of *Nannochloropsis* cells overexpressing HapY compared to wild-type controls. Values are the means of single day productivity values of three biological replicates for GE-4627 (blue diamond) and two biological replicates for WT-3730 (orange circle). FIG. 4A. Fatty acid methyl esters (FAME) analysis. The graphs represent the relative amounts of FAMEs produced by the recombinant cell and wild-type control; FIG. 4B. Total organic carbon (TOC) values; FIG. 4C. FAME/TOC values for recombinant cells WT-3730 and wild-type control GE-4627.

FIG. 5A. Fatty acid methyl esters (FAME) analysis of GE-4627 transgenic cells compared to wild-type control WT-3730; FIG. 5B. Total organic carbon (TOC) values for GE-4627 transgenic cells compared to wild-type control WT-3730. Two biological replicates are shown for wild-type WT-3730 (green circles and squares) and transgenic line GE-4627 (blue circles and squares).

DETAILED DESCRIPTION OF THE INVENTION

Figures 2, 3:
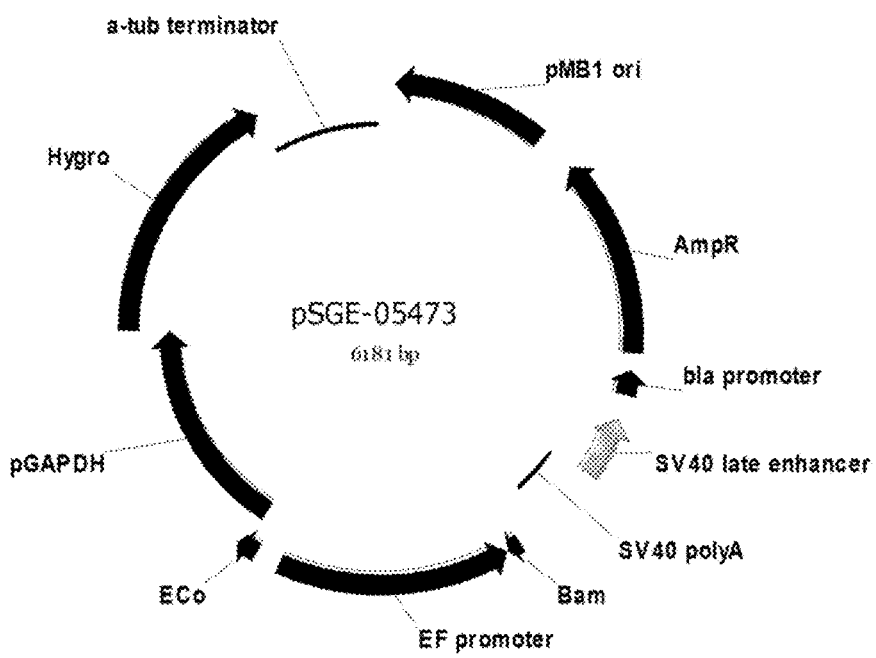
FIG. 2 provides the sequence of the B domain of the non-LEC1 type HAP3-like protein "HapY" of *Nannochloropsis gaditana* (SEQ ID NO:6). Amino acid residues that differ with respect to the amino acids that are diagnostic of LEC1 type HAP3 polypeptides are numbered and underlined.
FIG. 3 is a schematic representation of the vector pSGE05473, one of several vectors used for overexpressing transcription factors in *Nannochloropsis*, which included an elongation factor promoter EF promoter (SEQ ID NO:53) used to overexpress a coding sequence of interest, e.g. the *Nannochloropsis* HapY gene, and a glyceraldehyde-3-phosphate dehydrogenase promoter (pGAPDH) from *Phaeodactylum tricornutum*, driving expression of a hygromycin resistance gene (HygroR) for selection in algal cells. Also included was an ampicillin resistance gene for selection in *E. coli* cells.

The present application relates to compositions, methods and related materials for modifying characteristics of microorganisms, particularly those associated with improved productivity. In various aspects, the application discloses recombinant microorganisms, such as microalgae and heterokonts that express a non-native gene encoding a regulatory protein that affects productivity, such as, for example, biomass productivity.

Throughout this disclosure, various information sources are referred to and/or incorporated by reference. The information sources include, for example, scientific journal articles, patent documents, textbooks, and World Wide Web browser-inactive page addresses. While the reference to these information sources clearly indicates that they can be used by one of skill in the art, each and every one of the information sources cited herein are specifically incorporated by reference in their entirety, whether or not a specific mention of "incorporation by reference" is noted. It should also be noted that the reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

Headings within the application are solely for the convenience of the reader, and do not limit in any way the scope of the invention or its embodiments.

SOME DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the teen "a cell" includes one or more cells, including mixtures thereof. "A and/or B" is used herein to include all of the following alternatives: "A", "B", and "A and B".

"About" means plus or minus 10% of the provided value. Where ranges are provided, they are inclusive of the boundary values.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that function in a manner similar to a naturally-occurring amino acid.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, or insertional mutation) or having decreased expression due to alteration of gene regulatory sequences.

"Biofuels", as used herein, refer to renewable energy sources from living organisms, such as higher plants, fungi, algae, or microorganisms. As such, biofuels can be solid, liquid or gaseous fuels derived from algal, fungal, microbial or plant materials, biomass, sugars or starches, such as ethanol or biodiesel derived from vegetable oils or algal oil, and the like. A biofuel is a fuel in its own right, but may be blended with petroleum-based fuels to generate a finished fuel. A biofuel may be used as a replacement for petrochemically-derived gasoline, diesel fuel, or jet fuel.

A "cDNA" is a DNA molecule that comprises at least a portion of the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred examples, a cDNA does not include one or more intron sequences that occur in the naturally-occurring gene (in the genome of an organism) that the cDNA corresponds to. For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene, but are separated by an intron). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences and/or compiled from the sequences of multiple partial cDNAs.

A "control organism", "control microorganism", or "control cell" as used in the present invention provides a reference point for measuring changes in phenotype of the subject organism, microorganism, or cell. A control organism, microorganism, or cell may comprise, for example, (a) a wild-type organism, microorganism, or cell, i.e., of the same genotype as the starting material for the genetic alteration which resulted in the subject organism, microorganism, or cell; (b) an organism or cell of the same genotype as the starting material but which has been transformed with a null construct (i.e. a construct which has no known effect on the trait of interest, such as a construct lacking a gene encoding the polypeptide of interest, e.g., lacking a gene encoding a HAP3-like polypeptide); (c) an organism or cell which is a non-transformed segregant among progeny of a subject organism or cell; or (d) the subject organism, microorganism, or cell itself, under conditions in which the gene of interest is not expressed. In some instances, "control organism" may in some cases refer to an organism that does not contain the exogenous nucleic acid present in the transgenic organism of interest, but otherwise has the same or similar genetic background as such a transgenic organism.

"Domains" are groups of substantially contiguous amino acids in a polypeptide that can be used to characterize protein families and/or parts of proteins. Such domains may have a "fingerprint", "motif", or "signature" that can comprise conserved primary sequence, secondary structure, and/or three-dimensional conformation. Generally, domains are correlated with specific in vitro and/or in vivo activities. A domain can be of any size, by way of example, a domain may have a length of from 4 amino acids to about 400 amino acids, e.g., from 4 to about 50 amino acids, or 4 to about 20 amino acids, or 4 to about 10 amino acids, or about 25 to about 100 amino acids, or about 35 to about 65 amino acids, or about 50 to about 100 amino acids, or about 75 to 120 amino acids, or about 200 to about 300 amino acids, or about 300 to about 400 amino acids.

"Down-regulation" refers to regulation that decreases production of expression products (mRNA, polypeptide, biological activity, or combinations of any thereof) relative to basal or native states.

The term "endogenous," within the context of the present disclosure refers to any polynucleotide, polypeptide or protein sequence which is a natural part of a cell.

"Exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. An nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein "Fragment", with respect to a polynucleotide, refers to a clone or any part of a polynucleotide molecule, particularly a part of a polynucleotide that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, for example at least about 30 nucleotides or at least about 50 nucleotides of any of the sequences provided herein. Exemplary polynucleotide fragments are the first sixty consecutive nucleotides of the polynucleotides listed in the Sequence Listing. Exemplary fragments also include fragments that comprise a region that encodes a conserved B domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, for example at least about 20 amino acid residues in length, for example at least about 30 amino acid residues in length.

The term "functional homolog" as used herein describes those molecules that have sequence similarity and also share at least one functional characteristic such as a biochemical activity. Functional homologs will typically give rise to the same characteristics to a similar, but not necessarily the same, degree. Functionally homologous proteins give the same characteristics where the quantitative measurement produced by one homolog is at least 10% of the other; more typically, at least 20%, between about 30% and about 40%; for example, between about 50% and about 60%; between about 70% and about 80%; or between about 90% and about 95%; between about 98% and about 100%, or greater than 100% of that produced by the original molecule. Thus, where the molecule has enzymatic activity the functional homolog will have the above-recited percent enzymatic activities compared to the original enzyme. Where the molecule is a DNA-binding molecule (e.g., a polypeptide) the homolog will have the above-recited percentage of binding affinity as measured by weight of bound molecule compared to the original molecule.

A functional homolog and the reference polypeptide may be naturally occurring polypeptides, and the sequence similarity may be due to convergent or divergent evolutionary events. Functional homologs are sometimes referred to as orthologs, where "ortholog", refers to a homologous gene or protein that is the functional equivalent of the referenced gene or protein in another species.

Variants of a naturally-occurring functional homolog, such as polypeptides encoded by mutants or a wild-type coding sequence, may themselves be functional homologs. As used herein, functional homologs can also be created via site-directed mutagenesis of the coding sequence for a productivity-modulating polypeptide, for example a HapY polypeptide, or by combining domains from the coding sequences for different naturally-occurring HAP3-like polypeptides. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass-modulating polypeptides. Sequence analysis can involve BLAST, Reciprocal BLAST, or PSI-BLAST analysis of non-redundant databases using amino acid sequence of a biomass-modulating polypeptide as the reference sequence. Amino acid sequence is, in some instances, deduced from the nucleotide sequence. Typically, those polypeptides in the database that have greater than 40% sequence identity are candidates for further evaluation for suitability as a biomass-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in productivity-modulating polypeptides, e.g., conserved functional domains.

As used herein a "HAP3-like polypeptide" or an NF-YB protein is a polypeptide that recruits to pfam PF00808 (histone-like transcription factor (CBF/NF-Y) and archaeal histone) with a bit score greater than the gathering cutoff of 21.1 and an e-value of less than 0.1, and comprises an amino terminal ("A") domain, a carboxy terminal ("C") domain, and, between the A and C domains a "B" domain of approximately 80-120 amino acids, for example between about 80 and about 100 amino acids, that is at least 65% identical in amino acid sequence to a B domain of a characterized HAP3-like polypeptide, and preferably has a B domain at least about 80% identical, e.g., at least 85%, at least 90%, or at least 95% identical to a B domain of a characterized HAP3-like polypeptide. Characterized HAP3-like polypeptides include, for example, HAP3-like polypeptides of *Arabidopsis*, including LEC1 or At1g21970 (AF036684; SEQ ID NO:48), LEC1-like (L1L) or At5g47670 (AY138461); PcL1 (AF533650); At2g47810 (NC_003071); At1g09030 (BT029363); At2g37060 (AK317223); At3g53340 (NM_115194); At2g38880 (BT005536); At5g47640 (NM_124138); At4g14540 (NM_117534); At2g13570 (NM_126937); and At5g47670 (NM_124141), where the numbers in parentheses are Genbank Accession numbers. Additional nonlimiting examples of characterized HAP3-like polypeptides include those of maize (AF410176; NP_001105435; P25209; CAA42234); and soybean (e.g., AY058917 and AY058918) (see, for example, Kwong et al. *The Plant Cell* 15:5-18, 2003).

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., is from a different species with respect to the host cell. For example, a transgenic *Nannochloropsis* microorganism transformed with the coding sequence for a fatty acid desaturase from a *Tetraselmis* microorganism or from a plant is transformed with a heterologous desaturase gene. When referring to nucleic acid sequences operably linked or otherwise joined to one another in a nucleic acid construct or molecule, "heterologous sequences", as used herein, are those that are not operably linked or are not contiguous to each other in nature. For example, a promoter from *Tetraselmis* sp. is considered heterologous to a *Nannochloropsis* coding region sequence. Also, a promoter from a gene encoding a HapY gene from *Nannochloropsis* is considered heterologous to a sequence encoding a *Nannochloropsis* fatty acid desaturase. Similarly, when referring to a gene regulatory sequence or to an auxiliary nucleic acid sequence used for maintaining or manipulating a gene sequence (e.g., a promoter, enhancer, 5' untranslated region, 3' untranslated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source (e.g., different gene, whether from the same or different species as the host organisms) than the gene with which the regulatory or auxiliary nucleic acid sequence is juxtaposed in a construct, genome, chromosome, or episome. When referring to a protein functional domain, such as a localization sequence or a receptor binding site, "heterologous" can also mean that the protein functional domain is from a different source (e.g., protein) than the rest of the protein region with which it is juxtaposed in an engineered protein. Similarly, when referring to a promoter sequence of an engineered gene, "heterologous" means that the promoter is derived from a different gene than that to which it is linked by genetic engineering.

When used in reference to a polynucleotide, a gene, a nucleic acid, a polypeptide, or an enzyme, the term "homologous" refers to a polynucleotide, gene, a nucleic acid, polypeptide, or an enzyme derived from the host species, e.g., is from the same species with respect to the host cell, regardless of whether the homologous polynucleotide, gene, nucleic acid, polypeptide, or enzyme has been introduced into the host cell (exogenous) or is endogenous with respect to the host cell.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The term "mis-expression" refers to an increase or decrease in the transcription of a coding region into a complementary RNA sequence as compared to the parental wild-type, for example, alga or plant. This term also encompasses expression of a gene or coding region for a different time period as compared to the wild-type and/or from a non-natural location within the parental genome. The term "overexpression" or "increased expression" as used herein refers to a greater expression level of a gene, a polynucleotide sequence, or a polypeptide, in a host cell compared to a wild-type cell or a wild-type organism, at any developmental or temporal stage. Methods for increasing expression of genes or gene products are well documented in the art and include, for example, overexpression driven by appropriate promoters (e.g. constitutive promoters), the use of transcription enhancers or translation enhancers. Overexpression may also under control of an inducible or a growth-phase specific promoter. For example, overexpression may occur throughout an algal cell, in specific growth phases of the alga, or in the presence or absence of particular environmental signals, depending on the promoter used.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur. In one example, a non-native gene is a gene that does not occur in the host microorganism in nature. In other examples, a non-native nucleic acid sequence in a recombinant microorganism as provided herein can have an altered coding sequence with respect to the nucleic acid molecule as it occurs in the organism in nature, such that it expresses a polypeptide having a different amino acid sequence than the native polypeptide. Such an altered sequence may alter the functional properties of the protein. For example, for a transcriptional regulator, the binding affinity of the transcriptional regulator for interacting proteins or for regulatory DNA sequences that the transcriptional regulator naturally binds may be altered, affecting the magnitude or even type of affect on transcription of genes it regulates. Alternatively or in addition to coding sequence, a non-native gene can be altered by the addition or removal of one or more introns or sequences that confer stability, processing, transport, or translational efficiency on the encoded RNA. Alternatively or in addition, a non-native nucleic acid sequence in a recombinant microorganism as provided herein can be operably linked to transcriptional regulatory sequences that it is not operably linked to in the genome in which it naturally occurs. A non-native gene operably linked to heterologous regulatory sequences may be expressed to a different degree and/or under different growth or culture conditions than the native gene.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest.

"Percentage of sequence identity," as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (*Add. APL. Math*, 2:482, 1981), by the global homology alignment algorithm of Needleman and Wunsch (*J. Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection. GAP and BESTFIT, for example, can be employed to determine their optimal alignment of two sequences that have been identified for comparison. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, for example, at least 70%, at least 80%, at least 85%, at least 90%, at least 95%, or at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Query nucleic acid and amino acid sequences were searched against subject nucleic acid or amino acid sequences residing in public or proprietary databases. Such searches were done using the National Center for Biotechnology Information Basic Local Alignment Search Tool (NCBI BLAST v 2.18) program. The NCBI BLAST program is available on the internet from the National Center for Biotechnology Information (blastncbi.nlm.nih.gov/Blastcgi). Typically the following parameters for NCBI BLAST were used: Filter options were set to "default", the Comparison Matrix was set to "BLOSUM62", the Gap Costs were set to "Existence: 11, Extension: 1", the Word Size was set to 3, the Expect (E threshold) was set to 1e-3, and the minimum length of the local alignment was set to 50% of the query sequence length. Sequence identity and similarity may also be determined using GENOMEQUEST™ software (Gene-IT, Worcester, Mass. USA).

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or, in the case of peptidomimetics, other bonds such as, for example, ester or ether bonds. Full-length polypeptides, truncated polypeptides, point mutants, insertion mutants, splice variants, chimeric proteins, and fragments thereof are encompassed by this definition. As used herein, the expression "substantially conserved amino acid sequences" refers to regions of amino acid homology between polypeptides of the same type or family from different sources. In the present invention, examples of substantially conserved amino acid sequences include those specified in FIG. 1 for HAP3-like polypeptides. One skilled in the art could align the amino acid sequences of HAP3-like polypeptides, including HapY polypeptides, from different sources to the schematic of FIG. 1 to identify the segments therein which are the substantially conserved amino acid sequences defined herein. The skilled person could then determine whether the identified segments have the characteristics disclosed and claimed in the present invention.

As used herein "progeny" means a descendant, offspring, or derivative of an organism. For example, daughter cells from a transgenic alga are progeny of the transgenic alga. Because certain modifications may occur in succeeding generations due to either mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence.

The term "recombinant protein" as used herein refers to a protein produced by genetic engineering, for example, by expression of a genetically engineered nucleic acid molecule in a cell.

The term "regulatory region" "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, zinc finger nucleases, TALENs, or cas nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their nucleotide or amino acid sequences as compared to a reference polypeptide or polynucleotide, respectively, such that the variant has at least 70% sequence identity to the reference polypeptide or polynucleotide. In other embodiments the variant can have at least 80%, at least 95%, at least 90% or at least 95%, at least 97%, at least 98%, or at least 99% sequence identity to the reference polypeptide or polynucleotide. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.). Variants of proteins include N or C terminally truncated proteins, for example, having from one to one hundred amino acids deleted fro the N-terminal or C-terminal end of the protein.

As used herein, "vector" refers to a nucleic acid molecule that includes at least one of a selectable marker gene or an origin of replication or autonomous replication sequence (ARS) that allows the vector to be replicated in a host cell, and in some examples includes both a selectable marker gene and at least one origin of replication or ARS. A vector in various examples includes one or more expression sequences and/or can include at least one sequence for mediating recombination.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

HAP3 (NF-YB) Subunits of the CCAAT-Box Binding Transcription Factor Family

FIG. 1 provides a sequence alignment generated using the program Clustal W (1.83) (Thompson et al., *Nucleic Acids Res.*, November 11; 22:4673-80, 1994) with default settings and black and gray boxes were generated using the BOX-SHADE (3.21) algorithm (www.ch.embnet.org/softvvare/BOX_form.html). Several polypeptide domains and motifs with high degree of conservation have been identified from this sequence comparison analysis of *Nannochloropsis* Hap-Y (SEQ ID NO:6) with HAP3 (also called NF-YB) polypeptides of *Arabidopsis*. In the alignment figure shown herein, a dash in an aligned sequence represents a gap, i.e., a lack of an amino acid at that position. Black boxes and gray boxes identify identical amino acids and conserved amino acids, respectively, among aligned sequences. The conserved DNA-binding regions and the subunit interaction regions, previously described in; e.g. U.S. Pat. No. 6,781, 035; are indicated. In the alignment, the conserved B domains appear between the two parentheses. The amino acid residues corresponding to the conserved B domains of each of the HAP3/NF-YB polypeptides are also indicated in Table 1. The identical residues, conserved residues, conserved motifs, and conserved domains, identified as such in this alignment, constitute non-limiting exemplifications of conserved amino acid residues and features in the sequences of HAP3/NF-YB polypeptides from different organisms.

The non-LEC1-type HAP3-like proteins provided herein (e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, and SEQ ID NO:52) lack the amino acids characteristic of LEC1 and L1L HAP3-like proteins in the specified positions of their B domains (corresponding to amino acid positions 7, 13, 17, 23, 28, 34, 41, 50, 51, 52, 57, 62, 63, 64, 72, and 83 of SEQ ID NO:4 as shown in FIG. 2 when the amino acids of the non-LEC1-type HAP3 protein are aligned with SEQ ID NO:4 for maximum homology).

The amino acids characteristic of LEC1-type HAP3-like proteins are, using the amino acid numbering of FIG. 1: M64, I70, R74, H80, D85, I91, Y98, N107, E108, R109, Q114, T119, A120, E121, K129, and T140. These amino acids correspond to positions 7, 13, 17, 23, 28, 34, 41, 50, 51, 52, 57, 62, 63, 64, 72, and 83 of the amino acid sequence of the B domain of a HAP3-like protein using the numbering system of FIG. 2, which provides the amino acid sequence of the B domain of HapY (SEQ ID NO:4). The non-LEC1 type HAP3-like polypeptides have different amino acids at these positions of the B domain than those listed above (Kwong et al., 2003, supra; Lee et al., 2003, supra), as can be seen in the B domain of the *Nannochloropsis gaditana* HapY polypeptide provided in FIG. 2, where the distinguishing amino acids of LEC1 and LIL B domains (M64, I70, R74, H80, D85, I91, Y98, N107, E108, R109, Q114, T119, A120, E121, K129, and T140) are not found at corresponding positions 7, 13, 17, 23, 28, 34, 41, 50, 51, 52, 57, 62, 63, 64, 72, and 83 of the HapY B domain of *N. gaditana* (SEQ ID NO:4, FIG. 2) or the other algal and heterokont HAP3-like polypeptides (also referred to herein as HapY polypeptides). Thus, when the B domain of a non-LEC1-type HAP3-like protein is aligned with SEQ ID NO:4 (FIG. 2) for maximum homology, the B domain of the non-LEC1 HAP3 protein does not have methionine (M) at position 7, isoleucine (I) at position 13, arginine (R) at position 17, histidine (H) at position 23, aspartate (D) at position 28, isoleucine (I) at position 34, tyrosine (Y) at position 41, asparagine (N) at position 50, glutamate (E) at position 51, arginine (R) at position 52, glutamine (Q) at position 57, threonine (T) at position 62, alanine (A) at position 63, glutamate (E) at position 64, lysine (K) at position 72, and threonine (T) at position 83, using the amino acid position numbering of SEQ ID NO:4 as shown in FIG. 2.

The MPIANVI (SEQ ID NO:1) motif of LEC1 and L1L protein B domains is also not found in non-LEC1 protein B domains (see for example U.S. Pat. No. 7,868,229, FIG. 4B; Lee et al., 2003, supra, FIG. 1; Kwong et al., 2003, supra, FIG. 1). In place of the "PIANO" motif (MPIANVI; SEQ ID NO:1), certain non-LEC1-type HAP3-like proteins, such as for example those disclosed herein, may have the amino acid sequence Leu Pro Ile Ala Asn Ile Ser (LPIANIS; SEQ ID NO:2) or the amino acid sequence Leu Pro Ile Ala Asn Ile Ala (LPIANIA; SEQ ID NO:3) in their B domains. The non-LEC1-type HAP3-like proteins disclosed herein from the Labyrinthylomycetes *Schizochytrium aggregatum* (SEQ ID NO:50) and *Aplanochytrium* sp. (SEQ ID NO:52) have, in place of the "PIANO" motif, the amino acid sequence LPVANIN (SEQ ID NO:61) and LPIANIS (SEQ ID NO:62), respectively.

Polynucleotides and Polypeptides of the Invention

In one aspect of the present invention, the disclosure provides isolated or recombinant nucleic acid molecules, nucleic acid molecules that interfere with these nucleic acid molecules, and nucleic acid molecules that hybridize to these nucleic acid molecules. Additional aspects of the present application include the polypeptides encoded by the isolated or recombinant nucleic acid molecules of the present invention.

An isolated or recombinant nucleic acid molecule as provided herein has a sequence that encodes a polypeptide having an amino acid sequence with at least 65%, at least 70%, at least 75%, at least 80%, at least 85%, at least 90%, at least 95%, at least 96%, at least 97%, at least 98%, or at least 99% identity to a HAP3-like protein B domain selected from the group consisting of SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 29-119 of SEQ ID NO:26, amino acids 26-116 of SEQ ID NO:28, amino acids 23-113 of SEQ ID NO:30, amino acids 26-116 of SEQ ID NO:32, amino acids 20-110 of SEQ ID NO:34, amino acids 16-106 of SEQ ID NO:36, amino acids 24-114 of SEQ ID NO:38, amino acids 21-111 of SEQ ID NO:40, amino acids 29-119 of SEQ ID NO:42, amino acids 20-110 of SEQ ID NO:44, amino acids 20-110 of SEQ ID NO:46, amino acids 9-96 of SEQ ID NO:50, and amino acids 16-106 of SEQ ID NO:52. The encoded polypeptide can comprise, for example, a non-LEC1 type HAP3-like protein B domain. The non-LEC1 type HAP3-like protein B domain amino acid sequence in some examples can comprise the motif of SEQ ID NO:2 or SEQ ID NO:3.

A non-LEC1-type HAP3 polypeptide can be identified by the sequence characteristics of the B domain, as provided hereinabove and depicted, for example, in FIG. 1, in which non-LEC1 type HAP3 proteins are represented by At4g14540 (NF-YB3; NM_117534), At2g38880 (NF-Y81; BT005536), and At5g47640 (NF-YB2; NM_124138).

A "non-LEC1 type HAP3-like protein B domain" is a sequence of approximately 90 amino acids (e.g., 91 amino acids) that has at least 65%, at least 70%, or at least 75%, and in some examples at least 80%, at least 85%, at least 90%, at least 95% identity to the B domain of any characterized non-LEC1-type HAP3 protein, in which the non-LEC1 type HAP3-like protein B domain includes sixteen amino acid residues that are different from the amino acids occurring at the same position of the B domain of LEC1 and LEC1-like (L1L) proteins. The sixteen amino acids identified by Kwong et al. (2003, supra) as characteristic of LEC1 and L1L HAP3-like proteins are, with respect to SEQ ID NO:48 (depicted in FIG. 1 as Arabidopsis LEC1): M64, I70, R74, H80, D85, I91, Y98, N107, E108, R109, Q114, T119, A120, E121, K129, and T140. These are amino acids at positions corresponding to positions 7, 13, 17, 23, 28, 34, 41, 50, 51, 52, 57, 62, 63, 64, 72, and 83 of SEQ ID NO:4, as shown in FIG. 2. Thus, a non-LEC1-type protein B domain does not have one or more of: methionine (M) at the amino acid position corresponding to amino acid position 7 of SEQ ID NO:4; isoleucine (I) at the amino acid position corresponding to amino acid position 13 of SEQ ID NO:4; arginine (R) at the amino acid position corresponding to amino acid position 17 of SEQ ID NO:4; histidine (H) at the amino acid position corresponding to amino acid position 23 of SEQ ID NO:4; aspartate (D) at the amino acid position corresponding to amino acid position 28 of SEQ ID NO:4; isoleucine (I) at the amino acid position corresponding to amino acid position 34 of SEQ ID NO:4; tyrosine at the amino acid position corresponding to amino acid position 41 of SEQ ID NO:4; asparagine (N) at the amino acid position corresponding to amino acid position 50 of SEQ ID NO:4; glutamate (E) at the amino acid position corresponding to amino acid position 51 of SEQ ID NO:4; arginine (R) at the amino acid position corresponding to amino acid position 52 of SEQ ID NO:4; glutamine (Q) at the amino acid position corresponding to amino acid position 57 of SEQ ID NO:4; threonine (T) at the amino acid position corresponding to amino acid position 62 of SEQ ID NO:4; alanine (A) at the amino acid position corresponding to amino acid position 63 of SEQ ID NO:4; glutamate (E) at the amino acid position corresponding to amino acid position 64 of SEQ ID NO:4; lysine (K) at the amino acid position corresponding to amino acid position 72 of SEQ ID NO:4; and threonine (T) at the amino acid position corresponding to amino acid position 83 of SEQ ID NO:4, when the non-LEC1 B domain is aligned with SEQ ID NO:4 for maximum homology. A non-LEC1-type protein as provided herein in some examples includes a B domain that does not have any of the above specified amino acids at the corresponding amino acid positions in the B domain when the B domain of the non-LEC1 protein is aligned with the B domain of SEQ ID NO:4 for maximum homology; for example, with reference to the B domain provided as SEQ ID NO:4, does not have any of: M7, I13, R17, H23, D28, I34, Y41, N50, E51, R52, Q57, T62, A63, E64, K72, and T83.

An isolated or recombinant nucleic acid molecule as provided herein can encode a polypeptide at least 50%, at least 55%, at least 60%, at least 65%, at least 70%, at least 75%, at least 80%, at least 85%, at least 90%, at least 95%, at least 96%, at least 97%, at least 98%, or at least 99% identity to a HAP3-like polypeptide of a plant or microbial species, such as, for example, a non-LEC1-type HAP3-like polypeptide of a plant, microalgal, or heterokont species. Alternatively or in addition, the nucleic acid sequence can encode a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, or SEQ ID NO:52.

In some examples, the isolated or recombinant nucleic acid molecule includes a sequence encoding a polypeptide having a HAP3-like protein B domain having an amino acid sequence with at least 85%, at least 90%, at least 95%, at least 96%, at least 97%, at least 98%, or at least 99% identity to SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 20-110 of SEQ ID NO:34, amino acids 16-106 of SEQ ID NO:36, amino acids 24-114 of SEQ ID NO:38, amino acids 21-111 of SEQ ID NO:40, amino acids 9-96 of SEQ ID NO:50, or amino acids 16-106 of SEQ ID NO:52, in which the polypeptide has at least 50%, at least 55%, at least 60%, at least 65%, at least 70%, at least 75%, at least 80%, at least 85%, at least 90%, at least 95%, at least 96%, at least 97%, at least 98%, or at least 99% identity to a polypeptide of a microalgal or heterokont species, for example, to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, or SEQ ID NO:52. The HAP3-like protein B domain can be a non-LEC1 type HAP3-like protein B domain. A non-LEC1 type HAP3-like protein B domain can in some examples comprise the amino acid sequence of SEQ ID NO:2 or SEQ ID NO:3.

In further examples, provided herein are isolated or recombinant nucleic acid molecules that include a nucleic acid sequence encoding a polypeptide, such as a HAP3-like protein, having at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, or SEQ ID NO:22, in which the polypeptide includes a B domain having at least 85%, at least 90%, at least 95%, at least 96%, at least 97%, at least 98%, or at least 99% identity to SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, or amino acids 18-108 of SEQ ID NO:22. Additionally, the HAP3-like protein B domain can be an non-LEC1 type HAP3-like protein B domain and can comprise the amino acid sequence of SEQ ID NO:2 or SEQ ID NO:3.

In additional examples, provided herein is an isolated or recombinant nucleic acid molecules that include a nucleic acid sequence encoding a polypeptide, such as a HAP3-like protein, having at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, or SEQ ID NO:22, in which the polypeptide includes a B domain having at least 85%, at least 90%, at least 95%, at least 96%, at least 97%, at least 98%, or at least 99% identity to SEQ ID NO:4, to amino acids 58-148 of SEQ ID NO:8; to amino acids 23-113 of SEQ ID NO:10; to amino acids 24-114 of SEQ ID NO:12; to amino acids 24-114 of SEQ ID NO:14; to amino acids 54-144 of SEQ ID NO:16, to amino acids 19-109 of SEQ ID NO:18, to amino acids 15-105 of SEQ ID NO:20, or to amino acids 18-108 of SEQ ID NO:22. In additional examples, an isolated or recombinant nucleic acid molecules that include a nucleic acid sequence encoding a polypeptide, such as a HAP3-like protein, having at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, or SEQ ID NO:22, in which the polypeptide includes a HAP3-like protein B domain having at least 95%, at least 96%, at least 97%, at least 98%, or at least 99% identity to SEQ ID NO:4, to amino acids 58-148 of SEQ ID NO:8; to amino acids 23-113 of SEQ ID NO:10; to amino acids 24-114 of SEQ ID NO:12; to amino acids 24-114 of SEQ ID NO:14; to amino acids 54-144 of SEQ ID NO:16, to amino acids 19-109 of SEQ ID NO:18, to amino acids 15-105 of SEQ ID NO:20, or to amino acids 18-108 of SEQ ID NO:22. The HAP3-like protein B domain can be an non-LEC1-type HAP3-like protein B domain and can comprise the amino acid sequence of SEQ ID NO:2 or SEQ ID NO:3.

At the nucleotide level, a nucleic acid molecule as provided herein can in some examples share at least about 30%, 35%, 40%, or 45% nucleotide sequence identity, and in some examples at least about 50%, at least about 55%, at least about 60%, at least about 65%, at least about 70%, at least about 75%, or at least about 80% sequence identity, for example at least about 85%, at least about 90%, at least about 95% or at least about 97% sequence identity, to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:33, SEQ ID NO:35, SEQ ID NO:37, SEQ ID NO:39, SEQ ID NO:49, and SEQ ID NO:51, or to a region or fragment of any of the listed sequences. For example, a nucleic acid molecule as provided herein can in some examples have at least 50%, at least 55%, at least 60%, at least 65%, at least 70%, at least 75%, or at least 80% sequence identity, for example at least 85%, at least 90%, at least 95%, or at least 97% sequence identity to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21. In further examples, a nucleic acid molecule as provided herein can have at least 85%, at least 90%, at least 95%, or at least 97% sequence identity to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:33, SEQ ID NO:35, SEQ ID NO:37, SEQ ID NO:39, SEQ ID NO:49, and SEQ ID NO:51 or a complement of any thereof, thereof, including a complement of a portion of any of the foregoing sequences that can be provided, for example, in an RNAi or antisense RNA construct.

In various examples, the nucleic acid molecules disclosed herein comprise a nucleic acid sequence that encodes a HapY polypeptide, that is, a, non-LEC1-type HAP3 polypeptide having at least 65% sequence identity to a naturally-occurring polypeptide of an algal or heterokont species, for example, at least 85% sequence identity to a naturally-occurring polypeptide of an algal or heterokont species.

Alternatively or in addition to a non-LEC1-t e HAP3 (NF-YB) polypeptide as provided herein, a nucleic acid molecule can encode a NF-YC polypeptide and/or a NF-YA polypeptide. Without limiting the invention to any particular mechanism, an NF-YB polypeptide can be functional in the cell as part of a complex that includes an NFY-C polypeptide and/or an NF-YA polypeptide. As demonstrated in Examples 9 and 10, the inventors have isolated NF-YC and NF-YA polypeptides that interact with the Nannochloropsis NF-YB polypeptide (referred to herein as HAP-Y, a non-LEC1-type HAP3 polypeptide). Nucleic acid molecules encoding NF-YC and NF-YA polypeptides as disclosed herein can also be expressed in microorganisms for enhancing growth rates and/or productivity.

For example, provided herein are nucleic acid molecules that encode a polypeptide having at least 65%, at least 70%, at least 75%, or at least 80% sequence identity, for example at least 85%, at least 90%, at least 95%, at least 96%, or at least 97%, at least 98%, at least 99%, or 100% identity to SEQ ID NO:64, SEQ ID NO:65, SEQ ID NO:66, or SEQ ID NO:68. The polypeptide can be a NF-YC polypeptide. The nucleic acid molecules can have, in some examples, at least 50%, at least 55%, at least 60%, at least 65%, at least 70%, at least 75%, or at least 80% sequence identity, for example at least 85%, at least 90%, at least 95%, or at least 97% sequence identity to SEQ ID NO:63.

In additional examples, provided herein are nucleic acid molecules that encode a polypeptide having at least 65%, at least 70%, at least 75%, or at least 80% sequence identity, for example at least 85%, at least 90%, at least 95%, at least 96%, or at least 97%, at least 98%, at least 99%, or 100% identity to SEQ ID NO:70. The polypeptide can be a NF-YA polypeptide. The nucleic acid molecule can have, in some examples, at least 50%, at least 55%, at least 60%, at least 65%, at least 70%, at least 75%, or at least 80% sequence identity, for example at least 85%, at least 90%, at least 95%, or at least 97% sequence identity to SEQ ID NO:69.

An isolated or recombinant nucleic acid molecule as provided herein can in some examples have a nucleotide sequence that is different from (i.e., not 100% identical to) a nucleotide sequence of a naturally-occurring gene and/or the isolated or recombinant nucleic acid molecule can be a cDNA. For example, an isolated or recombinant nucleic acid molecule as provided herein can include a protein-encoding region that lacks one or more intervening non-coding sequences (introns) that are found in the genome of the organism that includes the gene, and can include two or more protein-encoding sequences of the gene that are continuous, where the two or more sequences are separated by introns in the unaltered genome of an organism. For example, the nucleic acid molecule can comprise a cDNA, in which the cDNA comprises a different sequence than is found in the genome of a naturally-occurring organism. Alternatively or in addition, the nucleic acid molecule can comprise a protein-encoding gene that includes a 5' untranslated region that is not contiguous with the protein-encoding portion of the nucleic acid molecule in the genome of a non-genetically modified organism. Alternatively or in addition to any of the above, the nucleic acid molecule can have a sequence that has one or more nucleobase changes with respect to the sequence of a naturally-occurring gene in the genome of an organism. For example, the nucleic acid molecule can have a sequence that has one or more nucleobase substitutions, deletions, or additions with respect to the sequence of a naturally-occurring gene in the genome of an organism.

Additionally, an isolated or recombinant nucleic acid molecule as provided herein, when expressed in a microbial host cell, can confer higher productivity on the microbial host cell. In some examples, expression of a nucleic acid molecule as disclosed herein in a microalgal or heterokont cell can result in the microalgal or heterokont cell having higher productivity when compared with a control cell that does not express the nucleic acid molecule, for example, the microbial host cell can demonstrate a higher growth rate, greater biomass productivity, or higher rate or level of production of a biomolecule such as, for example, a lipid, protein, pigment, or carbohydrate, including an alcohol. For example, the host cell can exhibit higher productivity with respect to a control cell of one or more products the host cell is engineered to synthesize.

An isolated nucleic acid molecule of the present invention can be produced using recombinant DNA technology (e.g., any or a combination of any of reverse transcription, restriction, ligation, polymerase reactions, including polymerase chain reaction (PCR) amplification, cloning, in vitro or in vivo recombination, etc.) or chemical synthesis. Isolated nucleic acid molecules include natural nucleic acid molecules and homologs thereof, including, but not limited to, natural allelic variants and modified nucleic acid molecules in which nucleotides have been inserted, deleted, and/or substituted, in such a manner that such modifications provide the desired effect on the biological activity of CCAAT-box binding factors as described herein.

A nucleic acid molecule variant can be produced using a number of methods known to those skilled in the art (see, for example, Sambrook et al. *Molecular Cloning: A Laboratory Manual*. 2nd ed. N.Y., Cold Spring Harbor Laboratory, Cold Spring Harbor Laboratory Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules, and combinations thereof. Nucleic acid molecule homologs can be selected from a mixture of modified nucleic acids by screening for the function of the protein encoded by the nucleic acid and/or by hybridization with a wild-type gene.

According to some embodiments of the present application, nucleic acid molecules of the present invention will include those nucleic acid molecules that specifically hybridize to one or more of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:33, SEQ ID NO:35, SEQ ID NO:37, SEQ ID NO:39, SEQ ID NO:49, and SEQ ID NO:51, fragments thereof, and complements thereof and their fragments, under moderate or high stringency conditions. In particular examples, nucleic acid molecules of the present invention can comprise a nucleic acid sequence that hybridizes, under high stringency conditions, to a nucleic acid sequence selected from the group consisting of SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:21, a complement thereof, or a fragment of either.

As used herein, two nucleic acid molecules are said to be capable of specifically hybridizing to one another if the two molecules are capable of forming an anti-parallel, double-stranded nucleic acid structure. Two molecules are said to be minimally complementary if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. A nucleic acid molecule is said to be the complement of another nucleic acid molecule if they exhibit complete complementarity. As used herein, molecules are said to exhibit complete complementarity when every nucleotide of one of the molecules is complementary to a nucleotide of the other. Departures from complete complementarity are permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Conventional stringency conditions are described by Sambrook et al., supra, and by Haymes et al. In: *Nucleic Acid Hybridization, A Practical Approach*, IRL Press, Washington, D.C. (1985). For example, appropriate stringency conditions which promote DNA hybridization include, for example, 6.0× sodium chloride/sodium citrate (SSC) at about 45° C., followed by a wash of 2.0×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These and other conditions are known to those skilled in the art, or can be found in *Current Protocols in Molecular Biology*, John Wiley & Sons, N.Y. (1989), 6.3.1-6.3.6. Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70×C for several hours to overnight. High stringency conditions are preferably provided by 6×SSC, 5×Denhardt's solution, 100 mg/mL fish sperm DNA, and 0.1% (w/v) SDS, with incubation at 55° C. for several hours. Hybridization is generally followed by several wash steps. The wash compositions generally comprise 0.5× to about 10×SSC, and 0.01% (w/v) to about 0.5% (w/v) SDS with a 15 min incubation at about 20° C. to about 70° C. Preferably, the nucleic acid segments remain hybridized after washing at least one time in 0.1×SSC at 65° C.

A subset of the nucleic acid molecules of this invention includes fragments of the disclosed polynucleotides consisting of oligonucleotides of at least 12, at least 15, for example at least 16 or 17, or for example at least 18 or 19, such as at least 20 or more, consecutive nucleotides. Such oligonucleotides are fragments of the larger molecules having a sequence selected from the polynucleotide sequences in the Sequence Listing, and find use, for example, as interfering molecules, probes and primers for detection of the polynucleotides of the present invention.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of a polypeptide according to the present invention, e.g. HapY and other HAP3-like proteins disclosed herein. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a HapY or HAP3-like polypeptide, an entire HapY or HAP3-like polypeptide, or several domains within an open reading frame encoding a HapY or HAP3-like polypeptide.

The present invention provides, in various examples, nucleotide sequences comprising regions that encode polypeptides that may be the complete protein encoded by the gene represented by the polynucleotide, or may be fragments of the encoded protein. For example, polynucleotides provided herein can encode polypeptides constituting a substantial portion of the complete protein, for example, constituting a sufficient portion of the complete protein to provide the relevant biological activity, e.g., the activity of a HapY or HAP3 subunit of a CCAAT-box transcription factor. Of particular interest are polynucleotides of the present invention that encode a HAP3-like polypeptide. Such polynucleotides may be expressed in transgenic cells or transgenic organisms to produce cells and organisms having higher productivity, for example, higher biomass productivity.

Nucleic acid molecules that are fragments of these HAP3-like or HapY-encoding nucleotide sequences are also encompassed by the present invention. A "HapY fragment" or "HAP3-like fragment", as used herein, is intended to be a portion of the nucleotide sequence encoding a HapY or HAP3-like polypeptide. A fragment of a nucleotide sequence may encode a biologically active portion of a HapY or HAP3-like polypeptide, or it may be a fragment that can be used as a hybridization probe or PCR primer using methods disclosed below. A nucleic acid molecule as provided herein can be a fragment of the disclosed polynucleotides consisting of oligonucleotides of at least 12, at least 15, at least 20, at least 50, at least 100, at least 200, at least 500, or at least 1000 contiguous nucleotides, or up to the number of nucleotides present in a full-length HapY or HAP3-like protein-encoding nucleotide sequence disclosed herein. For example, nucleic acid molecules that are fragments of a HAP3-like nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length HapY or HAP3-like protein-encoding nucleotide sequence disclosed herein (e.g., SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:33, SEQ ID NO:35, SEQ ID NO:37, SEQ ID NO:39, SEQ ID NO:49, or SEQ ID NO:51) depending upon the intended use. In some examples, a HapY or HAP3-like fragment encoded by a nucleic acid sequence as provided herein may have an N-terminal or a C-terminal truncation of at least about 100 amino acids, about 120, about 130, about 140, about 150, or about 160 amino acids relative to any of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:32, SEQ ID NO:34, SEQ ID NO:36, SEQ ID NO:38, SEQ ID NO:50, and SEQ ID NO:52.

Fragments of the nucleotide sequences of the present invention include those that encode protein fragments that retain the biological activity of a HAP3-like protein. By "retains activity" is intended that the fragment will have at least about 30%, at least about 50%, at least about 70%, 80%, 90%, 95% or higher of the HapY polypeptide activity. Methods for measuring activity of HAP3-like polypeptides are well known in the art and have been extensively documented. For example, the DNA binding activity of a HAP3-like polypeptide to a CCAAT-box target nucleotide sequence, including an inverted CCAAT-box target nucleotide sequence can be determined by in vitro electrophoretic gel mobility shift assay (EMSA) (see, e.g., Ohga et al., *J. Biol. Chem.*, 273:5997-6000, 1998; Ise et al., *Cancer Res.* 59, 342-346, 15, 1999; and Butler et al., PNAS Vol. 99 no. 18 11700-11705, 2002); or DNA footprint analyses (see, e.g., Kato et al., *Mol. Gen. Genet.*, 257, 404-411, 1998; Morgan et al., *Mol. Cell. Biol*. Vol. 7 No. 3 1129-1138, 1987). Other examples of techniques that can be used in measuring biological activity of a HAP3-like polypeptide include yeast two-hybrid system and co-immunoprecipitation, both of which can be used to assess the ability of a HAPY polypeptide to interact with the other subunits of a CCAAT-box binding complex as described in, for example, McNabb et al., *Genes Dev.* 9: 47-58, 1995; Calvenzani et al., *PLoS ONE* 7(8): e42902, 2012; Zhu et al., *J Biol. Chem.* 279, 29902-29910, 2004; and Hackenberg et al., *Mol. Plant* 5 (4): 876-888, 2012.

Further, a nucleic acid molecule as provided herein, including a nucleic acid molecule that includes sequences that encode fragments of a HapY or HAP3-like polypeptide, can be expressed in a recombinant host cell and the effects of expression of the nucleic acid molecule on the organism's productivity can be assayed. Productivity can be measured, for example, by growth assays (e.g., monitoring propagation by cell counts or optical density), by determining total organic carbon (TOC) of ash-free dry weight accumulated over time, or by assessing the amount of any product of interest, for example, proteins, carbohydrates, lipids, pigments, etc. using methods used in the art, including without limitation, gas chromatography (GC), HPLC, immunological detection, biochemical and/or enzymatic detection, etc.

Also of interest in the present invention are variants of the polynucleotides provided herein. Such variants may be naturally-occurring, including homologous polynucleotides from the same or a different species, or may be non-natural variants, for example polynucleotides synthesized using chemical synthesis methods, or generated using recombinant DNA techniques. With respect to nucleotide sequences, degeneracy of the genetic code provides the possibility to substitute at least one base of the protein encoding sequence of a gene with a different base without causing the amino acid sequence of the polypeptide produced from the gene to be changed. Hence, the DNA of the present invention may also have any base sequence that has been changed from any polynucleotide sequence in the Sequence Listing by substitution in accordance with degeneracy of the genetic code. References describing codon usage are readily available.

In addition, the skilled artisan will further appreciate that changes can be introduced by mutation of the nucleotide sequences of the invention, thereby leading to changes in the amino acid sequence of the encoded HapY or HAP3-like proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted nonessential amino acid residues. A "nonessential" amino acid residue, as used herein, is a residue that can be altered from the wild-type sequence of a presently disclosed HapY protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In a particular non-limiting exemplification, conserved residues, domains and motifs of HapY proteins and other HAP3 homologs are indicated in FIG. 1 and FIG. 2 and can be recognized in the sequences of the Sequence Listing. As discussed above, it will be appreciated by one skilled in the art that amino acid substitutions may be made in non-conserved regions that retain the function of the polypeptide. In general, such substitutions would not be made for conserved amino acid residues, or for amino acid residues residing within a conserved motif, where such residues may be essential for protein activity. Examples of residues that are conserved and that may be essential for protein activity include, for example, residues that are identical between all proteins contained in an alignment of the amino acid sequences of the present invention and known HAP3-like protein sequences. Examples of residues that are conserved but that may allow conservative amino acid substitutions and still retain activity include, for example, residues that have only conservative substitutions between all proteins contained in an alignment of the amino acid sequences of the present invention and known HAP3-like sequences. However, one of skill in the art would understand that functional variants may have minor conserved or non-conserved alterations in the conserved residues.

HapY variants include proteins having an amino acid sequence that differs from any one of the polypeptides in the Sequence Listing (e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, and SEQ ID NO:52), by at least one amino acid deletion, insertion, or substitution at one or more of the positions corresponding to the conserved amino acid residues as identified in FIG. 1, and combinations of any thereof. In some preferred embodiments, such HapY variants include proteins having an amino acid sequence that differs from any one of the polypeptides in the Sequence Listing, by an amino acid deletion, insertion, or substitution at one or more of the positions corresponding to the conserved amino acid residues as identified in FIG. 1, and combinations of any thereof.

Alternatively or in addition, variant nucleotide sequences can be made by introducing mutations randomly along all or part of the coding sequence, such as by saturation mutagenesis, and the resultant mutants can subsequently be screened for ability to confer activity of an HAP3-like protein in order to identify mutants that retain HAP3-like or HapY protein activity. For example, following mutagenesis, the encoded protein can be expressed recombinantly, and the activity of the protein can be determined using standard assay techniques as disclosed hereinabove.

Methods for such manipulations are known in the art. For example, amino acid sequence variants of a HAP3-like or HapY protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired HAP3-like or HapY activity. However, it is understood that the ability of a HAP3-like or HapY polypeptide to confer an increase in productivity may be improved by the use of such techniques upon the compositions of this invention. For example, one may express a HAP3-like or HapY polypeptide in host cells that exhibit high rates of base-misincorporation during DNA replication, such as Stratagene XL-1 Red cell (Fischer Scientific). After propagation in such strains or cells, one can isolate the HAP3-like protein or HapY encoding DNA (for example by preparing plasmid DNA, or by amplifying by PCR and cloning the resulting PCR fragment into a vector), followed by culture the mutated HAP3-like protein or HapY genes in a non-mutagenic strain or cell, and identify mutated HAP3-like protein or HapY genes with an ability to increase host cell productivity, for example by performing an assay to test for HAP3-like protein or HapY activity in vivo and in vitro.

Alternatively or in addition, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Domain swapping or shuffling is another mechanism for generating altered HAP3-like or HapY proteins. Conversed domains may be swapped between HAP3-like or HapY proteins, resulting in hybrid or chimeric HAP3-like or HapY polypeptides with improved biomass productivity. Methods for generating recombinant proteins and testing them for improved biomass productivity are known in the art. Accordingly, the molecules of the present invention also include fusions between two or more HAP3-like or HapY genes or polypeptides. Different domains of different genes or polypeptides can be fused. HAP3-like or HapY gene fusions can be linked directly or can be attached by additional amino acids that link the two of more fusion partners.

Gene fusions can be generated by basic recombinant DNA techniques, examples of which are described below herein. Selection of gene fusions will depend on the desired phenotype caused by the gene fusion. For instance, if phenotypes associated with the A domain of one HAP3-like protein or HapY protein are desired with phenotypes associated with the B domain of a second HAP3-like or HapY protein, a fusion of the first HAP3-like or HapY protein's A domain to the second HAP3-like or HapY's B domain would be created. The fusion can subsequently be tested in vitro or in vivo for the desired phenotypes.

HAP3-like or HapY polypeptides are also encompassed within the present invention. In an embodiment of this aspect, by "HapY polypeptide" is intended a polypeptide having an amino acid sequence comprising any one of the amino acid sequences in the Sequence Listing (e.g., SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, and SEQ ID NO:52), or variants threof. Fragments, biologically active portions, and variants thereof are also provided, and may be used to practice the methods of the present invention.

Altered or improved variants: It is contemplated that DNA sequences of a HapY or other HAP3/NF-YB homologs of a CCAAT-box transcription factor may be altered by various methods, and that these alterations may result in DNA sequences encoding proteins with amino acid sequences different than that encoded by a HapY gene of the present invention. The HAP3-like or HapY protein may be altered in various ways including amino acid substitutions, deletions, truncations, and insertions of one or more amino acids of the polypeptide sequences set forth in the Sequence Listing, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Also considered are polypeptides having at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, and SEQ ID NO:52, or to a fragment or conserved domain thereof as indicated in Table 1, such as a DNA-binding domain, a subunit interaction domain, or a B domain. The polypeptides will preferably be biologically active with respect to either a structural attribute, such as the capacity of a polypeptide to be bound by an antibody or to bind to a target nucleotide sequence (or to compete with another molecule for such binding). Alternatively or in addition, such an attribute may be catalytic and thus involve the capacity of the molecule to mediate a chemical reaction (for an enzymatic protein) or transcriptional regulation response (for a transcription factor). The polypeptides and polypeptides of the present invention may also be recombinant.

In general, the biological activity or biological action of a protein or domain refers to any function(s) exhibited or performed by the protein or domain that is ascribed to the naturally-occurring form of the protein as measured or observed in vivo (i.e., in the natural physiological environment of the protein) or in vitro (i.e., under laboratory conditions). As used herein, a functional domain of a HapY polypeptide is a domain that is capable of performing a biological function of a HapY polypeptide. For example, a biological activity of a HapY polypeptide and the individual domains that make up a HapY polypeptide includes the B domain, the DNA-binding domain, the subunit interaction domain, the amino terminal A domain, and the carboxyl terminal C domain, which have been discussed in detail elsewhere herein.

Any of a variety of methods well known in the art may be used to make or to obtain one or more of the above-described polypeptides. The polypeptides of the invention can be chemically synthesized or polypeptides can be made using standard recombinant techniques in heterologous expression systems such as E. coli, yeast, insects, etc. Antibodies to the polypeptides of the present invention, or to variants or fragments thereof, are also encompassed. A variety of techniques and methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265), and can be used to make an antibody according to the invention disclosed herein.

Nucleic Acid Constructs

Another aspect of the present invention relates to recombinant nucleic acid molecules comprising a nucleic acid sequence encoding an amino acid sequence having a biological activity of at least one domain of a HAP3-like or HapY polypeptide as described herein. Typically, such a recombinant nucleic acid molecule includes at least one nucleic acid molecule of the present invention operably linked to one or more transcription control sequences. As used herein, the phrase "recombinant molecule" or "recombinant nucleic acid molecule" primarily refers to a nucleic acid molecule or nucleic acid sequence operably linked to a transcription control sequence, but can be used interchangeably with the phrase "nucleic acid molecule", when such nucleic acid molecule is a recombinant molecule as discussed herein.

The invention provides nucleic acid constructs comprising a nucleic acid sequence as provided herein operably linked to one or more sequences that can regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that can be operably linked to a gene of interest or antisense sequence in an expression construct or "expression cassette". Various algal promoters are known and can be used, including those disclosed in U.S. Patent Appl. Pub. No. US 2013/0023035; U.S. patent application Ser. No. 13/486,930, filed Jun. 1, 2012; U.S. patent application Ser. No. 13/693,585, filed Dec. 4, 2012; and U.S. patent application Ser. No. 13/915,522, filed Jun. 11, 2013. A promoter used in a construct may in some instances be regulatable, e.g., inducible.

An inducible promoter can be responsive to, e.g., light intensity or high or low temperature, and/or can be responsive to specific compounds. The inducible promoter may be, for example, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (e.g., U.S. Pat. No. 8,318,482; U.S. Pat. No. 5,750,385; U.S. Pat. No. 5,639,952), metals (*Eukaryotic Cell* 2:995-1002 (2003)) or temperature (U.S. Pat. No. 5,447,858; Abe et al. *Plant Cell Physiol.* 49: 625-632 (2008); Shroda et al. *Plant J.* 21: 121-131 (2000). The foregoing examples are not limiting as to the types of promoters or specific promoters that may be used. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

In aspects where the nucleic acid construct does not contain a promoter in operable linkage with the nucleic acid sequence encoding the gene of interest (e.g., a HapY gene) the nucleic acid sequence can be transformed into the cells such that it becomes operably linked to an endogenous promoter by, e.g., homologous recombination, site specific integration, and/or vector integration. In some instances, genomic host sequences included in a nucleic acid construct for mediating homologous recombination into the host genome may include gene regulatory sequences, for example, a promoter sequence, that can regulate expression of a gene or antisense or RNAi sequence of the nucleic acid construct. In such examples, the transgene(s) of the construct can become operably linked to a promoter that is endogenous to the host microorganism. The endogenous promoter(s) may be regulatable, e.g., inducible.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i. e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell. Yet in other embodiments, a recombinant molecule of the present invention comprises an organelle targeting signal to enable an expressed protein to be transported and delivered to the target cellular organelle. It will be appreciated by one skilled in the art that a variety of organelle targeting signals can be used including, but not limited to, nuclear localization signal (NLS), chloroplast targeting signal, and mitochondria-targeting sequence.

A nucleic acid molecule as described herein can be cloned into suitable vector and can be used to transform or transfect any suitable host. The selection of vectors and methods to construct them are commonly known to the art and are described in general technical references (see, e.g., Sambrook and Russell, *Molecular Cloning, A Laboratory Manual*, Cold Spring Harbor Laboratory Press, 2001). Thus, in some embodiments of the invention, the recombinant nucleic acid molecule is a recombinant vector. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, such as, for example, an origin of replication for propagation of the nucleic acid molecule in a convenient host, such as *E. coli* or yeast, a selectable marker, a reporter gene, expression sequences, etc. The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain one or more selectable genetic markers.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption, modification, or knock-out technology). Such a vector may also be known in the art as a "knock-out" vector. In one aspect of this embodiment, a portion of the vector, which is typically the nucleic acid molecule inserted into the vector (i.e., the insert), has a nucleic acid sequence that is homologous to a nucleic acid sequence of a target gene in the host cell (i.e., a gene which is targeted to be modified, deleted, or inactivated). The nucleic acid sequence of the vector insert is designed to bind to the target gene such that the target gene and the insert undergo homologous recombination, whereby the endogenous target gene is modified, deleted, inactivated or attenuated (i.e., by at least a portion of the endogenous target gene being mutated or deleted).

Constructs for homologous recombination into an algal or heterokont genome (e.g., for disruption or gene replacement of a regulator gene) can include a nucleotide sequence of a HapY gene or ortholog, such as for example any provided herein, or sequences from the algal or heterokont genome that are adjacent to the HapY gene in the host organism. For example, a construct for homologous recombination can include at least 50, at least 100, at least 200, at least 300, at least 400, at least 500; at least 600, at least 700, at least 800, at least 900, at least 1,000, at least 1,200, at least 1,500, at least 1,750, or at least 2,000 nucleotides of a gene targeted for knock-out or gene replacement such as a HapY gene or ortholog, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a HapY polypeptide, wherein the HapY polypeptide comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to any one of the amino acid sequences in the Sequence Listing. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of any one of the nucleic acid sequences in the Sequence Listing, and/or an adjacent region of the corresponding genome.

For example, the sequences for mediating homologous recombination in a construct can include one or more nucleotide sequences from or adjacent to a naturally-occurring algal or heterokont gene encoding a HapY polypeptide, wherein the HapY polypeptide comprises an amino acid sequence having at least 80%, for example, at least 85%, at least 90%, at least 95% identity, or at least 99% to any one of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, and SEQ ID NO:52. For example, a construct for homologous recombination can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of a regulator gene that encodes a HapY polypeptide, such as any disclosed herein, and/or genomic DNA adjacent thereto. For example, the sequences for mediating homologous recombination in a construct can include one or more nucleotide sequences from or adjacent to a naturally-occurring algal or heterokont gene encoding a HAP3-like B domain-containing protein, wherein the HAP3-like B domain-containing protein comprises an amino acid sequence having at least 40%, for example, at least 45%, at least 50%, at least 55%, at least 60%, at least 65%, at least 70%, at least 75%, at least 80%, at least 85%, at least 90%, at least 95%, or at least 99% identity to any one of the B domains of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:34, SEQ ID NO:36, SEQ ID NO:38, SEQ ID NO:40, SEQ ID NO:50, and SEQ ID NO:52. In exemplary embodiments, the construct can include at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides of any one of the nucleic acid sequences encoding a HAP3-like B domain indicated in the Sequence Listing and/or an adjacent region of the corresponding genome.

General discussion above with regard to recombinant nucleic acid molecules and transformation of host cells is intended to be applied to any recombinant nucleic acid molecule discussed herein, including those encoding any amino acid sequence having a biological activity of at least one domain from a HapY polypeptide, those encoding amino acid sequences from other HapY polypeptides, and those encoding other proteins or domains.

Information in the Sequence Listing

This specification contains nucleotide and polypeptide sequence information prepared using the program PatentIn Version 3.5. The amino acid sequences provided in the Sequence Listing are annotated to indicate one or several known homologs of the respective sequences. Some sequences contain "Pfam" domains which are indicative of particular functions and/or applications. The specific Pfam domains are described in more detail by various sources, such as "www.sanger.ac.uk" or "pfam.janelia.org". Thus, various practical applications of the amino acid sequences in the sequence listing are immediately apparent to those of skill in the art based on their similarity to known sequences.

The amino acid sequences provided in the Sequence Listing are also annotated to indicate one or several known homologs of the respective sequences. Some amino acid sequences contain conserved domains which are indicative of CCAAT-box binding factor activity. The conserved domains indicative of CCAAT-box binding factor activity that Applicants have identified in the polypeptides described herein include the B domain, the Pfam histone-like transcription factor (CBF/NF-Y) domain (Pfam ID: PF00808), and the Pfam core histone H2A/H2B/H3/H4 (Pfam Id: PF00125) domain.

Additional information of sequence applications comes from similarity to sequences in public databases. Entries in the "miscellaneous features" sections of the Sequence Listing labeled "NCBI GI:" and "NCBI Desc:" provide additional information regarding the respective homologous sequences. In some cases, the corresponding public records, which may be retrieved from www.ncbi.nlm.nih.gov, cite publications with data indicative of uses of the annotated sequences. The sequence descriptions and the Sequence Listing attached hereto comply with the rules governing nucleotide and/or amino acid sequences disclosures in patent application as set forth in 37 C.F.R. §1.182-1.185.

Table 1 lists the polypeptides that are described herein, as well as the identifiers of the polypeptides, the conserved domains identified in each of the polypeptides, and the Start and End positions of the amino acid residues representing the conserved domains.

existing library of chromosomal DNA for clones likely to contain DNA adjacent to the novel polynucleotide sequence of interest. Alternatively or in addition, one may clone and sequence regions flanking a known DNA by inverse PCR (Sambrook et al., 1989, supra). Another such method involves ligating linkers of known sequence to chromosomal DNA digested with restriction enzymes, then generating PCR product using an oligonucleotide homologous to the primer linker, and a primer homologous to the region of interest (e.g. the end sequence of a novel polynucleotide sequence of the invention). A kit for performing this procedure (GENOMEWALKER™, Clonetech) is available commercially.

In a hybridization procedure, all or part of a presently disclosed HapY-encoding nucleotide sequence can be used to screen cDNA or genomic libraries. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a

TABLE 1

HAP3-like Polypeptides.

| Source Organism | Seq ID No. | Conserved Domains | START-END of conserved domains |
|---|---|---|---|
| Nannochloropsis gaditana | 6 | PF00125; PF00808; B | 28-91; 27-91; 22-112 (SEQ ID NO: 4) |
| Nannochloropsis_oceanica | 8 | PF00125; PF00808; B | 64-127; 63-127; 27-117 |
| Tetraselmis sp. | 10 | PF00125; PF00808; B | 27-92; 28-92; 23-113 |
| Tetraselmis sp. | 12 | PF00125; PF00808; B | 28-93; 29-93; 24-114 |
| Tetraselmis sp. | 14 | PF00125; PF00808; B | 28-93; 29-93; 24-114 |
| Cyclotella sp. | 16 | PF00125; PF00808; B | 59-123; 58-123; 54-144 |
| Navicula sp. | 18 | PF00125; PF00808; B | 25-88; 24-88; 19-109 |
| Chlorella sp. | 20 | PF00125; PF00808; B | 21-84; 20-84; 15-105 |
| Botryococcus brauniii | 22 | PF00125; PF00808; B | 23-87; 23-87; 18-108 |
| Flagilariopsis cylindrus | 24 | PF00125; PF00808; B | 31-95; 31-95; 26-116 |
| Fragaria vesca | 26 | PF00125; PF00808; B | 33-98; 33-98; 29-119 |
| Fragaria vesca | 28 | PF00125; PF00808; B | 32-95; 31-95; 26-116 |
| Fragaria vesca | 30 | PF00125; PF00808; B | 27-92; 28-9223-113 |
| Fragaria vesca | 32 | PF00125; PF00808; B | 30-95; 31-95; 26-116 |
| Phaeodactylum tricornutum | 34 | PF00125; PF00808; B | 26-89; 25-89; 20-110 |
| Volvox carteri | 36 | PF00125; PF00808; B | 24-85; 21-85; 16-106 |
| Micromonas pusilla | 38 | PF00125; PF00808; B | 28-93; 29-93; 24-114 |
| Micromonas sp. | 40 | PF00125; PF00808; B | 25-90; 26-90; 21-111 |
| Arabidopsis thaliana | 42 | PF00125; PF00808; B | 33-98; 34-98; 29-119 |
| Arabidopsis lyrata | 44 | PF00125; PF00808; B | 26-89; 25-89; 20-110 |
| Arabidopsis lyrata | 46 | PF00125; PF00808; B | 19-89; 25-89; 20-110 |
| Arabidopsis thaliana | 48 | PF00125; PF00808; B | 62-127; 61-127; 58-148 |
| Schizochytrium aggregatum | 50 | PF00125; PF00808; B | 11-75; 10-75; 6-96 |
| Aplanochytrium sp. | 52 | PF00125; PF00808; B | 21-85; 20-85; 16-106 |

From the disclosure of the Sequence Listing and Table 1, it can be seen that the nucleotides and polypeptides of the inventions are useful, depending upon the respective individual sequence, to make transgenic organisms having one or more altered growth and phenotype characteristics such as, for example, increased productivity, for example, increased biomass productivity. The present invention further encompasses nucleotides that encode the above described polypeptides, such as those included in the Sequence Listing, as well as the complements and/or fragments thereof, and include alternatives thereof based upon the degeneracy of the genetic code.

Use of the Nucleic Acid Molecules of the Invention

In one aspect of the invention, one may use one of many known methods to identify DNA sequences adjacent to polynucleotide sequences of interest, such as genomic regions that naturally surround a novel polynucleotide sequence in microbial cell or plant cell. One may accomplish this by generating hybridization probes and screening an fluorescent compound, an enzyme, or an enzyme co-factor. Probes for hybridization can be made by labeling synthetic oligonucleotides based on the known HAP3-encoding nucleotide sequence disclosed herein. Degenerate primers designed on the basis of conserved nucleotides or amino acid residues in the nucleotide sequence or encoded amino acid sequence can optionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of HAP3-encoding nucleotide sequence of the invention or a fragment or variant thereof. Methods for the preparation of probes for hybridization are generally known in the art and are disclosed in Sambrook and Russell (2001, supra) herein incorporated by reference.

Recombinant Microorganism

The invention also provides a recombinant microorganism that includes a non-native gene that encodes a HAP3- like protein, in which the recombinant microorganism has higher productivity than does a control microorganism substantially identical to the recombinant microorganism except that the control microorganism does not have a non-native gene encoding a HAP3-like protein. A HAP3-like protein can be any HAP3 like protein, such as, for example, a non-LEC1-type HAP3-like protein, including a non-LEC1-type HAP3-like protein whose sequence is available from gene, protein, or genome databases or scientific literature, or a variant thereof. A recombinant microorganism as provided herein can in some examples include a non-LEC1-type HAP3-like protein as provided herein, for example, can include any of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:50, or SEQ ID NO:52, a functional fragment of any thereof, or a variant of any thereof.

In various examples, a recombinant microorganism as provided herein includes a non-native gene that encodes a polypeptide having an amino acid sequence with at least 65%, at least 70%, at least 75%, at least 80%, at least 85%, at least 90%, at least 95%, at least 96%, at least 97%, at least 98%, or at least 99% identity to a HAP3-like protein B domain selected from the group consisting of: SEQ ID NO:4, amino acids 58-148 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 26-116 of SEQ ID NO:34, amino acids 20-110 of SEQ ID NO:36, amino acids 16-106 of SEQ ID NO:38, amino acids 24-114 of SEQ ID NO:38, amino acids 21-111 of SEQ ID NO:40, amino acids 29-119 of SEQ ID NO:42, amino acids 20-110 of SEQ ID NO:44, amino acids 20-110 of SEQ ID NO:46, amino acids 58-148 of SEQ ID NO:48, amino acids 6-96 of SEQ ID NO:50, and amino acids 16-106 of SEQ ID NO:52. The polypeptide encoded by the non-native gene is preferably a HAP3-like protein, such as a polypeptide having at least 50% identity to a naturally-occurring HAP3-like protein of a plant or microorganism. The polypeptide can have, for example, at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:50, or SEQ ID NO:52. In some examples, the non-native gene encodes a polypeptide having a HAP3-like protein B domain in which the polypeptide has at least 50%, at least 55%, at least 60%, at least 65%, at least 70%, at least 75%, at least 80%, at least 85%, at least 90%, at least 95%, at least 96%, at least 97%, at least 98%, or at least 99% identity to a HAP3-like polypeptide of a microalgal or heterokont species. The recombinant microorganism can exhibit higher productivity than is exhibited by a control microorganism substantially identical to the recombinant microorganism that includes the non-native gene encoding a polypeptide having a HAP3-like protein B domain, with the exception that the control microorganism does not include a non-native gene encoding a polypeptide having a HAP3-like protein B domain. For example, expression of the non-native gene in an algal or heterokont cell can result in the algal or heterokont cell producing a greater amount of biomass or a greater amount of one or more biomolecules, such as, without limitation, a lipid, a terpenoid, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant.

A recombinant microorganism having a non-native gene encoding a polypeptide having a HAP3-like protein B domain can comprise, e.g., any of the nucleic acid molecules described herein that encode a polypeptide that includes a HAP3-like B domain. Further, the recombinant host cells may comprise any of the constructs or vectors described herein. In some aspects, the nucleic acid sequence encoding the polypeptide can be heterologous with respect to the recombinant host cell, and can be a gene encoding a HAP3-like polypeptide derived from any species, including a plant, animal, or microbial species, or a variant thereof. Alternatively, the gene encoding a HAP3-like polypeptide may be homologous with respect to the host organism. For example, the non-native HAP3-like gene may be a HAP3 gene of the same species as the host microorganism and is introduced into the recombinant microorganism in an expression cassette that allows regulated expression or overexpression of the introduced homologous HAP3 gene. Alternatively, the HAP3-like non-native gene may be endogenous to the microorganism and a heterologous promoter may be introduced into the host microorganism such that it becomes juxtaposed with and operably linked to the endogenous HAP3 gene to effect overexpression and/or regulated expression.

In further examples, a recombinant microorganism as provided herein can include a non-native gene that encodes a polypeptide having a HAP3-like protein B domain, such as a non-LEC1-typye HAP3-like protein B domain having at least 85%, at least 90%, at least 95%, at least 96%, at least 97%, at least 98%, or at least 99% identity to any of the following: SEQ ID NO:2, amino acids 58-148 of SEQ ID NO:6; amino acids 23-113 of SEQ ID NO:8; amino acids 24-114 of SEQ ID NO:10; amino acids 24-114 of SEQ ID NO:12; amino acids 54-144 of SEQ ID NO:14, amino acids 19-109 of SEQ ID NO:16, amino acids 15-105 of SEQ ID NO:18, amino acids 18-108 of SEQ ID NO:20, amino acids 26-116 of SEQ ID NO:22, amino acids 29-119 of SEQ ID NO:22, amino acids 26-116 of SEQ ID NO:22, amino acids 23-113 of SEQ ID NO:22, amino acids 26-116 of SEQ ID NO:22, amino acids 26-116 of SEQ ID NO:32, amino acids 20-110 of SEQ ID NO:34, amino acids 16-106 of SEQ ID NO:36, amino acids 24-114 of SEQ ID NO:38, amino acids 21-111 of SEQ ID NO:40, amino acids 29-119 of SEQ ID NO:42, amino acids 20-110 of SEQ ID NO:44, amino acids 20-110 of SEQ ID NO:46, amino acids 6-96 of SEQ ID NO:50, and amino acids 16-106 of SEQ ID NO:52. The polypeptide encoded by the non-native gene can have, for example, at least 65%, at least 70%, at least 75%, at least 80%, at least 85%, at least 90%, at least 95%, at least 96%, at least 97%, at least 98%, or at least 99% identity to any of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:50, and SEQ ID NO:52.

For example, a recombinant microorganism as provided herein can include a non-native gene that encodes a polypeptide having a non-LEC1-typye HAP3-like protein B domain having at least 85%, at least 90%, at least 95%, at least 96%, at least 97%, at least 98%, or at least 99% identity to any of the following: SEQ ID NO:4, amino acids 58-148 of SEQ ID NO:6; amino acids 23-113 of SEQ ID NO:8; amino acids 24-114 of SEQ ID NO:10; amino acids 24-114 of SEQ ID NO:12; amino acids 54-144 of SEQ ID NO:14, amino acids 19-109 of SEQ ID NO:16, amino acids 15-105 of SEQ ID NO:18, and amino acids 18-108 of SEQ ID NO:20, where the polypeptide encoded by the non-native gene can have at least 65%, at least 70%, at least 75%, at least 80%, at least 85%, at least 90%, at least 95%, at least 96%, at least 97%, at least 98%, or at least 99% identity to any of SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20.

In particular examples, a recombinant microorganism as provided herein can include a non-native gene that encodes a polypeptide having at least 85%, at least 90%, at least 95%, at least 96%, at least 97%, at least 98%, or at least 99% identity to any of SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20, where the polypeptide includes a non-LEC1-typye HAP3-like protein B domain having at least 85%, at least 90%, at least 95%, at least 96%, at least 97%, at least 98%, or at least 99% identity to SEQ ID NO:4, amino acids 58-148 of SEQ ID NO:6; amino acids 23-113 of SEQ ID NO:8; amino acids 24-114 of SEQ ID NO:10; amino acids 24-114 of SEQ ID NO:12; amino acids 54-144 of SEQ ID NO:14, amino acids 19-109 of SEQ ID NO:16, amino acids 15-105 of SEQ ID NO:18, or amino acids 18-108 of SEQ ID NO:20.

In further examples a recombinant microorganism can include a non-native gene that encodes a polypeptide having at least 65%, at least 70%, at least 75%, at least at least 85%, at least 90%, at least 95%, at least 96%, at least 97%, at least 98%, or at least 99% identity to any of SEQ ID NO:64, SEQ ID NO:65, SEQ ID NO:66, and SEQ ID NO:68. The polypeptide can be a NFY-C polypeptide. In some examples, a recombinant microorganism can include a non-native gene that encodes a non-LEC1-typye HAP3-like protein, such as any disclosed herein, and can further include a non-native gene that encodes a NFY-C polypeptide. A gene encoding an NFY-C polypeptide can be identified in a host microorganism of interest that includes a a non-LEC1-typye HAP3-like protein gene by using methods as provided herein such as yeast two hybrid assays. In yet further examples a recombinant microorganism can include a non-native gene that encodes a polypeptide having at least 65%, at least 70%, at least 75%, at least at least 85%, at least 90%, at least 95%, at least 96%, at least 97%, at least 98%, or at least 99% identity to any of SEQ ID NO:70. The polypeptide can be a NFY-A polypeptide. In some examples, a recombinant microorganism can include a non-native gene that encodes a non-LEC1-typye HAP3-like protein, such as any disclosed herein, and can further include a non-native gene that encodes a NFY-A polypeptide. A gene encoding an NFY-A polypeptide can be identified in a host microorganism of interest that includes a a non-LEC1-typye HAP3-like protein gene by using methods as provided herein such as yeast two hybrid assays.

Recombinant microorganisms as provided herein can in some examples include one or more non-native nucleic acid moecules encoding all three subunits of the HAP heterotrimer (aka CBF or NFY). For example a host microorganism can include a non-native nucleic acid molecule encoding any non-LEC1-type HAP3-like protein as provided herein in addition to a non-native nucleic acid molecule encoding a NFY-C polypeptide as provided herein and a NFY-A polypeptide as provided herein.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes from either the nucleus or the plastid, and in some cases can result in transient expression of transgenes. For example, genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell,* 2010; and Gong et al., *J. Ind. Microbiol. Biotechnol.,* 2011). Non-limiting examples of such useful transformation methods include agitation of cells in the presence of glass beads or silicon carbide whiskers as reported by, for example, Dunahay, *Biotechniques,* 15(3):452-460, 1993; Kindle, *Proc. Natl. Acad. Sci. U.S.A.,* 1990; Michael and Miller, *Plant J.,* 13, 427-435, 1998. Electroporation techniques have been successfully used for genetic transformation of several microalgal species including *Nannochloropsis* sp. (see, e.g., Chen et al., *J Phycol.,* 44:768-76, 2008), *Chlorella* sp. (see, e.g., Chen et al., *Curr. Genet.,* 39:365-370, 2001; Chow and Tung, *Plant Cell Rep.* Vol. 18, No. 9, 778-780, 1999), *Chlamydomonas* (Shimogawara et al., *Genetics,* 148: 1821-1828, 1998), *Dunaliella* (Sun et al., *Mol. Biotechnol.,* 30(3): 185-192, 2005). Microprojectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.,* 252:572-579, 1996), *Cyclotella* and *Navicula* (Dunahay et al., *J. Phycol.,* 31:1004-1012, 1995), *Cylindrotheca* (Fischer et al., *J. Phycol.,* 35:113-120, 1999), and Chaetoceros sp. (Miyagawa-Yamaguchi et aL, *Phycol. Res.* 59: 113-119, 2011), as well as green algal species such as *Chlorella* (El-Sheekh, *Biologia Plantarum,* Vol. 42, No. 2: 209-216, 1999), and *Volvox* species (Jakobiak et al., *Protist,* 155:381-93, 2004). Additionally, *Agrobacterium*-mediated gene transfer techniques can also be useful for genetic transformation of microalgae, as has been reported by, for example, Kumar, *Plant Sci.,* 166(3):731-738, 2004, and Cheney et al., *J. Phycol.,* Vol. 37, Suppl. 11, 2001.

A transformation vector as described herein will typically comprise a marker gene that confers a selectable or scorable phenotype on target host cells, e.g., algal cells. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.,* 19, 353-61, 1999; Lumbreras et al., *Plant J.,* 14(4):441-447, 1998; Zaslayskaia et al., *J Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist,* supra.; Sizova et al., *Gene,* 277:221-229, 2001), nourseothricin (Zaslayskaia et al., 2000, supra), G418 (Dunahay et al., 1995, supra; Poulsen and Kroger, *FEBS Lett.,* 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), β-galactosidase (Gan et al., *J Appl. Phycol.,* 15:345-349, 2003; Jiang et al., *Plant Cell Rep.,* 21:1211-1216, 2003; Qin et al., *High Technol. Lett.,* 13:87-89, 2003), and green fluorescent protein (GFP) (Cheney et al., 2001, supra; Ender et al., *Plant Cell,* 2002, Franklin et al., *Plant J.,* 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate. Additional algal promoters that can find use in the constructs and transformation systems provided herein include those disclosed in U.S. Patent Appl. Pub. No. US 2013/0023035; U.S. patent application Ser. No. 13/486, 930, filed Jun. 1, 2012; U.S. patent application Ser. No. 13/693,585, filed Dec. 4, 2012; and U.S. patent application Ser. No. 13/915,522, filed Jun. 11, 2013.

Host cells can be either untransformed cells or cells that are already transfected with at least one nucleic acid molecule. For example, a host cell that includes a non-native gene as provided herein that encodes a HAPY gene, homolog, or variant can further include one or more genes that may confer any desirable trait, such as, but not limited to, increased production of biomolecules of interest, such as one or more proteins, pigments, alcohols, or lipids. For example, for production of lipid, a host cell (such as but not limited to an algal or heterokont host cell) can optionally include one or more non-native genes encoding polypeptides that functions in lipid biosynthesis, including, but not limited to, polypeptides that encode enzymes for the production of fatty acids, fatty acid derivatives, and/or glycerolipids including, but not limited to, diacylglycerol acyltransferase (DGAT) gene, a glycerolphosphate acyltransferase (GPAT) gene, a lysophosphatidic acid acyltransferase (dehydrogenase) (LPAAT) gene, a phosphatidic acid phosphatase (PAP) gene, and/or a monoacylglycerol acyltransferase (MGAT) gene.

Suitable host cells to be modified using the materials and methods according to the present invention include, but are not limited to, bacteria, protists, microalgae, phytoplankton, heterokonts, fungi, and protozoa. The process can be used, for example, with algal species that are important or interesting for aquaculture, or for the production of biomass used in producing liquid fuel molecules and other chemicals.

Heterokont species considered for use in the invention include, but are not limited to, Bacillariophytes, Eustigmatophytes, Labrinthulids, and Thraustochytrids. In some examples, the strain may be a species of *Labryinthula, Labryinthuloides, Thraustochytrium, Schizochytrium, Aplanochytrium, Aurantiochytrium, Japonochytrium, Diplophrys,* or *Ulkenia.*

Algal species suitable for the method of the invention include microalgae such as, for example, a species of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Cryptheco-dinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseu-*

*dostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.*

In some embodiments of the present application, preferred microorganisms to genetically engineer include, but are not limited to, photosynthetic organisms such as cyanobacteria, algae, diatoms, and the like. Non-limiting examples of exemplary species include, for instance, eustigmatophytes or diatoms such as, for example, a species of *Amphora, Chaetoceros, Cyclotella, Eustigmatos, Fragilaria, Fragilaropsis, Monodus, Nannochloropsis, Navicula, Nitzschia, Pavlova, Phæodactylum, Thalassiosira,* or *Vischeria*. In some embodiments, members of the genus *Nannochloropsis* such as, but are not limited to, *N. gaditana, N. granulata, N. limnetica, N. oceanica, N. oculata,* and *N. salina* are transformed with or overexpress a nucleic acid molecule as provided herein that encodes a HAP3-like or HapY polypeptide.

A microorganism that includes a non-native gene as provided herein can have improved productivity when compared with a control microorganism that does not include the non-native gene encoding a HAP3-like B domain-containing polypeptide. Higher productivity can be demonstrated by measuring growth rates, for example, using a cytometer, or by measuring optical density at wavelengths higher than 700 nm, for example, at 730 or 750 nm. Ash free dry weight can also be measured, as provided in the Examples herein. Production of various biomolecules can be assessed by extraction of algal biomass, partial or substantial purification of the product of the biomolecule of interest, and quantitation of the product by any means known in the art, such as but not limited to, chemical or biochemical analysis, spectroscopic or immunological detection, and/or activity assays.

Methods of Producing Algal Products

Also provided herein are methods of producing biomass or at least one bioproduct by culturing microbial cells having a modulated growth characteristic, such as the host cells disclosed herein. The methods include culturing a microbial cell as disclosed herein that includes a non-native gene encoding a HAP3-like protein, such as a nucleic acid molecule as disclosed herein that encodes a HapY protein or HAP3-like protein, in a suitable medium to provide an algal culture and recovering biomass or at least one bioproduct from the culture. The microorganism in some examples can be a microalga. The algal culture can be a photoautotrophic culture, in which the culture medium preferably does not include a substantial amount of reduced carbon, that is, the culture does not include reduced carbon in a foin or at a level that can be used by the algae for growth.

The algae may be cultured in any suitable vessel, including flasks or bioreactors, where the algae may be exposed to artificial or natural light. The culture comprising algal cells with modulated growth characteristics may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the host cells provided herein having modulated growth characteristics can achieve higher cell density of the culture over time, for example, over a period of a week or more, with respect to a culture wild type algal cells of the same strain that are not modulated in growth characteristics. For example, a host cell of the invention as described herein may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) *Algae: Anatomy, Biochemistry & Biotechnology*, CRC Press, for media and methods for culturing algae. Algal media recipes can also be found at the websites of various algal culture collections, including, as non-limiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having a modulated growth characteristic as described herein can be cultured in a fermenter or bioreactor, where the bioreactor can optionally be a "photobioreactor" equipped with an artificial light source, and/or having one or more walls that is transparent enough to light, including sunlight, to enable, facilitate, and/or maintain photosynthetic microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

Biomass of the microorganism culture can be recovered by harvesting the microorganism from the medium, for example, by filtering, settling, centrifugation, or combinations thereof. In biomass production embodiments according to the invention, the amount of the biomass produced and/or recovered by the method described herein, measured as ash free dry weight (AFDW) can advantageously be at least about 0.05 g per liter of culture, for example at least about 0.1 g, at least about 0.2 g, at least about 0.3 g, at least about 0.4 g, at least about 0.5 g, at least about 0.6 g, at least about 0.7 g per liter of culture, at least about 1 g per liter of culture, at least about 1.5 g per liter of culture, at least about 2 g per liter of culture, at least about 2.5 g per liter of culture, or at least about 5 g per liter of culture. Although many times the goal can be to produce and/or recover as much biomass as possible, in some instances the amount of the biomass produced and/or recovered by the method described herein, measured as ash free dry weigh (AFDW) can be limited to about 15 g or less per liter of culture, for example about 12 g or less per liter of culture, about 10 g or less per liter of culture, about 5 g or less per liter of culture, about 2 g or less per liter of culture, about 1 g or less per liter of culture, or about 0.5 g or less per liter of culture.

Biomass can be harvested, for example, by centrifugation or filtering. The biomass may be dried and/or frozen. Further products may be isolated from biomass, such as, for example, lipids or one or more proteins. Thus, also provided in an aspect of the invention is an algal biomass comprising an algal host cell having modulated growth and/or phenotypic characteristics, such as any of the recombinant host cells disclosed herein, for example, an algal host cell comprising a nucleic acid molecule of the invention wherein elevated expression of the nucleic acid molecule results in higher biomass productivity.

Biomass can be used in any of a number of ways, for example, it can be processed for use as a biofuel by generating syngas from the biomass, can be supplied to an anaerobic digester for production of one or more alcohols, or the biomass can be extracted to provide algal lipids, such as but not limited to monoglycerides, diglycerides, or triglycerides, fatty acid alkyl esters, fatty acids, and/or fatty acid derivatives.

The host algal cell as described herein can include one or more non-native genes encoding a polypeptide for the production of a product, such as, but limited to, a lipid, a colorant or pigment, an antioxidant, a vitamin, a nucleotide, an nucleic acid, an amino acid, a hormone, a cytokine, a peptide, a protein, or a polymer. For example, a non-native gene can encode an enzyme, metabolic regulator, cofactor, carrier protein, or transporter.

In some embodiments, products such as fatty acids and fatty acid derivatives can be recovered from culture by recovery means known to those of ordinary skill in the art, such as by whole culture extraction, for example, using organic solvents. In some cases, recovery of fatty acids or fatty acid derivatives (such as fatty acid esters) can be enhanced by homogenization of the cells, as provided in the examples herein. When fatty acids are sufficiently released from the microorganisms into the culture medium, the recovery method can be adapted to efficiently recover only the released fatty acids, only the fatty acids produced and stored within the microorganisms, or both the produced and released fatty acids.

In further embodiments, products such as but not limited to free fatty acids and fatty acid derivatives that are secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids can then be eluted from the particulate adsorbents, e.g., by the use of an appropriate solvent. In such circumstances, one isolation method can include carrying out evaporation of the solvent, followed by further processing of the isolated fatty acids and lipids, to yield chemicals and/or fuels that can be used for a variety of commercial purposes.

Some embodiments of the invention concern methods that comprise culturing an algal host cell as described herein that further includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending U.S. Patent Application Publication 2013/entitled "Solvent Extraction of Products from Algae", filed on Feb. 29, 2012, which is incorporated herein by reference in its entirety.

The discussion of the general methods given herein is intended for illustrative purposes only. Other alternative methods and embodiments will be apparent to those of skill in the art upon review of this disclosure, and are to be included within the spirit and purview of this application.

In addition to the above description, the invention encompasses the following embodiments:

Embodiment 1

An isolated or recombinant nucleic acid molecule encoding a polypeptide having at least 50%, at least 55%, at least 60%, at least 65%, at least 70%, at least 75%, at least 80%, at least 85%, at least 90%, at least 95%, at least 96%, at least 97%, at least 98%, at least 99%, or 100% identity to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:50, or SEQ ID NO:52, preferably wherein the polypeptide comprises a B domain having at least 65%, at least 70%, at least 75%, at least 80%, at least 85%, at least 90%, at least 95%, at least 96%, at least 97%, at least 98%, at least 99%, or 100% identity to SEQ ID NO:4, amino acids 27-117 of SEQ ID NO:8; amino acids 23-113 of SEQ ID NO:10; amino acids 24-114 of SEQ ID NO:12; amino acids 24-114 of SEQ ID NO:14; amino acids 54-144 of SEQ ID NO:16, amino acids 19-109 of SEQ ID NO:18, amino acids 15-105 of SEQ ID NO:20, amino acids 18-108 of SEQ ID NO:22, amino acids 26-116 of SEQ ID NO:24, amino acids 29-119 of SEQ ID NO:26, amino acids 26-116 of SEQ ID NO:28, amino acids 23-113 of SEQ ID NO:30, amino acids 26-116 of SEQ ID NO:32, amino acids 20-110 of SEQ ID NO:34, amino acids 16-106 of SEQ ID NO:36, amino acids 24-114 of SEQ ID NO:38, amino acids 21-111 of SEQ ID NO:40, amino acids 29-119 of SEQ ID NO:42, amino acids 20-110 of SEQ ID NO:44, amino acids 20-110 of SEQ ID NO:46, amino acids 9-96 of SEQ ID NO:50, and amino acids 16-106 of SEQ ID NO:52.

Embodiment 2

An isolated or recombinant nucleic acid molecule according to embodiment 1, wherein the B domain is a non-LEC1 type HAP3-like protein B domain and/or the B domain comprises the amino acid sequence of SEQ ID NO:2, SEQ ID NO:3, SEQ ID NO:61, or SEQ ID NO:62.

Embodiment 4

An isolated or recombinant nucleic acid molecule encoding a polypeptide having at least 50%, at least 55%, at least 60%, at least 65%, at least 70%, at least 75%, at least 80%, at least 85%, at least 90%, at least 95%, at least 96%, at least 97%, at least 98%, at least 99%, or 100% identity to SEQ ID NO:64, SEQ ID NO:65, SEQ ID NO:66, or SEQ ID NO:68.

Embodiment 5

An isolated or recombinant nucleic acid molecule encoding a polypeptide having at least 50%, at least 55%, at least 60%, at least 65%, at least 70%, at least 75%, at least 80%, at least 85%, at least 90%, at least 95%, at least 96%, at least 97%, at least 98%, at least 99%, or 100% identity to SEQ ID NO:70.

Embodiment 6

A vector comprising a nucleic acid molecule to any of the nucleic acid molecules of Embodiments 1-5, wherein the vector comprises one or more of a) an origin of replication for propagation of the nucleic acid molecule in a host strain; b) a selectable marker; c) a reporter gene; d) expression sequences; and e) sequences for mediating homologous recombination into a host genome.

Embodiment 7

A recombinant eukaryotic microorganism comprising any of the nucleic acid molecules of Embodiments 1-6.

Embodiment 8

A recombinant eukaryotic microorganism comprising any two or all three of: a non-native nucleic acid molecule according to embodiment 1, a non-native nucleic acid molecule according to embodiment 4, and a non-native nucleic acid molecule according to embodiment 5.

Embodiment 9

A recombinant eukaryotic microorganism according to Embodiment 7 or Embodiment 8, wherein the eukaryotic microorganism is an alga or heterokont, optionally wherein the recombinant eukaryotic microorganism is a species of *Achnanthes, Amphiprora, Amphora, Ankistrodesmus, Asteromonas, Boekelovia, Bolidomonas, Borodinella, Botrydium, Botryococcus, Bracteo coccus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria, Volvox, Labryinthula, Labryinthuloides, Thraustochytrium, Schizochytrium, Aplanochytrium, Aurantiochytrium, Japonochytrium, Diplophrys,* or *Ulkenia.*

Embodiment 10

A recombinant eukaryotic microorganism according to any of embodiments 7-9, wherein the recombinant microorganism has higher productivity than a control microorganism substantially identical in all respects to the recombinant eukaryotic microorganism, with the exception that the control microorganism does not include a nucleic acid molecule according to any of embodiments 1-6.

Embodiment 11

A recombinant eukaryotic microorganism according to embodiment 10, wherein the higher productivity is higher growth rate, higher biomass accumulation, higher biomass productivity, higher rate of production of a biomolecule or higher amount of a biomolecule produced.

Embodiment 12

A recombinant eukaryotic microorganism according to any of embodiments 7-11, wherein the recombinant eukaryotic microorganism comprises at least one additional non-native gene encoding a polypeptide that participates in the production of a bioproduct, wherein the polypeptide that participates in the production of a bioproduct is optionally an enzyme or a transcriptional regulator.

Embodiment 13

A method of producing biomass or a bioproduct, comprising culturing a microorganism according to any of embodiments under conditions in which the nucleice acid molecule is expressed, wherein the microorganism produces biomass or a bioproduct.

Embodiment 14

A method according to embodiment 13, further comprising recovering biomass or the bioproduct from the culture, optionally wherein the bioproduct is a carbohydrate, a polymer, an alcohol, a sugar, a vitamin, a small molecule, a polyketide, a pigment, a colorant, a peptide, a protein, or a lipid.

Embodiment 15

A method according to embodiment 13 or 14, wherein the microorganism is an alga, optionally a species of Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria, or Volvox, optionally wherein said culturing is under photoautotrophic conditions.

EXAMPLES

Applicants have identified and isolated from the algal strain Nannochloropsis gaditana a novel member of the CCAAT-box binding transcription factor family that confers increased productivity in microorganisms. These discoveries were made by identifying genes encoding transcription factors in the genome of the algal strain Nannochloropsis WT-3730, constructing expression vectors including putative transcription factor genes, and transforming them into Nannochloropsis, and analyzing the resulting algal lines for increased productivity.

Example 1

Development of Nannochloropsis recombinant cells lines overexpressing one or more transcription factorsThe algal strain WT-3730 was derived from the strain Nannochloropsis gaditana CCMP1894 obtained from the Provasoli-Guillard National Center for Marine Algae and Microbiota (NCMA, Maine, U.S.A.), which is formerly the National Center for Culture of Marine Phytoplankton (CCMP). Whole genomic DNA content of the WT-3730 strain was first isolated and shot-gun sequenced. The whole genome-sequencing data was then assembled and annotated. Genes encoding putative transcription factors were identified bioinformatically by relying mainly on Pfam analyses and Hidden Markov Models (HMM) using the program hmmer3 (janelia.org). The 'Plant Transcription Factor Database' (Perez-Rodriguez et al. (2010) Nucl. Acids Res. 38 (Suppl 1): D822-D827) was also used as a reference. The identification was based upon coding regions, as the naturally-occurring genes generally included one or more introns that were identified and excluded from the resulting gene sequences that were identified and constructed as cDNAs from exon sequences and used in the transformation constructs (e.g., SEQ ID NO:5). The amino acid sequences provided in the sequence listing (e.g., SEQ ID NO:6) represent the encoded polypeptides of these cDNAs. With the goal in mind of enhancing lipid and or biomass productivity, 74 putative transcription factor genes (cDNAs) were selected and overexpressed in Nannochloropsis WT-3730 cells. For this purpose, numerous transformation vectors were constructed in which transcriptional expression of the genes encoding the transcription factors was placed under control of either a TCTP promoter from Nannochloropsis gaditana (SEQ ID NO:54) or an elongation factor promoter from Nannochloropsis gaditana (eIF3, SEQ ID NO:53). An example of one such vector is provided in FIG. 3.

For transformation, Nannochloropsis gaditana cells were grown in PM064 media and harvested at a concentration between 1-3×10$^7$ cells/mL. Cells were centrifuged at 2500×g for 10 minutes at 25° C. to pellet the cells. Cells were then resuspended in a sterile solution of 385 mM sorbitol and centrifuged again, then washed two more times in sorbitol to remove all traces of media. The cell pellet was resuspended in sorbitol to a final concentration of 1×10$^{10}$ cells/mL. Linearized plasmid DNA of construct was aliquoted into microfuge tubes at a concentration between 0.5-5 μg DNA, and 100 μL of cell mixture was mixed with the DNA. The mixture was transferred to chilled electroporation cuvettes with a gap distance of 2 mm. The electroporator was set to 50 μF capacitance, 500 ohms resistance and 2.2 kV voltage. Following electroporation, samples were resuspended in 1 mL of sorbitol and incubated on ice for a few minutes. Cells were transferred to 15 mL conical tubes containing 10 mL of fresh media, and allowed to recover overnight in dim light (~5 μmol photons m$^{-2}$ sec$^{-1}$). The next day, cells were plated at a concentration between 5-7×10$^8$ cells/mL on PM024 plates containing either 5 μg/mL zeocin, 100 μg/mL hygromycin, or 100 μg/mL blasticidin. Plates were incubated under constant light (~80 μmol photons m$^{-2}$ sec$^{-1}$) until colonies appeared (about 2-3 weeks).

PM024 media includes: 35 ppt Instant Ocean Salts (Aquatic Eco Systems; Apopka, Fla.), 10× Guillard's F/2 marine water enrichment solution (50× stock from Sigma- Aldrich, St. Louis, Mo., cat. No. G0154; final concentrations of components in media: 8.825 mM Sodium nitrate; 0.32 mM Sodium phosphate monobasic; 0.205 µM Biotin; 0.420 µM Cobalt chloride.6H$_2$O; 0.400 µM Cupric sulfate.5H$_2$O; 0.11713 mM Disodium EDTA.2H$_2$O; 9.095 µM Manganese chloride.4H$_2$O; 0.248 µM Sodium molybdate.2H$_2$O; 2.965 µM Thiamine.HCl; 0.037 µM Vitamin B$_{12}$; 0.765 µM Zinc sulfate.7H$_2$O).

PM064 media includes: 35 ppt Instant Ocean Salts, 5× Guillard's F/2 marine water enrichment solution (50× stock from Sigma-Aldrich, St. Louis, Mo., cat. No. G0154; final concentrations of components in media: 4.413 mM Sodium nitrate; 0.16 mM Sodium phosphate monobasic; 0.103 µM Biotin; 0.240 µM Cobalt chloride.6H$_2$O; 0.200 µM Cupric sulfate.5H$_2$O; 0.0585 mM Disodium EDTA.2H$_2$O; 4.54 µM Manganese chloride.4H$_2$O; 0.124 µM Sodium molybdate.2H$_2$O; 1.48 µM Thiamine.HCl; 0.0185 µM Vitamin B$_{12}$; 0.382 µM Zinc sulfate.7H$_2$O).

Example 2

Identification and Isolation of a *Nannochloropsis* CCAAT-Box Binding Transcription Factor that Conferred Increased Cell Biomass Productivity Recombinant algal cell lines overexpressing one or more of the transcription factors were subsequently screened for modulation in cell biomass productivity. Duplicate 25 cm$^2$ flasks containing approximately 30 ml PM066 medium were inoculated with algal cells from 20 ml liquid cultures that had been inoculated from 5 ml cultures started from cells growing on plates. After 3-6 days of growth, the cultures were diluted based on the growth characteristics of the strain such that they were estimated to reach late log phase in 3 days. The flasks were placed in an Adaptis growth chamber, shaking at approximately 130 rpm in an environment containing 1% CO$_2$ enriched air and exposed to approximately 274 µE·m$^{-2}$·s$^{-1}$ light on a 16 h light (at 30° C.): 8 h dark (at 25° C.) cycle. After 3 days, these seed cultures were used to inoculate 75 cm$^2$ flasks each containing a 200 ml total culture volume to a density providing approximately 35% light attenuation through the culture (which was 8.6 cm from the side closest to the light to the side farthest from the light). The tops of the flasks were fitted with a cap that included an air bubbling tube and a port used for culture sampling. Cultures were bubbled with 1% CO$_2$ enriched air on a shelf positioned against a light bank providing approximately 550 µE photosynthetically active radiation (PAR) at the front of the centrally positioned flask. The light regime was 16 hours of light (at 30° C.) to 8 hours of darkness (at 25° C.). After two days of growth, 6 mL samples were removed daily for FAME and TOC analysis and evaporative losses were made up with sterile distilled water during the seven day culturing period.

PM066 medium included 10 mM nitrate (NO$_3$) and 0.417 mM phosphate (PO$_4$) along with trace metals and vitamins in Instant Ocean salts. PM066 media was made by adding 5.71 ml of a 1.75 M NaNO$_3$ stock solution (148.7 g/L), and 5.41 ml of a 77 mM K$_2$HPO$_4$.3H$_2$O stock solution (17.57 g/L) to 981 mls of Instant Ocean salts solution (35 g/L) along with 4 ml of Chelated Metals Stock Solution and ml of 4 ml Vitamin Stock Solution. Chelated Metals Stock Solution was prepared by adding to 400 mls of water 2.18 g Na$_2$EDTA.2H$_2$O; 1.575 g FeCl3.6H$_2$O; 500 µl of 39.2 mM stock solution (0.98 g/100 ml) CuSO$_4$.5H$_2$O; 500 µl of 77.5 mM stock solution (2.23 g/100 ml) ZnSO$_4$.7H$_2$O; 500 µl of 42.0 mM stock solution (1.00 g/100 ml) CoCl$_2$.6H2O; 500 µl of 910.0 mM stock solution (18.0/100 ml) MnCl2.4H2O; 500 µl of 26.0 mM stock solution (0.63 g/100 ml) Na$_2$MoO$_4$.2H$_2$O; bringing up to 500 ml final volume, and filter sterilizing. Vitamin Stock Solution was prepared by adding to 400 mls of water 0.05 g Thiamine HCl; 500 µl of 0.37 mM stock solution (0.05 g/100 ml) of cyanocobalamin; and 2.5 ml of 0.41 mM stock solution (0.01 g/100 ml) of biotin, bringing up to a final volume of 500 mls, and filter sterilizing.

FAME analysis was performed on 2 mL samples that were dried using a GeneVac HT-4X. To the dried pellets the following was added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 of glass beads (425-600 µm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2 krpm and finally centrifuged for three minutes at 1 krpm. The heptane layer was sampled using a Gerstel MPS Autosampler. Quantitation used the 80 µg of C23:0 FAME internal standard.

Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

Figure 4C:
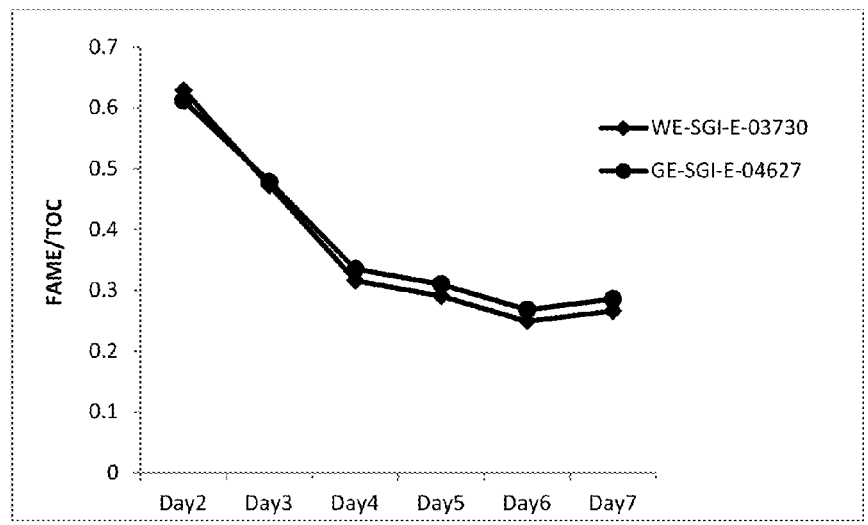

One line, GE-4627, displayed marked improved productivity over wild-type in this productivity assay (FIGS. 4A, 4B, and 4C). At 4 days into the run, the mutant started displaying higher fatty acid methyl esters content (FAME; FIG. 4A) and higher total organic carbon values (TOC; FIG. 4B). Similar FAME/TOC ratios were observed for wild type and the transgenic line throughout all time points (FIG. 4C). Table 2 shows FAME and TOC productivities calculated for the transgenic line GE-4627 compared against the wild type control.

TABLE 2

FAME and TOC productivities for WT-3730 and GE-4627.

| Strain | Day 2-4 | Day 4-6 | Day 4-7 | Day 5-7 | Day 6-7 |
|---|---|---|---|---|---|
| | FAME Productivity (µg/ml/day) | | | | |
| WT-3730 | 16.39 | 6.48 | 14.92 | 18.47 | 31.79 |
| GE-4627 | 12.10 | 23.06 | 30.84 | 34.23 | 46.40 |
| % increase over WT | −26.22 | 255.79 | 106.72 | 85.28 | 45.95 |
| | TOC Productivity (µg/ml/day) | | | | |
| WT-3730 | 140.58 | 87.63 | 84.85 | 93.43 | 79.30 |
| GE-4627 | 121.65 | 142.05 | 133.63 | 143.35 | 116.80 |
| % increase over WT | −13.46 | 62.11 | 57.49 | 53.44 | 47.29 |

Strain GE-4627 is a transgenic line that was created by transforming WT-3730 with a linearized vector designed to overexpress a gene annotated as a "CCAAT-box binding transcription factor subunit B (NF-YB) family". This family of transcription activators, also known as CBF and "HAP", is recognized by their central domain, a ~90-amino acid region of the protein that is conserved across eukaryotes. Therefore, and due to the strain's enhanced biomass phenotype, the gene was named HapY (happy).

The coding sequence of this novel gene, corresponding to a cDNA sequence, is provided in the Sequence Listing as SEQ ID NO:5. A homology search for SEQ ID NO:5 was conducted using the DDBJ/GenBank/EMBL database. Sequence identity and similarity were also determined using STN Express® software (STN International, Germany). In a BLASTX homology analysis SEQ ID NO:5 was determined to encode a CBFD_NF-YB_HMF domain. SEQ ID NO:6, the deduced amino acid sequence encoded by SEQ ID NO:5 (the HapY cDNA) was found to have sequence homology over approximately half its length (from amino acid 22 to amino acid 112, corresponding to the CBFD_NF-YB_HMF B domain) with a HAP3/NF-YB encoded by the genome of the lycophyte model organism *Selaginella moellendorffii*, having GeneBank accession number XP_002974018.1 (91% sequence identity over a 88/88 polypeptide alignment) and a HAP3/NF-YB subunit from the woodland strawberry *Fragaria vesca*, having GeneBank accession number XP_004304397.1 (89% sequence identity over a 88/88 polypeptide alignment). In addition, SEQ ID NO:6 displayed 88% sequence identity with another HAP3-like gene previously identified from the Irish potato famine pathogen *Phytophthora infestans*, having GeneBank accession number XP_002901676.1 (88% sequence identity over a 90/90 polypeptide alignment).

Further sequence analysis revealed that SEQ ID NO:6 (the polypeptide encoded by the HapY gene) contains several conserved domains and motifs that have been previously reported to be important for HAP3-like activity as well as for the physiological functions of a HAP3-like protein. For example, each of the conserved domains A, B, and C, which are characteristic of HAP3-like subunits previously reported by Harada et al. (*PNAS* 100(4): 2152-2156, 2003), were also found present in the amino acid sequence of SEQ ID NO:6 (see, e.g., the sequence alignment of FIG. 1 and the Sequence Listing). The conserved DNA-binding domain and the conserved subunit interaction domains were also found in the presently disclosed SEQ ID NO:6 from *N. gaditana*. In addition, the B domain, which typically includes about 90 residues and has been previously reported to be conserved in several HAP3-like subunits, was also identified in SEQ ID NO:6. Taken together, these results indicate that SEQ ID NO:1, the Hap_1742 ("HapY") gene, encodes a HAP3/NF-YB subunit of a CCAAT-box binding factor from *Nannochloropsis gaditana*.

Among HAP3/NF-YB homologs of higher plants, the B domain of the HAPY (SEQ ID NO:3) was found to be 95% identical to the B domain of a B8-like HAP3 (NF-YB) polypeptide of *Glycine max* (XP_003554361.1) and a B domain of a B3-like HAP3 (NF-YB) polypeptide of *Arabidopsis thaliana* (NP_193190.1). Both of these are non-LEC1 type NF-YB polypeptides. The B8-like HAP3 (NF-YB) polypeptide of *Glycine max* (XP_003554361.1) is referred to in U.S. Pat. No. 7,868,229 (provided in the patent as SEQ ID NO:24) as a member of the G482 subclade of non-LEC1-like HAP3 polypeptides that may affect flowering of higher plants. There is evidence that the B8-like HAP3 (NF-YB) polypeptide of *Arabidopsis thaliana* also affects flowering (Kumimoto et al. (2008) *Planta* 228:709-723.

Example 3

Productivity of Recombinant *Nannochloropsis* Cells Expressing HapY in Scaled Down Cultures A second productivity assay was used to verify the observed enhanced productivity of the strain engineered to overexpress SEQ ID NO:1 using a light exposure regime that was designed to replicate pond conditions. In this assay, triplicate 25 cm$^2$ flasks for each strain were inoculated with algae to provide a culture density of 0.15 OD 730 nm in a total volume of 500 mL (PM-066 medium). Stir bars were added to each flask, and stoppers having a syringe filter for air/CO$_2$ delivery and a clave connector for sampling were fitted to the flasks, which were given random positions along the 16-flask rack. The stir plates beneath the rack were operated at 450 rpm. The LED light bank provided a light regime designed to simulate pond conditions, in which the peak light intensity of the 12 hour daily light period was 1800 μE·m$^{-2}$·s$^{-1}$ and the temperature varied from 25° C. to 34° C., Samples (typically 2 mLs) were removed on days 3, 4, 5, 6, 7, 8, 9, and 10 for TOC and FAME analysis.

Figure 5A:
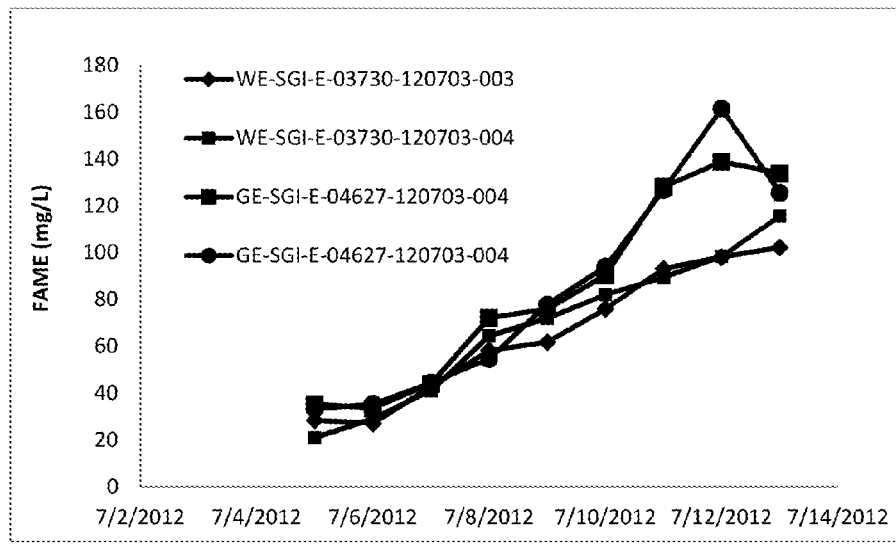
FIGS. 5A and 5B illustrate the results of experiments monitoring the enhanced productivity of the cell line GE-4627 a scaled down growth assay based on pond conditions (see, e.g. Example 3).
Figure 5B:
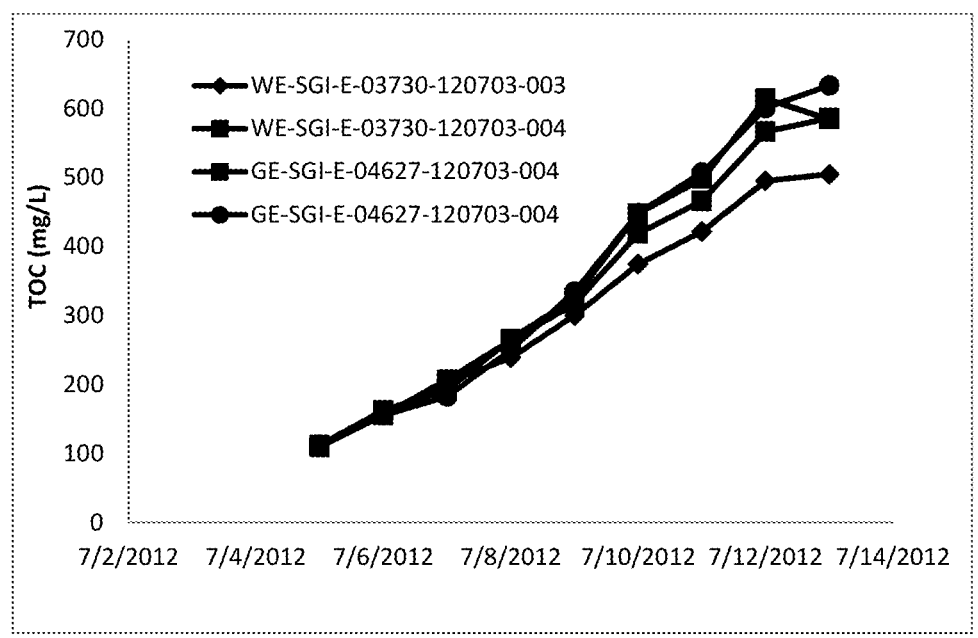
Figure 6:
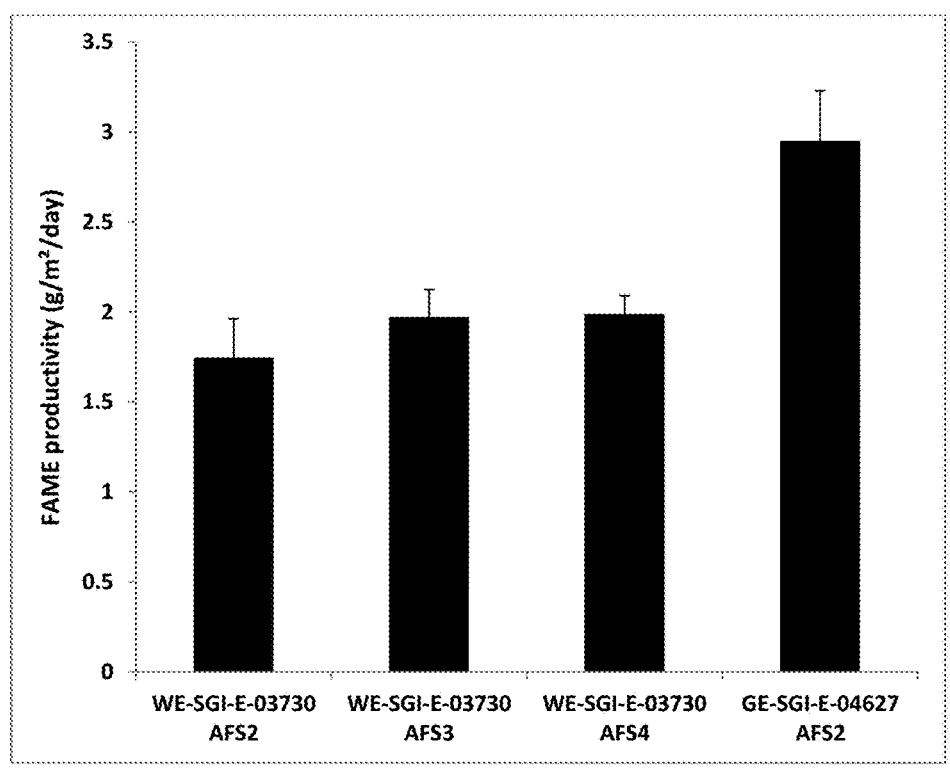
FIG. 6 summarizes the FAME productivities for recombinant cell line GE-4627 and wild-type controls, WT-3730. Values shown are for the best 3-day averages. Error bars are standard deviations for two biological replicates.

Again, the HapY overexpressor line was observed to outperform the wild type in FAME and biomass productivity (FIGS. 5A and 5B). Using this assay, the transgenic line displayed a 50% increase in FAME productivity over wild type (FIG. 6). As previously observed, FAME/TOC ratios in this experiment were relatively equal for both strains, thus indicating that increased FAME productivity was likely a result of increased overall biomass productivity.

To determine the expression levels of the *N. gaditana* HapY gene in strain GE-4627, mRNA levels were measured during different time-points of the light bank productivity assay by quantitative real-time PCR (qRT-PCR). mRNA was isolated from GE-4627 cells and wild-type control cells and mRNA levels of HapY (Hap_1742) were measured by gene-specific primers. As expected, in two separate experiments, mRNA levels of the HapY (Hap_1742) gene in the overexpressor line GE-4627 were found to be up to 10-fold higher when compared to wild-type control.

Example 4

Transcriptomics of Transgenic Algal Cells Overexpressing HapY

To determine the transcriptional changes caused by overexpression of the *N. gaditana* HapY gene (SEQ ID NO:5), transcriptomes of two lines overexpressing *N. gaditana* HapY were sequenced at 2 different time-points (days 4 and 7 of the culturing period) and compared to wild type grown under the same conditions.

RNA was extracted from wild-type and HapY overexpressing transgenic cells harvested 4 and 7 days after the culture was initiated at an optical density of 0.2 (730 nm). After harvesting on day 4, NaNO$_3$ was spiked at a final concentration of 8 mM to ensure the cultures did not enter nitrogen depletion during the remainder of the experiment.

To isolate total RNA, 10 mLs of an algal cell culture was spun down at 4000×g for 5 minutes and the supernatant was decanted. The pellet was resuspended in 1.8 mL Buffer A (5 mL TLE Grinding Buffer, 5 mL phenol, 1 mL 1-bromo-3-chloropropane and 20 μL mercaptoethanol, where TLE Grinding Buffer includes 9 mL of 1M Tris pH 8, 5 mL of 10% SDS, 0.6 mL of 7.5 M LiCl, and 0.45 M EDTA, in a final volume of 50 mL) and transferred to a 2 mL microcentrifuge tube containing approximately 0.5 mL of 200 μm zirconium beads. The tube was vortexed vigorously for 5 min at 4° C. and then centrifuged for 2 min at 11.8×g. The aqueous layer was then removed and pipetted into a new 2 mL tube, to which 1 mL 25:24:1 phenol extraction buffer (25 mL phenol pH 8 or 5.1; 24 mL 1-bromo-3-chloropropane, and 1 mL isoamyl alcohol) was added and the tube was shaken vigorously and centrifuged for 2 min at 11.8×g. After centrifugation, the aqueous layer was removed and pipetted into a new 2 mL centrifuge tube, to which 1 ml 1-bromo-3-chloropropane was added. The tube was shaken and again centrifuged for 2 min at 11.8×g. The aqueous layer was removed to a new tube and 0.356 volumes of 7.5 M LiCl was added. The tube was inverted 10-12 times and stored at −20° C. overnight. The next day, samples were allowed to come to room temperature without mixing and were centrifuged at 16,000×g for 30 minutes. The supernatant was removed and the pellet was washed with 1 mL of ice cold 80% ethanol. The tube was centrifuged for 30 min at 16,000×g and allowed to air dry after the supernatant had been removed. Finally, the RNA pellet was resuspended in 50 μl ultrapure water. The RNA quality was assessed by on-chip gel electrophoresis using an Agilent 2100 Bioanalyzer and RNA6000 LabChip according to manufacturer instructions.

Next-generation sequencing libraries were prepared from the isolated RNA utilizing the TruSeq Stranded mRNA Sample Prep Kit (Illumina) following manufacturer instructions. The TruSeq libraries were sequenced using sequencing-by-synthesis (Illumina MiSeq) to generate 100 bp paired-end reads using the mRNA-Seq procedure (described in Mortazavi et al. (2008) Nature Methods 5:621-628). Mappable reads were aligned to the N. gaditana reference genome sequence using TopHat (tophat.cbcb.umd.edu/). Expression levels were computed for every annotated using the Cuffdiff component of the Cufflinks software (cufflinks.cbcb.umd.edu). Differential expression analysis was performed using the R package edgeR (McCarthy et al. (2012) Nucl. Acids Res. 40:doi:10/1093/naegks042)). Expression levels in units of fragments per kilobase per million (FPKM) were reported for every gene in each sample using standard parameters. FPKM is a measure of relative transcriptional levels that normalizes for differences in transcript length.

Tables 3 and 4 show genes that were differentially expressed in the transgenic lines compared to wild type. In addition to HapY (the first row of Table 3), two other regulators were observed to be upregulated in the transgenic lines (Table 3, highlighted in bold font).

As discussed above, transcription factors that belong to the same family as HapY (CBF/Hap/NF-Y), have been reported to bind CCAAT boxes located upstream of regulated genes, therefore we examined the number of CCAAT boxes present in the putative promoters of the upregulated genes and found that all genes upregulated by at least two-fold (log 2 of the fold change of at least 1) contained one or more CCAAT boxes. Thus, enrichment of CCAAT binding boxes in this subset supported the bioinformatic prediction that HapY is a CBF transcription factor and provided confidence in the upregulated targets identified.

TABLE 3

Differentially expressed genes found to be upregulated in HapY overexpressor lines compared to WT. Only genes with a false discovery rate (FDR) value <0.05 are shown.

| Predicted polypeptide encoded by gene (by closest homology) | CCAAT Box motifs in 5' region of gene | Log (2) FC | FDR |
|---|---|---|---|
| CCAAT-box binding transcription factor subunit B (HapY) | 2 | 1.8 | 5.6e−21 |
| Epimerase/dehydratase | 1 | 1.4 | 7.3e−10 |
| Ion channel | 2 | 1.4 | 3.4e−16 |
| dehydrogenase | 2 | 1.1 | 0.013 |
| Myb-like DNA-binding domain protein | 2 | 1.1 | 0.00014 |
| Metabolic enzyme | 2 | 1 | 0.016 |
| Kinase | 2 | 0.9 | 8.7e−06 |
| Transcription factor | | 0.9 | 0.00033 |
| Unknown predicted protein | 3 | 0.9 | 0.0072 |
| RNA-binding protein | 1 | 0.8 | 0.00092 |
| Metabolic enzyme | 1 | 0.8 | 0.019 |
| Unknown protein | | 0.8 | 0.041 |
| Purine metabolism | | 0.7 | 0.0004 |

TABLE 4

Differentially expressed genes found to be downregulated in HapY overexpressor lines compared to WT. Only genes with a false discovery rate (FDR) value <0.05 are shown.

| Predicted polypeptide encoded by gene (by closest homology) | CCAAT Box motifs in 5' region of gene | Log (2) FC | FDR |
|---|---|---|---|
| Nuclear protein | | −0.6 | 0.0013 |
| RNA-binding protein | 1 | −0.6 | 0.0069 |
| Unknown predicted protein | | −0.7 | 0.0096 |
| chaperonin | 1 | −0.9 | 0.00011 |
| Metabolic enzyme | | −1.1 | 0.000017 |
| Mitochondrial protein | 3 | −1.3 | 0.034 |
| Unknown predicted protein | | −2 | 1.3e−06 |
| Cytoskeleton-related | | −2.8 | 1.5e−14 |

Example 5

Identification of Genes Encoding HapY Homologs from Marine Microorganisms

This example describes the identification of genes encoding homologs of HapY from several marine microorganisms, including Nannochloropsis oceanica, Tetraselmis sp., Cyclotella sp., Navicula sp., Chlorella sp., and Botryococcus brauniii.

Whole genomic DNA content of several marine microorganisms was first prepared individually for shotgun 454-pyrosequencing. Genomic DNA was used for library construction according to the recommended protocol (454 Life Sciences) for single long reads. The sequences were generated by GS FLX Titanium series sequencing runs. Mate-pair and paired-end genomic DNA library construction was performed for Illumina short-read (100 bp) sequencing of the Nannochloropsis genomes.

For cDNA sequencing, total RNA was isolated from individual microbial isolates using Qiagen RNeasy Maxi™ columns according to the manufacturer's recommendations. cDNA was synthesized by fragmenting the RNA and converting it to cDNA with random primers using the Illumina mRNA-Seq Library Preparation Kit according to the manufacturer's recommendation. Illumina adapters were then ligated to the DNA ends and the sample was PCR amplified using reagents in the same kit. The DNA template was sequenced on an Illumina Genome Analyzer II™ platform according to the manufacturer's recommended conditions. Paired-end reads were generated and mapped to the assembled genome sequence as described below.

Genome sequence assemblies were carried out using Newbler assembler version 2.0.00.20 for the 454-sequence data and using ALLPATHS-LG for the Illumina mate-pair and paired-end data. Coding gene sequences were predicted from assembled genomic contigs using an approach that combined evidence from multiple sources using either the Evigan consensus gene prediction method (Liu et al., *Bioinformatics*, 24(5):597-605, 2008) or Augustus (Stanke et al., *BMC Bioinformatics* 7, 2006). Putative transcription factors were then identified using probabilistic Hidden Markov Models (HMMER version 3; which can be found at hmmer.janelia.org/) with PFAM models on the predicted gene sequences.

In addition to the HMM-based ab initio gene model, further direct evidence on gene structure was included in the predictions using the hints mechanism included in the Augustus program. This mechanism allows providing additional evidence on gene features such as exon-intron boundaries that Augustus can use to determine for example the location of an exon-intron boundary that is both consistent with the ab initio model and is supported by direct experimental data. The evidence used in gene finding process included GeneWise protein-DNA alignments, Solexa based exon-intron splice junctions generated using Tophat, and assembled transcripts created using the program Cufflinks. The weights for all hints were derived by optimizing them using an accuracy function based on the sensitivity and specificity of gene prediction results on *Arabidopsis* genome sequence using the manually curated *Arabidopsis* genome annotation (TAIR database,www.arabidopsis.org/) as a reference data set. Alternative transcripts for genes were also predicted when the evidence supported their presence.

Figure 7:
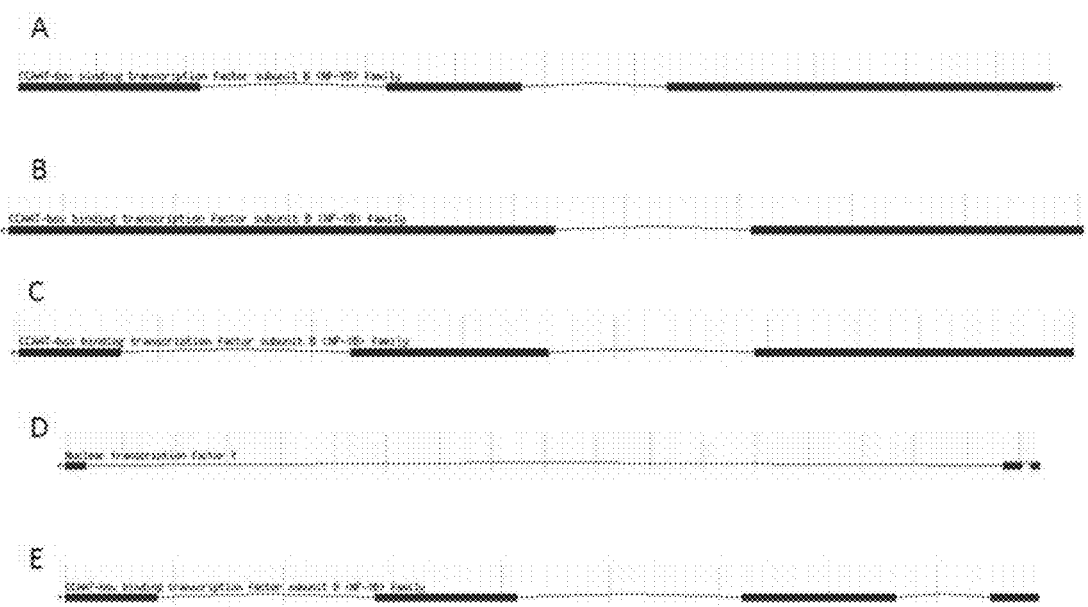
FIG. 7 provides the gene structure of HapY genes from various algal species. A) *Nannochlorosis gaditana*; B) *Nannochlorosis oceanica*; C) *Tetraselmis* sp.; D) *Cyclotella* sp.; E) *Chlorella* sp. Introns are denoted by thin lines, and exons by thick lines. The sizes of the algal genes are not scaled to one another.

Several HapY genes from marine microorganisms have been identified by the process described above. For example, HapY genes were identified from genomic DNA and cDNA sequence data to reconstruct HapY cDNA sequences from of *Nannochloropsis oceanica* (SEQ ID NO:7), *Cyclotella* sp. (SEQ ID NO: 15), *Navicula* sp. (SEQ ID NO:17), *Chlorella* sp (SEQ ID NO:19), and *Botryococcus braunii* (SEQ ID NO:21). The gene structure of several of these homologs is provided in FIG. 7, demonstrating that the native genes include introns. In addition, three HapY-like genes (SEQ ID NOs: 9, 11, and 13) were identified from the genomes of three independent *Tetraselmis* isolates. In addition, orthologs of HapY from *Flagilariopsis cylindrus* (SEQ ID NO:24), *Phaeodactylum tricornutum* (SEQ ID NO:34), *Volvox carteri* (SEQ ID NO:36), *Micromonas pusilla* (SEQ ID NO:38), *Micromonas* sp. (SEQ ID NO:40), *Schizochytrium aggregatum* (SEQ ID NO:50), and *Aplanochytrium* sp. (SEQ ID NO:52) were identified from public genomes by homology searching.

Further information pertaining to the conserved domains identified in each of the HapY-like polypeptides, as well as their respective closest homologs in public databases is provided in Table 1 and in the Sequence Listing attached hereto.

Example 6

Genetic Transformation of *Tetraselmis* by Particle Bombardment

*Tetraselmis* transformation is carried out by particles bombardment using the Bio-Rad Helio™ PDS-1000/He gene gun apparatus according to manufacturer's instructions with minor modifications.

Plasmid DNA isolated from overnight *E. coli* cultures is quantitated and digested overnight with an enzyme appropriate for linearization. The plasmid includes a nucleic acid sequence encoding any of SEQ ID NO:10, SEQ ID NO:12, or SEQ ID NO:14, operably linked to the *Tetraselmis* GAPDH promoter of SEQ ID NO:55 (or any of the promoters provided in U.S. Ser. No. 13/693,585, filed Dec. 4, 2012, and incorporated herein by reference in its entirety) and the GAPDH terminator (SEQ ID NO:56). The plasmid can further include a selectable marker, such as, for example, the *Streptoalloteichus hindustanus* (Sh) ble gene conferring Zeocin-resistance and codon-optimized for expression in *Chlamydomonas reinhardtii* (SEQ ID NO:57), which can be operably linked to an algal promoter, such as, for example, the *Tetraselmis* actin promoter (SEQ ID NO:58) and the *Tetraselmis* actin terminator fragment (SEQ ID NO:59).

Gold particles are prepared as follows: Gold microcarriers (Bio-Rad Cat 165-2262) are weighed into a 1.5 mL tube. For 40 shots at 0.5 mg gold/shot, typically 20 mg of gold microcarriers is used. Following addition of 100 μL 0.05M spermidine, the tube is vortexed, and may then be sonicated for 5 seconds. Plasmid DNA is then added to the tube, followed by brief vortexing. While vortexing, 100 uL 1M $CaCl_2$ is added drop-wise. The volume of plasmid varies depending on the desired amount of DNA per shot. The tube is then incubated at room temperature for 10 minutes. The gold preparation is centrifuged briefly for 10-15 seconds to discard the supernatant. The pellet is washed three times with 1 mL ethanol, with vortexing and spinning down between each wash. The pellet is then resuspended in a 2.5 mL ethanol/PVP solution (a mixture of 2.5 mL ethanol and 1.25 uL of 20 mg/mL PVP stock in ethanol), followed by sonication for 5 seconds.

Two days prior to shooting, a culture of a *Tetraselmis* strain, WT-105, is inoculated at $5\times10^5$ cells/mL in PM032 media, and cells are grown at 25° C., 1% $CO_2$ on a rotation share set at 125 rpm on a 16:8 light:dark cycle. In a typical protocol of particle bombardment, algal cells are first concentrated and plated prior to transformation shootings. Algal cells are counted using Accuri cytometer. A cell count of at $1\times10^6$ cells/mL is preferable. Cells are then concentrated to $5\times10^7$ cells/mL before plating 200 uL of concentrated cells onto PM032 1.5% agar plates within a 4 cm-diameter circle. A total of 15 circles (e.g. a total of $1.5\times10^8$ cells) are placed on a single 22×22 cm plate and allowed to dry. The distance between the stopping ring and the target (microalgal cells) is 5 cm. Plates are placed on the bench to recover for approximately 24 hours.

PM032 medium is 10× F/2 replete medium that includes 8.8 mM $NaNO_3$ and 0.4361 mM $NaH_2PO_4.H_2O$, 10×F/2 Trace metals, and 10×F/2 Vitamins and can be made by mixing 1.3 ml/L of ProLine F/2 Part A and 1.3 ml/L of ProLine F/2 Part B in 800 ml seawater. The solution is stirred thoroughly, brought up to 1 liter with distilled water, and filter sterilized using a 0.22 μm filter.

After transformation, algal cells are recovered by adding approximately 20 mL of PM032 media to the plate. Algal cells are scrapped with inoculating loop to resuspend cells in liquid PM032 media. A 25 mL serological pipette is used to remove as much liquid media as possible from plate and place in a 50 mL conical tube. An additional 20 mL of PM032 media is added to the plate to recover any remaining algae and transfer this liquid media to the conical tube. Cells are pelleted by centrifugation at 3,000×g for 5 minutes, resuspended in 4 mL PM032, and then spread with autoclaved glass beads onto two 22×22 cm selection plates.

Plates are allowed to dry, wrapped in micropore tape and placed on light shelves. Algal colonies typically appear after 1-2 weeks.

Example 7

Genetic Transformation of *Cyclotella* by Particle Bombardment

Plasmid DNA isolated from overnight *E. coli* cultures is quantitated and digested overnight with an enzyme appropriate for linearization. The plasmid includes nucleic acid sequence SEQ ID NO:15, encoding *Cyclotella* HapY, operably linked to the *Cyclotella* Accase promoter of SEQ ID NO:60 (or any of the promoters provided in Niu et aL (2012) BioTechniques Rapid Dispatches doi:10.2144/000113881). The plasmid can further include a selectable marker, such as, for example, the *Streptoalloteichus hindustanus* (Sh) ble gene conferring Zeocin-resistance and codon-optimized for expression in *Chlamydomonas reinhardtii* (SEQ ID NO:57), which can be operably linked to an algal promoter, such as, for example, any provided in Paulsen & Kroger FEBS J. 272: 3413-23 or Siaut et al. Gene 406:23-35.

Cultures of a diatom *Cyclotella* strain, WT-293, are grown in PM101 liquid media in high light growth conditions, 30° C., under a 14:10 diel cycle (Adaptis incubator). Cells at exponential growth phase ($<1 \times 10^6$ cells/ml) are pelleted by centrifugation (20 minutes, 5000 g, 20° C.), resuspended in ~20 mls of 0.5M Osmoticum (0.25M Sorbitol+0.25M Mannitol) for a high concentration of cells (~$1 \times 10^8$ cells/ml), and determined cell count. Approximately $3 \times 10^7$ cells are spread onto the center ⅔rd of a PM101 agar plate. PM101 media is identical to PM024 described in Example 1, except for it contains 10 mM $NaNO_3$, 0.417 mM $K_2HPO_4$ and 1 mM $Na_2SiO_3$. Plates are then allowed to dry in sterile hood.

The microcarriers are tungsten particles M17 (Bio-Rad Cat#165-2267). Microcarriers are prepared according to the protocol of the supplier (Bio-Rad), and include the following steps. (1) Weigh 60 mg of tungsten particles into "Treff" microtubes (VWR Cat.#101100-388); (2) Add 1 ml 70% Ethanol and vortex for 5 minutes at room temperature; (3) Store the tube on the bench top for 15 minutes; (4) Centrifuge in picofuge for 5 seconds; (5) Remove supernatant and resuspend in 1 ml sterile $H_2O$; (6) Vortex for 1 minute and then store the tube on the bench top for 1 minute; (7) Centrifuge in picofuge for 5 seconds; (8) Repeat H2O wash (steps 5-7) three more times; and (9) Remove supernatant after final wash and resuspend particles in 1 ml of sterile 50% glycerol.

In most *Cyclotella* transformation experiments, the DNA binding procedure involves the following steps. (1) While vortexing stock solution of microcarrier particles, remove a 50 µl aliquot of beads (i.e., approximately 3 mg) and transfer to a fresh microfuge tube; (2) To the aliquot, add plasmid DNA (3 µg). Plasmid DNA is preferably at a high concentration (~1 mg/ml); (3) Add 50 µl of 2.5M $CaCl_2$; (4) Add 20 µl of 0.1M spermidine (Fluka 05292-1ML-F); (5) continue to vortex tube for an additional 3 minutes; (6) Store the tube on the bench top for 1 minute; (7) Pellet particles for 2 seconds in picofuge; (8) Remove supernatant and carefully layer with 140 µl of 70% Ethanol; (9) Remove supernatant and carefully layer with 140 µl of 100% Ethanol; and (10) Remove supernatant and resuspend in 30 µl 100% Ethanol.

The macrocarriers (Bio-Rad Cat#165-2335) are prepared by setting up X-segmented Petri dishes (VWR Cat#25384-308) with desiccant in each quadrant. Autoclaved macrocarrier/macrocarrier holder is then placed in each quadrant atop desiccant. Approximately, 10 µl of DNA/Beads is dispensed onto center of macrocarrier and allowed to dry.

A typical protocol of particle bombardment includes the following steps. (1) Dip rupture disk (Bio-Rad #165-2330) into isopropanol and place in rupture disk retaining cap; (2) Secure retaining cap to end of gas acceleration tube and tighten with torque wrench; (3) Load stopping screen (Bio-Rad Cat#165-2336) and macrocarrier into microcarrier launch assembly; (4) Place microcarrier launch assembly into chamber; (5) Place target shelf with agar plate containing cells on Level 2 in chamber and close door; (6) Apply vacuum and hold at 10Hg; (7) Depress FIRE button until rupture disk bursts; (8) Release vacuum, open door and remove agar plate; (9) Unload macrocarrier and stopping screen from launch assembly; (10) Unload spent rupture disk. Helium pressure in a Biolistic PDS-1000-HE particle delivery system used in these transformation experiments is set at approximately 2,000 psi, and the distance between rupture disk retaining cap and microcarrier launch assembly is 0.5 cm, which can be verified using hexagonal gap tools.

After bombardment, diatom cells are recovered as follows. Cells are scraped from agar plate by adding ~5 ml media and scraping with L-shaped spreader; transferred to 50 ml PM101 media in a 125 ml flask, which is then incubated in approximately 50 E light, 30° C., 1% $CO_2$ and cells are allowed to recover for 24 hrs. At this step, cell counts can be determined before being pelleted by centrifugation. Supernatant is decanted by leaving ~1-2 ml media. Cell culture is resuspended in remaining media and plated onto Antibiotic plates (max. $2 \times 10^7$ cells/plate). Plates are then wrapped with micropore tape and placed under high light. Diatom colonies typically appear after 1-2 weeks.

Example 8

Molecular Characterization and Evaluation of Recombinant Algal Cells

The ability of a recombinant HapY polypeptide to confer modulated biomass productivity is assessed in a number of ways. Following introduction of heterologous foreign DNA into algal cells, the transformation or integration of heterologous gene in the algal genome is confirmed by a number of methods such as analysis of nucleic acids, proteins and metabolites associated with the integrated gene. For example, PCR analysis is a rapid method, among others, to screen transformed cells (Sambrook and Russell, 2001, supra). PCRs are carried out using oligonucleotide primers specific to the antibiotic-tolerance gene of interest or to the transformation vector backbone, etc.

Algal transformants derived from transformation experiments are also confirmed by Southern blot analysis of genomic DNA (Sambrook and Russell, 2001, supra). In general, total DNA is extracted from the transformant by using a procedure described previously (see, e.g. European Pat. Appl. No. EP2090648A1), digested with appropriate restriction enzymes, size-fractionated in an agarose gel and transferred to a nitrocellulose or nylon membrane. The membrane or "blot" is then probed with, for example, a nonradioactive DIG-labeled target DNA fragment to confirm the integration of introduced gene into the plant genome according to standard techniques ("Genius" DIG-based system, Boehringer Mannheim Biochemicals GmbH, Germany; Sambrook and Russell, 2001, supra), or a radiolabeled $^{32}P$ probe may be used for Southern blot analysis.

Expression of the HapY transgene can be evaluated by PCR. Western blot, biochemical assays and the like can also be carried out on the transgenic algae to confirm the presence of protein encoded by the HapY gene by standard procedures (e.g., Sambrook and Russell, 2001, supra) using antibodies that bind to one or more epitopes present on the HapY protein.

The effects of the exogenous HapY gene can be investigated using the productivity assays provided herein, or similar assays in which the recombinant algal cells that overexpress a HapY gene or a gene encoding a protein homologous to a HapY protein are cultured and analyzed for production or accumulation of a product. The product can be, as nonlimiting examples, a carbohydrate, a polymer, an alcohol, a sugar, a vitamin, a small molecule, a polyketide, a pigment, a colorant, a peptide, a protein, or a lipid. Alternatively or in addition, a recombinant cell that overexpresses a HapY gene or an ortholog thereof can be tested for increased growth rate and/or biomass accumulation.

Example 9

Yeast Two Hybrid Screens for NF-Y Subunits Interacting with Hap-1742

Analysis of the primary structure of Hap-1742 (HapY) defines it as a B subunit of a CBF/NF-Y transcription factor heterocomplex that is conserved in most eukaryotes and usually consists of a heterotrimer (consisting of NF-Y subunits A, B and C) or heterodimer complex (consisting of NF-Y subunits B and C). In order to identify other components of the Hap-1742 transcription factor complex, full-length Hap-1742 protein was screened for using Yeast Two Hybrid (Y2H) discovery methods (see, for example, Chien et al. (1991) *Proc. Natl. Acad. Sci.* 88: 9578-9582; Guarente (1993) *Proc. Natl. Acad. Sci.* 90: 1639-1641; Rutisjmu & Golemis (2008) *Biotechniques* 44: 655-662). After subtraction of false positives (by direct comparison to our "false positives database" which consists of background proteins that appear in most of our screens), two hits remained: EUKT-6092 and EUKT-1490. Based on our knowledge of NF-Y transcription factors, these hits appear to be bona fide interactors that bind to Hap-1742 in vivo.

Total *Nannochloropsis* RNA was isolated independently from four different growth conditions (nitrogen replete growth, nitrogen deprivation, phosphorous deprivation, and high light conditions) for making cDNA to screen in the Yeast Two Hybrid assay, 10 mLs of an algal cell culture was spun down at 4000×g for 5 minutes and the supernatant was decanted. The pellet was resuspended in 1.8 mL Buffer A (5 mL TLE Grinding Buffer, 5 mL phenol, 1 mL 1-bromo-3-chloropropane and 20 µL mercaptoethanol, where TLE Grinding Buffer includes 9 mL of 1M Tris pH 8, 5 mL of 10% SDS, 0.6 mL of 7.5 M LiCl, and 0.45 M EDTA, in a final volume of 50 mL) and transferred to a 2 mL microcentrifuge tube containing approximately 0.5 mL of 200 µM zirconium beads. The tube was vortexed vigorously for 5 min at 4° C. and then centrifuged for 2 min at 11.8×g. The aqueous layer was then removed and pipetted into a new 2 mL tube, to which 1 mL 25:24:1 phenol extraction buffer (25 mL phenol pH 8 or 5.1; 24 mL 1-bromo-3-chloropropane, and 1 mL isoamyl alcohol) was added and the tube was shaken vigorously and centrifuged for 2 min at 11.8×g. After centrifugation, the aqueous layer was removed and pipetted into a new 2 mL centrifuge tube, to which 1 ml 1-bromo-3-chloropropane was added. The tube was shaken and again centrifuged for 2 min at 11.8×g. The aqueous layer was removed to a new tube and 0.356 volumes of 7.5 M LiCl was added. The tube was inverted 1042 times and stored at −20° C. overnight. The next day, samples were allowed to come to room temperature without mixing and were centrifuged at 16,000×g for 30 minutes. The supernatant was removed and the pellet was washed with 1 mL of ice cold 80% ethanol. The tube was centrifuged for 30 min at 16,000×g and allowed to air dry after the supernatant had been removed. Finally, the RNA pellet was resuspended in 50 µl ultrapure water. The RNA quality was assessed by on-chip gel electrophoresis using an Agilent 2100 Bioanalyzer and RNA6000 LabChip according to manufacturer instructions.

The cDNA library was synthesized using the Make Your Own "Mate & Plate™" Library System User Manual as a guideline (Clontech, Mountain View, Calif.). However, instead of using the SMART III Oligo provided by the kit, a modified 5' primer that takes advantage of a previously described splice leader identified in *Nannochloropsis* (see US Patent application Publication 2014/0186842, "*Nannochloropsis* Spliced Leader Sequences and Uses Therefor" filed Dec. 5, 2013, incorporated herein in its entirety) was used for first strand synthesis (5' primer MCA-1185:

(SEQ ID NO: 71)
5'-ttccacccaagcagtggtatcaacgcagagtggcctaagggaaaaca acag-3';.

A modified 3' primer was also used for second strand synthesis:

(SEQ ID NO: 72)
5'-gtatcgatgcccaccctctagaggccgaggcggccgacacggtaccc gctttttttttttt-3'.

Both modified 5' and 3' primers contained sequence extensions that added nucleotide sequences compatible with the yeast expression vector pGADT7-rec (Clontech) to allow for subsequent cloning by circular polymerase extension cloning (cpec; see for example Quan & Tijan (2009) *PLoS One* 4(7): e6441). After cloning of the second strand cDNA into pGAD-T7-rec, the resulting library was transformed into *E. coli*. Approximately 750,000 colonies were obtained which represents at least 25-fold coverage of the *Nannochloropsis* transcriptome. Low redundancy of the library was verified by sequencing and the library was transformed into yeast strain Y2HGold (Clontech). The final yeast expression library consisted of more than 2 million colonies.

The coding sequence of Hap-1742 was amplified from cDNA using forward primer JLC-pGBKT7-Hap1742-F: (5'-CATGGAGGCCGAATTCatggatgaggcgggagccaacgag-3'; SEQ ID NO:75) and reverse primer JLC-pGBKT7-Hap1742-R (5'-GCAGGTCGACGGATCCt c aggaaggcg-gctgccttgacac-3'; SEQ ID NO:76). It was cloned into the bait vector pGBKT7 (Clontech) by circular polymerase extension cloning and transformed into *E. coli*. Upon sequence confirmation it was transformed into yeast strain Y187 (Clontech) and screened for interactions against the *Nannochloropsis* cDNA library cloned into the prey vector as described above.

The prey library was screened for by mating of the library-containing (prey) strain with a bait strain (i.e., a strain expressing Hap-1742) according to the Matchmaker™ Gold Yeast Two-Hybrid System User Manual (Clontech). A mating efficiency of ~4.5% was achieved for the Hap-1742 screen (good mating efficiencies are usually between 3-5%).

Based on these numbers, it is estimated that more than 10 million interactions were tested.

Using this technique, clones were identified as including genes that encoded proteins that interact with Hap-1742 based on their growth and blue color on selective media, which resulted from the interaction of the expressed proteins with Hap-1742 and the subsequent activation of auxotrophic markers and a reporter gene. Two of the positive clones included constructs that encoded *Nannochloropsis* NF-YC polypeptides: EUKT6092 (SEQ ID NO:64, encoded by SEQ ID NO:63) and EUKT1490 (SEQ ID NO:68, encoded by SEQ ID NO:67).

EUKT6092 (SEQ ID NO:63) encodes a polypeptide (SEQ ID NO:64) having a COG5208 (CCAAT-binding factor, subunit C) domain corresponding to amino acid residues 14 to 138 of the protein (bit score 131.33; e value 6.27 e-38) identifying EUKT6092 as an NF-YC polypeptide (in alternative nomenclatures called a CBF (CCAAT-binding factor) subunit C or HAP5 polypeptide). EUKT6092 also includes a COG5247 (Class 2 transcription repressor NC2, alpha subunit (DRAP1 homolog)) domain extending from amino acid 64 to amino acid 138; a COG2036 (Histones H3 and H4) domain extending from amino acid 62 to amino acid 126; and a COG5262 (Histone 2A) domain extending from amino acid 64 to amino acid 135. EUKT6092 recruits to pfam00808 (histone-like transcription factor (CBF/NF-Y) based on the amino acid sequence from position 61 to position 125 with a bit score of 76.88 and an e-value of 2.85e-19 and recruits to pfam00125 (core histone H2A/H2B/H3/H4) archaeal histone due to the domain from amino acid 61 to amino acid 125, with a bit score of 51.39 and an e-value of 6.49e-10.

EUKT1490 (SEQ ID NO:67) encodes a polypeptide (SEQ ID NO:68) having a COG5208 (CCAAT-binding factor, subunit C) domain corresponding to amino acid residues 116 to 199 of the protein, identifying EUKT1490 as an NF-YC polypeptide (also called a CBF (CCAAT-binding factor) subunit C or HAP5 polypeptide) and a COG2036 (Histones H3 and H4) domain extending from amino acid 114 to amino acid 178. The EUKT1490 polypeptide (SEQ ID NO:68) also recruits to pfam00808 (histone-like transcription factor (CBF/NF-Y) and archaeal histone) due to the domain from amino acid 120 to amino acid 181, and pfam00125 based on the amino acid sequence from 115-182.

Example 10

Identification of Interacting Subunit NF-YA-1257

Figure 8:
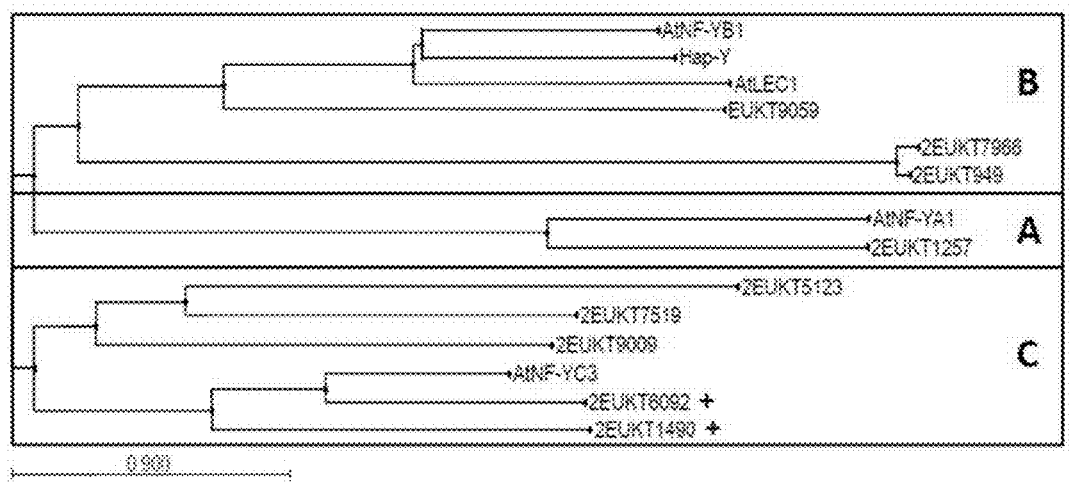
FIG. 8 is a diagram showing the relatedness of NF-Y

The Y2H screen was successful at revealing two NF-Y C subunits (EUKT6092 (SEQ ID NO:64, encoded by SEQ ID NO:63) and EUKT1490 (SEQ ID NO:68, encoded by SEQ ID NO:67)) capable of forming a heterodimer with Hap-1742, but failed to reveal the third member of the heterotrimer complex (subunit A). In order to find the missing A subunit of the Hap-1742 transcription factor complex, the *Nannochloropsis* genome was bioinformatically mined for NF-Y transcription factors. Five NF-Y C subunits, 4 NF-Y B subunits and only 1 NF-Y subunit A (EUKT1257, NF-YA-1257) were identified in the genome of WT-03730 (FIG. 8). EUKT1257 (SEQ ID NO:69) encodes a polypeptide (SEQ ID NO:70) that recruits to pfam02045 (CCAAT-binding transcription factor subunit B (CBF-B/NF-YA)) with a bit score of 103.55 and and e value of 4.62e-28. The polypeptide also includes a COG5224 (CCAAT-binding factor, subunit B) domain corresponding to amino acid residues 136 to 196 of the protein and a smart00521 (CCAAT-binding transcription factor) domain extending from amino acid 136 to amino acid 194. As the B subunit of CBF is an alternative name for the A subunit of NF-Y, we had identified an A subunit of an NF-Y complex. Given that there was only one NF-Y subunit A in *Nannochloropsis*, we hypothesized that it was capable of binding to Hap-1742. To test our hypothesis, NF-YA-1257 was cloned into a prey vector suitable for Y2H and tested against the Hap-1742 bait strain.

The open reading frame of NF-YA-1257 was amplified from cDNA using forward primer JLC-pGAD-1257-F (5'-ggaggccagtgaattcc<u>atggatggagctgagacggggag</u>-3';

SEQ ID NO: 73)

and reverse primer MC-pGAD-1257-R (5'-cgagctcgatggatcc<u>ctagatgataggcgaggatgag</u>-3';

SEQ ID NO: 74).

It was cloned into the prey vector pGADT7 (Clontech) by cpec and transformed into *E. coli*. After sequence verification it was transformed into yeast strain Y2HGold and was tested for interaction with Hap-1742 by mating with the Hap-1742 bait strain as described above.

The resulting hybrid yeast cells turned blue on plates with selective media while the appropriate controls did not, indicating a positive interaction between Hap-1742 and NF-YA-1257. Therefore, NF-YA-1257 specifically bound Hap-1742 (the B subunit) and it is highly likely that we have identified the entire transcription factor heterocomplex for Hap-1742.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

What is claimed is:

1. A recombinant microorganism comprising a non-native nucleic acid molecule encoding a non-LEC1-type HAP3-like polypeptide having at least 90% sequence identity to the polypeptide sequence selected from the group consisting of SEQ ID NO:6, SEQ ID NO:10, SEQ ID NO:12, SEQ ID NO:16, and SEQ ID NO:20, wherein expression of the non-native nucleic acid molecule in the recombinant microorganism produces increased biomass or lipid with respect to a control microorganism that does not include the non-native nucleic acid molecule encoding a non-LEC1-type HAP3-like polypeptide; further wherein the microorganism is an alga or heterokont.

2. The recombinant microorganism according to claim 1, wherein the non-LEC1-type HAP3-like polypeptide has at least 95% sequence identity to the polypeptide sequence selected from the group consisting of SEQ ID NO:6, SEQ ID NO:10, SEQ ID NO:12, SEQ ID NO:16, and SEQ ID NO:20.

3. The recombinant microorganism according to claim 1, wherein the non-LEC1-type HAP3-like polypeptide comprises the polypeptide sequence selected from the group consisting of SEQ ID NO:2, SEQ ID NO:3, SEQ ID NO:61, and SEQ ID NO:62.

4. The recombinant microorganism according to claim 1, wherein the non-LEC1-type HAP3-like polypeptide comprises an amino acid sequence having at least 90% sequence identity to the amino acid sequence of SEQ ID NO:4.

5. The recombinant microorganism according to claim 4, wherein the non-LEC1-type HAP3-like polypeptide comprises an amino acid sequence having at least 95% sequence identity to the amino acid sequence of SEQ ID NO:4.

6. The recombinant host cell microorganism according to claim 1, wherein the recombinant microorganism is a heterokont microorganism belonging to a genus selected from the group consisting of *Labryinthula, Labryinthuloides, Thraustochytrium, Schizochytrium, Aplanochytrium, Aurantiochytrium, Japonochytrium, Diplophrys,* and *Ulkenia*.

7. The recombinant microorganism according to claim 1, wherein said recombinant microorganism is an alga belonging to a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*.

8. The recombinant microorganism according to claim 7, wherein said alga belongs to a genus selected from the group consisting of *Chlorella, Cyclotella, Eustigmatos, Monodus, Nannochloropsis, Vischeria, Phæodactylum,* and *Tetraselmis*.

9. The recombinant microorganism according to claim 8, wherein said alga is a *Nannochloropsis* cell.

10. A microbial biomass comprising the recombinant microorganism of claim 1.

11. A method for producing a biomass or a lipid, comprising culturing the recombinant microorganism according to claim 1, and producing the biomass or the lipid therefrom.

12. The method of claim 11, wherein said recombinant microorganism is an alga.

13. The method of claim 12, wherein said alga belongs to a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phæodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*.

14. The method of claim 13, wherein said alga belongs to a genus selected from the group consisting of *Chlorella, Cyclotella, Eustigmatos, Monodus, Nannochloropsis, Phæodactylum, Vischeria,* and *Tetraselmis*.

15. The method of claim 14, wherein said alga is a *Nannochloropsis* cell.

16. The method of claim 12, wherein said culturing is under photoautotrophic conditions.

* * * * *

SEQUENCE LISTING

```
<160> NUMBER OF SEQ ID NOS: 76

<210> SEQ ID NO 1
<211> LENGTH: 7
<212> TYPE: PRT
<213> ORGANISM: Artificial Sequence
<220> FEATURE:
<223> OTHER INFORMATION: LEC1-type B domain motif

<400> SEQUENCE: 1
```

Met Pro Ile Ala Asn Val Ile
1               5

<210> SEQ ID NO 2
<211> LENGTH: 7
<212> TYPE: PRT
<213> ORGANISM: Artificial Sequence
<220> FEATURE:
<223> OTHER INFORMATION: non-LEC1-type B domain motif

<400> SEQUENCE: 2

Leu Pro Ile Ala Asn Ile Ser
1               5

<210> SEQ ID NO 3
<211> LENGTH: 7
<212> TYPE: PRT
<213> ORGANISM: Artificial Sequence
<220> FEATURE:
<223> OTHER INFORMATION: non-LEC1-type B domain motif

<400> SEQUENCE: 3

Leu Pro Ile Ala Asn Ile Ala
1               5

<210> SEQ ID NO 4
<211> LENGTH: 91
<212> TYPE: PRT
<213> ORGANISM: Nannochloropsis gaditana

<400> SEQUENCE: 4

Arg Glu Gln Asp Arg Tyr Leu Pro Ile Ala Asn Ile Ser Arg Ile Met
1               5                   10                  15

Lys Lys Ser Leu Pro Ala Asn Ala Lys Ile Ala Lys Asp Ala Lys Glu
            20                  25                  30

Thr Val Gln Glu Cys Val Ser Glu Phe Ile Ser Phe Ile Thr Ser Glu
        35                  40                  45

Ala Ser Asp Lys Cys Gln Gln Glu Lys Arg Lys Thr Ile Asn Gly Asp
    50                  55                  60

Asp Leu Leu Trp Ala Met Ser Thr Leu Gly Phe Asp Lys Tyr Val Glu
65                  70                  75                  80

Pro Leu Lys His Tyr Leu Val Lys Tyr Arg Glu
                85                  90

<210> SEQ ID NO 5
<211> LENGTH: 552
<212> TYPE: PRT
<213> ORGANISM: Nannochloropsis gaditana

<400> SEQUENCE: 5

Ala Thr Gly Gly Ala Thr Gly Ala Gly Gly Cys Gly Gly Ala Gly
1               5                   10                  15

Cys Cys Ala Ala Cys Gly Ala Gly Cys Ala Gly Gly Gly Gly
            20                  25                  30

Thr Cys Gly Thr Gly Thr Thr Gly Gly Thr Gly Gly Cys Gly Cys
        35                  40                  45

Gly Gly Cys Gly Thr Gly Gly Ala Gly Gly Gly Thr Cys Cys
    50                  55                  60

Gly Gly Gly Ala Ala Cys Ala Ala Gly Ala Cys Ala Gly Ala Thr Ala
65                  70                  75                  80

-continued

```
Thr Thr Thr Gly Cys Cys Cys Ala Thr Thr Gly Cys Cys Ala Ala Cys
                85                  90                  95

Ala Thr Cys Ala Gly Thr Cys Gly Gly Ala Thr Ala Ala Thr Gly Ala
            100                 105                 110

Ala Gly Ala Ala Gly Thr Cys Thr Thr Thr Gly Cys Cys Gly Gly Cys
        115                 120                 125

Gly Ala Ala Thr Gly Cys Cys Ala Ala Ala Ala Thr Ala Gly Cys Cys
    130                 135                 140

Ala Ala Gly Gly Ala Cys Gly Cys Cys Ala Ala Ala Gly Ala Ala Ala
145                 150                 155                 160

Cys Cys Gly Thr Cys Cys Ala Ala Gly Ala Ala Thr Gly Thr Gly Thr
                165                 170                 175

Thr Thr Cys Ala Gly Ala Gly Thr Thr Cys Ala Thr Thr Thr Cys Thr
            180                 185                 190

Thr Thr Cys Ala Thr Cys Ala Cys Cys Thr Cys Cys Gly Ala Ala Gly
        195                 200                 205

Cys Cys Ala Gly Cys Gly Ala Cys Ala Ala Ala Thr Gly Cys Cys Ala
    210                 215                 220

Ala Cys Ala Gly Gly Ala Gly Ala Ala Gly Cys Gly Ala Ala Ala Gly
225                 230                 235                 240

Ala Cys Gly Ala Thr Cys Ala Ala Cys Gly Gly Gly Gly Ala Cys Gly
                245                 250                 255

Ala Thr Cys Thr Cys Cys Thr Cys Thr Gly Gly Gly Cys Cys Ala Thr
            260                 265                 270

Gly Ala Gly Cys Ala Cys Cys Cys Thr Gly Gly Gly Cys Thr Thr Cys
        275                 280                 285

Gly Ala Cys Ala Ala Ala Thr Ala Cys Gly Thr Cys Gly Ala Gly Cys
    290                 295                 300

Cys Thr Cys Thr Gly Ala Ala Ala Cys Ala Thr Thr Ala Thr Thr Thr
305                 310                 315                 320

Gly Gly Thr Cys Ala Ala Gly Thr Ala Cys Cys Gly Thr Gly Ala Gly
                325                 330                 335

Thr Cys Ala Gly Thr Gly Ala Ala Gly Gly Gly Gly Gly Gly Thr Gly
            340                 345                 350

Ala Gly Ala Ala Gly Gly Cys Gly Gly Ala Cys Gly Gly Ala Gly Gly
        355                 360                 365

Gly Ala Ala Gly Ala Ala Ala Gly Gly Gly Ala Ala Gly Thr Cys Thr
    370                 375                 380

Gly Ala Gly Gly Gly Cys Ala Cys Cys Cys Ala Ala Gly Thr Gly Ala
385                 390                 395                 400

Cys Ala Gly Gly Ala Ala Gly Thr Ala Gly Cys Gly Cys Gly Gly Cys
                405                 410                 415

Gly Gly Gly Thr Cys Cys Thr Gly Thr Cys Ala Cys Gly Gly Cys Gly
            420                 425                 430

Ala Cys Cys Gly Cys Gly Cys Thr Ala Gly Cys Thr Gly Ala Gly Cys
        435                 440                 445

Cys Thr Cys Ala Gly Gly Gly Thr Gly Ala Cys Ala Gly Thr Cys Gly
    450                 455                 460

Gly Gly Thr Gly Gly Ala Ala Thr Cys Gly Ala Cys Cys Gly Ala Ala
465                 470                 475                 480

Ala Gly Cys Ala Gly Thr Ala Gly Thr Cys Thr Cys Cys Cys Cys Gly
                485                 490                 495

Ala Gly Cys Ala Gly Cys Ala Ala Cys Ala Thr Cys Ala Cys Ala Gly
```

```
                500             505             510
Thr Thr Ala Thr Gly Cys Ala Gly Cys Cys Cys Gly Thr Gly Cys Thr
                515             520             525
Gly Thr Gly Thr Cys Ala Ala Gly Gly Cys Ala Gly Cys Cys Gly Cys
                530             535             540
Cys Thr Thr Cys Cys Thr Gly Ala
545                 550

<210> SEQ ID NO 6
<211> LENGTH: 183
<212> TYPE: PRT
<213> ORGANISM: Nannochloropsis gaditana

<400> SEQUENCE: 6

Met Asp Glu Ala Gly Ala Asn Glu Ala Gly Gly Arg Val Gly Gly Ala
1               5                   10                  15
Gly Val Glu Glu Val Arg Glu Gln Asp Arg Tyr Leu Pro Ile Ala Asn
                20                  25                  30
Ile Ser Arg Ile Met Lys Lys Ser Leu Pro Ala Asn Ala Lys Ile Ala
            35                  40                  45
Lys Asp Ala Lys Glu Thr Val Gln Glu Cys Val Ser Glu Phe Ile Ser
50                  55                  60
Phe Ile Thr Ser Glu Ala Ser Asp Lys Cys Gln Gln Glu Lys Arg Lys
65                  70                  75                  80
Thr Ile Asn Gly Asp Asp Leu Leu Trp Ala Met Ser Thr Leu Gly Phe
                85                  90                  95
Asp Lys Tyr Val Glu Pro Leu Lys His Tyr Leu Val Lys Tyr Arg Glu
                100                 105                 110
Ser Val Lys Gly Gly Glu Lys Ala Asp Gly Gly Lys Lys Gly Lys Ser
            115                 120                 125
Glu Gly Thr Gln Val Thr Gly Ser Ser Ala Ala Gly Pro Val Thr Ala
130                 135                 140
Thr Ala Leu Ala Glu Pro Gln Gly Asp Ser Arg Val Glu Ser Thr Glu
145                 150                 155                 160
Ser Ser Ser Leu Pro Glu Gln Gln His His Ser Tyr Ala Ala Arg Ala
                165                 170                 175
Val Ser Arg Gln Pro Pro Ser
            180

<210> SEQ ID NO 7
<211> LENGTH: 714
<212> TYPE: DNA
<213> ORGANISM: Nannochloropsis oceanica

<400> SEQUENCE: 7
atgaagaagc aagaacagaa taatgacccct cacgcacccc ccctccaaca gcacaggcag      60
gctcactcga gcgggaaaag gaggtgcaca gctatggaag aaacgggtgg ctacgaaatg     120
ggcggaggcg gaggaggtgg cgccggaggg ggcggggggag gggatgaggt cagggagcag     180
gaccgatact tgcccatagc caacatcagt cgaatcatga agaagtctct gcccgccaat     240
gccaagatcg ccaaggacgc caaggaaact gtacaagaat gtgtttcaga attcatctcc     300
ttcatcacgt cggaagccag tgacaaatgt caacaagaga acgcaagac tatcaacggc     360 gacgaccttc tttgggccat gagcaccctt ggctttgata aatacgtcga gccccttaag     420
ctctacctgg tgaagtatcg tgaatccgtc aaaggtggcg aaaaatcaga tggagggaaa     480
```

```
aaaggcaagg ctggagggga ggaggcgagc gcgtcggtta ccacgggcag cagtgcagcg    540
gcgcctgtca ccgcgagtgc ttcaggtagt ggtggaggag gagcgggcat ggtgatgagc    600
gggtcagcat cggaacaagc aacagtgcag caacagcaac agcaacaaca cgcagcttac    660
caactgccgc ctgtagggca agagcagcag cccgctccgt cttcggggcc ttaa          714
```

<210> SEQ ID NO 8
<211> LENGTH: 183
<212> TYPE: PRT
<213> ORGANISM: Nannochloropsis gaditana

<400> SEQUENCE: 8

```
Met Asp Glu Ala Gly Ala Asn Glu Ala Gly Gly Arg Val Gly Gly Ala
1               5                   10                  15

Gly Val Glu Glu Val Arg Glu Gln Asp Arg Tyr Leu Pro Ile Ala Asn
            20                  25                  30

Ile Ser Arg Ile Met Lys Lys Ser Leu Pro Ala Asn Ala Lys Ile Ala
        35                  40                  45

Lys Asp Ala Lys Glu Thr Val Gln Glu Cys Val Ser Glu Phe Ile Ser
    50                  55                  60

Phe Ile Thr Ser Glu Ala Ser Asp Lys Cys Gln Gln Glu Lys Arg Lys
65                  70                  75                  80

Thr Ile Asn Gly Asp Asp Leu Leu Trp Ala Met Ser Thr Leu Gly Phe
                85                  90                  95

Asp Lys Tyr Val Glu Pro Leu Lys His Tyr Leu Val Lys Tyr Arg Glu
            100                 105                 110

Ser Val Lys Gly Gly Glu Lys Ala Asp Gly Gly Lys Lys Gly Lys Ser
        115                 120                 125

Glu Gly Thr Gln Val Thr Gly Ser Ser Ala Ala Gly Pro Val Thr Ala
    130                 135                 140

Thr Ala Leu Ala Glu Pro Gln Gly Asp Ser Arg Val Glu Ser Thr Glu
145                 150                 155                 160

Ser Ser Ser Leu Pro Glu Gln His His Ser Tyr Ala Ala Arg Ala
                165                 170                 175

Val Ser Arg Gln Pro Pro Ser
            180
```

<210> SEQ ID NO 9
<211> LENGTH: 404
<212> TYPE: DNA
<213> ORGANISM: Tetraselmis sp.

<400> SEQUENCE: 9

```
tgagcaacgg gcgggacaag cggcctgtgg aggaggacga tgacggcgac gacaagcata     60
gcgtgcgcga gcaggaccgc ttcctgccca tcgcaaacat cagccggatc atgaaaaagg    120
cgctgccccc caacgccaag attgccaagg acgcgaagga cggtgcag gagtgcgtct      180 cggagttcat cagcttcatc accagcgagg cgagcgacaa gtgccagcga gaagaggaa    240 aaacgattaa cggcgacgac ttgctgtggg ctatgaccac actgggcttc gaggactacg    300
tggagccgct caaggtgtac ttagccaagt tccgggagag cgagaaggca gagggcgaga    360
aggcggctgc ggagaaggga gagggcacca gcgcccagga ttga                     404
```

<210> SEQ ID NO 10
<211> LENGTH: 134
<212> TYPE: PRT
<213> ORGANISM: Tetraselmis sp.

```
<400> SEQUENCE: 10

Met Ser Asn Gly Arg Asp Lys Arg Pro Val Glu Glu Asp Asp Gly
1               5                   10                  15

Asp Asp Lys His Ser Val Arg Glu Gln Asp Arg Phe Leu Pro Ile Ala
            20                  25                  30

Asn Ile Ser Arg Ile Met Lys Lys Ala Leu Pro Pro Asn Ala Lys Ile
        35                  40                  45

Ala Lys Asp Ala Lys Glu Thr Val Gln Glu Cys Val Ser Glu Phe Ile
    50                  55                  60

Ser Phe Ile Thr Ser Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Val Tyr Leu Ala Lys Phe Arg
            100                 105                 110

Glu Ser Glu Lys Ala Gly Glu Lys Ala Ala Ala Glu Lys Gly Glu
        115                 120                 125

Gly Thr Ser Ala Gln Asp
        130

<210> SEQ ID NO 11
<211> LENGTH: 395
<212> TYPE: DNA
<213> ORGANISM: Tetraselmis sp.

<400> SEQUENCE: 11
tgagcaacag caacggcaag cgcgcggtag acgaggagga ggagtacgac ggtgacaggc      60
acagcgtcag ggagcaggac aggttccttc caatcgccaa cattagccgc atcatgaaga     120
aggccttgcc accaaacgca aaaattgcca aggacgccaa ggagaccgtc caggaatgcg     180
tctccgagtt catcagtttt attaccagcg aagctagcga taagtgccag agggagaaga     240
ggaaaaccat caacggagat gacttgcttt gggccatgag cacgcttggg tttgaggact     300
acgtggagcc actcaaggtt tacctcgcaa agttcagaga gagcgagaag gcagagggtg     360
agaaagctgc tctggagaag ggggaggccg agtaa                                395

<210> SEQ ID NO 12
<211> LENGTH: 131
<212> TYPE: PRT
<213> ORGANISM: Tetraselmis sp.

<400> SEQUENCE: 12

Met Ser Asn Ser Asn Gly Lys Arg Ala Val Asp Glu Glu Glu Tyr
1               5                   10                  15

Asp Gly Asp Arg His Ser Val Arg Glu Gln Asp Arg Phe Leu Pro Ile
            20                  25                  30

Ala Asn Ile Ser Arg Ile Met Lys Lys Ala Leu Pro Pro Asn Ala Lys
        35                  40                  45

Ile Ala Lys Asp Ala Lys Glu Thr Val Gln Glu Cys Val Ser Glu Phe
    50                  55                  60

Ile Ser Phe Ile Thr Ser Glu Ala Ser Asp Lys Cys Gln Arg Glu Lys
65                  70                  75                  80

Arg Lys Thr Ile Asn Gly Asp Asp Leu Leu Trp Ala Met Ser Thr Leu
                85                  90                  95

Gly Phe Glu Asp Tyr Val Glu Pro Leu Lys Val Tyr Leu Ala Lys Phe
```

```
            100                 105                 110
Arg Glu Ser Glu Lys Ala Glu Gly Glu Lys Ala Ala Leu Glu Lys Gly
        115                 120                 125

Glu Ala Glu
    130

<210> SEQ ID NO 13
<211> LENGTH: 396
<212> TYPE: DNA
<213> ORGANISM: Tetraselmis sp.

<400> SEQUENCE: 13
atgagcaaca gcaacggcaa ccgctcgggc gatgaggagg aggagtacga tggtgacagg      60
cacagcgtca gggagcagga caggttcctt ccgatcgcca acattagccg catcatgaag     120
aaggccttgc cacctaacgc aaagattgcc aaggacgcca aggagaccgt ccaggaatgc     180
gtctccgagt tcatcagttt tattaccagc gaagctagcg acaagtgcca gagggagaag     240
aggaaaacca tcaacggaga tgacttgctt tgggctatga gtacgctggg gttcgaggac     300
tacgtggagc cactcaaggt ttacctcgca aagttcagag agagcgagaa ggcagagggc     360
gagaaagctg ctctggagaa ggggaggcc gagtaa                                396

<210> SEQ ID NO 14
<211> LENGTH: 131
<212> TYPE: PRT
<213> ORGANISM: Tetraselmis sp.

<400> SEQUENCE: 14

Met Ser Asn Ser Asn Gly Asn Arg Ser Gly Asp Glu Glu Glu Glu Tyr
1               5                   10                  15

Asp Gly Asp Arg His Ser Val Arg Glu Gln Asp Arg Phe Leu Pro Ile
            20                  25                  30

Ala Asn Ile Ser Arg Ile Met Lys Lys Ala Leu Pro Pro Asn Ala Lys
        35                  40                  45

Ile Ala Lys Asp Ala Lys Glu Thr Val Gln Glu Cys Val Ser Glu Phe
    50                  55                  60

Ile Ser Phe Ile Thr Ser Glu Ala Ser Asp Lys Cys Gln Arg Glu Lys
65                  70                  75                  80

Arg Lys Thr Ile Asn Gly Asp Asp Leu Leu Trp Ala Met Ser Thr Leu
                85                  90                  95

Gly Phe Glu Asp Tyr Val Glu Pro Leu Lys Val Tyr Leu Ala Lys Phe
            100                 105                 110

Arg Glu Ser Glu Lys Ala Glu Gly Glu Lys Ala Ala Leu Glu Lys Gly
        115                 120                 125

Glu Ala Glu
    130

<210> SEQ ID NO 15
<211> LENGTH: 570
<212> TYPE: DNA
<213> ORGANISM: Cyclotella sp.

<400> SEQUENCE: 15
atggcgcatc aacaacacca aaaacagcaa cagcaacagc aacagcagca atacacaaac      60
tatccaccgt cggaatcagc tgcaccccg ccatctctct cgaacacagc acaagatttc     120
caacacgctg ccggattgag agatcatgat tccaatgtgc tggagcagga tcgctacctc     180
```

```
cccatagcca acatagcccg cataatgaaa acaccctcc ccgaaaacgc caaaatcgcc      240
aaagactcca aagaaacagt ccaagaatgc gtctccgaat tcatatcatt catcacctcc      300
gaggcctcgg acaaatgcat gcaagagaaa cgaaagacga tcaatggcga tgacttgttg      360
tgggccatga gtactttggg gttcgataag tacgtcgagc ctttgaaggt ttatttggcc      420
aagtataggg aggccgtgag gggggaaaag ccggagaagg tggggaccgt ggggagtttg      480
gtggggaggc cgccggctat ggcgagtatg gcaggtgaag gcgtgggagt gagtagcaga      540
ccggggaaaa aggcaaaaca caatggttga                                       570
```

<210> SEQ ID NO 16
<211> LENGTH: 189
<212> TYPE: PRT
<213> ORGANISM: Cyclotella sp.

<400> SEQUENCE: 16

```
Met Ala His Gln Gln His Gln Lys Gln Gln Gln Gln Gln Gln Gln Gln
1               5                   10                  15

Gln Tyr Thr Asn Tyr Pro Pro Ser Glu Ser Ala Ala Pro Pro Pro Ser
            20                  25                  30

Leu Ser Asn Thr Ala Gln Asp Phe Gln His Ala Ala Gly Leu Arg Asp
        35                  40                  45

His Asp Ser Asn Val Leu Glu Gln Asp Arg Tyr Leu Pro Ile Ala Asn
    50                  55                  60

Ile Ala Arg Ile Met Lys Asn Thr Leu Pro Glu Asn Ala Lys Ile Ala
65                  70                  75                  80

Lys Asp Ser Lys Glu Thr Val Gln Glu Cys Val Ser Glu Phe Ile Ser
                85                  90                  95

Phe Ile Thr Ser Glu Ala Ser Asp Lys Cys Met Gln Glu Lys Arg Lys
            100                 105                 110

Thr Ile Asn Gly Asp Asp Leu Leu Trp Ala Met Ser Thr Leu Gly Phe
        115                 120                 125

Asp Lys Tyr Val Glu Pro Leu Lys Val Tyr Leu Ala Lys Tyr Arg Glu
    130                 135                 140

Ala Val Arg Gly Glu Lys Pro Glu Lys Val Gly Thr Val Gly Ser Leu
145                 150                 155                 160

Val Gly Arg Pro Pro Ala Met Ala Ser Met Ala Gly Glu Gly Val Gly
                165                 170                 175

Val Ser Ser Arg Pro Gly Lys Lys Ala Lys His Asn Gly
            180                 185
```

<210> SEQ ID NO 17
<211> LENGTH: 393
<212> TYPE: DNA
<213> ORGANISM: Navicula sp.

<400> SEQUENCE: 17

```
atgtcagaca tggatacagg aaaaggccat cttggcgatg agttcgaaga aattcgagag      60
caggatcgct atctaccaat cgcgaatatt gcccggatca tgaaaaacac acttccggag     120
aatgcgaaaa tcgccaaaga ttccaaagag acagtccagg aatgtgtttc ggaatttatt     180
tcgttcatca catccgaagc cagcgataag tgcttacagg aaaagagaaa gactatcaat     240
ggagatgatc tgctctgggc aatgtcgacc ttggggttcg ataagtacgt agagccattg     300
aagctgtatt taggaaagta tcgggacgcg gtccgagggg ataagccaga gaagacgggt     360
cgacctggaa tggggacgga tgactctgtc tag                                   393
```

<210> SEQ ID NO 18
<211> LENGTH: 189
<212> TYPE: PRT
<213> ORGANISM: Navicula sp.

<400> SEQUENCE: 18

Met Ala His Gln Gln His Gln Lys Gln Gln Gln Gln Gln Gln Gln
1               5                   10                  15

Gln Tyr Thr Asn Tyr Pro Pro Ser Glu Ser Ala Ala Pro Pro Ser
            20                  25                  30

Leu Ser Asn Thr Ala Gln Asp Phe Gln His Ala Ala Gly Leu Arg Asp
        35                  40                  45

His Asp Ser Asn Val Leu Glu Gln Asp Arg Tyr Leu Pro Ile Ala Asn
    50                  55                  60

Ile Ala Arg Ile Met Lys Asn Thr Leu Pro Glu Asn Ala Lys Ile Ala
65                  70                  75                  80

Lys Asp Ser Lys Glu Thr Val Gln Glu Cys Val Ser Glu Phe Ile Ser
                85                  90                  95

Phe Ile Thr Ser Glu Ala Ser Asp Lys Cys Met Gln Glu Lys Arg Lys
            100                 105                 110

Thr Ile Asn Gly Asp Asp Leu Leu Trp Ala Met Ser Thr Leu Gly Phe
        115                 120                 125

Asp Lys Tyr Val Glu Pro Leu Lys Val Tyr Leu Ala Lys Tyr Arg Glu
    130                 135                 140

Ala Val Arg Gly Glu Lys Pro Glu Lys Val Gly Thr Val Gly Ser Leu
145                 150                 155                 160

Val Gly Arg Pro Pro Ala Met Ala Ser Met Ala Gly Glu Gly Val Gly
                165                 170                 175

Val Ser Ser Arg Pro Gly Lys Lys Ala Lys His Asn Gly
            180                 185

<210> SEQ ID NO 19
<211> LENGTH: 399
<212> TYPE: DNA
<213> ORGANISM: Chlorella sp.

<400> SEQUENCE: 19
atgagcggag acgtctctgg ggatgaggga ggagtaaacg ttagggagca ggacaggttt      60
cttccaatag ccaatatcag ccgaataatg aagaggaatc ttccgggcaa tgcaaagata     120
gcgaaagatg ccaaggaaac tgtccaggag tgcgtttctg agtttatcag ctttatcaca     180
agcgaggcta gcgacaaatg tcaaggggag aagcggaaaa ccatcaatgg ggacgacctt     240
ttgtgggcta tgagcacgct gggctttgag gagtacatcg agcccctgaa aatatatctt     300
gcaaaattta gagagagtga aagcaggcg ctggccgctc aaggaggcgg aaagactggg      360
ggctcggacg cgcggcatga ggccaattcc tatcagtag                            399

<210> SEQ ID NO 20
<211> LENGTH: 171
<212> TYPE: PRT
<213> ORGANISM: Chlorella sp.

<400> SEQUENCE: 20

Met Ala Glu Val Pro Thr Ser Pro Pro Gly Gly Asn Asp Ser Gly Gly
1               5                   10                  15

Glu Gln Ser Pro Gln Asn Gly Ser Ser Ser Ser Val Arg Glu Gln Asp

```
            20                  25                  30
Arg Tyr Leu Pro Ile Ala Asn Ile Ser Arg Ile Met Lys Lys Ala Leu
                35                  40                  45

Pro Gln Asn Gly Lys Ile Ala Lys Asp Ala Lys Asp Thr Val Gln Glu
         50                  55                  60

Cys Val Ser Glu Phe Ile Ser Phe Val Thr Ser Glu Ala Ser Asp Lys
 65                  70                  75                  80

Cys Gln Lys Glu Lys Arg Lys Thr Ile Asn Gly Asp Asp Leu Leu Trp
                 85                  90                  95

Ala Met Ala Thr Leu Gly Phe Glu Asp Tyr Ile Glu Pro Leu Arg Ile
                100                 105                 110

Tyr Leu Ala Arg Tyr Arg Glu Gly Asp Ala Lys Gly Ser Ala Arg Gly
            115                 120                 125

Gly Glu Gly Ser Ala Lys Gly Asn Pro Val Gly Ala Met Pro Gly Gln
        130                 135                 140

Asn Ser Gln Phe Val His Gln Pro Pro Leu Asn Tyr Val Asn Ser Gln
145                 150                 155                 160

Ala Gln His Leu Gly Ser Phe Tyr Ala Lys Leu
                165                 170

<210> SEQ ID NO 21
<211> LENGTH: 453
<212> TYPE: DNA
<213> ORGANISM: Botryococcus braunii

<400> SEQUENCE: 21
atgagtgggg ccgatgggga cgggcgagac gacggagatg agcgtgcggt gcgagagcag      60
gatcgattcc tccccatcgc aaacatcagt aggataatga aaaaggcgct gcctgccaac     120
gccaagatcg cgaaggacgc caaggaaacg gtgcaggagt gcgtgtcgga gtttatcagc     180
ttcatcacga gcgaggcgag tgacaagtgc cagcgggaaa agcggaagac catcaacggg     240
gacgatctgt tgtgggccat gagcaccctg ggctttgaag actacgtaga acctctgaag     300
ctgtacctgc acaagtaccg agaggggaa aaggcgagtc tcgccaagca agctggcgga     360
gctggcggtg ggtcttctgc agaggccaaa agggatactc gggaagagat gacgtacatg     420
ccagcaaaca tgtacatgcc gcagcaacgc tag                                   453

<210> SEQ ID NO 22
<211> LENGTH: 150
<212> TYPE: PRT
<213> ORGANISM: Botryococcus braunii

<400> SEQUENCE: 22

Met Ser Gly Ala Asp Gly Asp Gly Arg Asp Asp Gly Asp Glu Arg Ala
  1               5                  10                  15

Val Arg Glu Gln Asp Arg Phe Leu Pro Ile Ala Asn Ile Ser Arg Ile
             20                  25                  30

Met Lys Lys Ala Leu Pro Ala Asn Ala Lys Ile Ala Lys Asp Ala Lys
         35                  40                  45

Glu Thr Val Gln Glu Cys Val Ser Glu Phe Ile Ser Phe Ile Thr Ser
    50                   55                  60

Glu Ala Ser Asp Lys Cys Gln Arg Glu Lys Arg Lys Thr Ile Asn Gly
 65                  70                  75                  80

Asp Asp Leu Leu Trp Ala Met Ser Thr Leu Gly Phe Glu Asp Tyr Val
                 85                  90                  95
```

```
Glu Pro Leu Lys Leu Tyr Leu His Lys Tyr Arg Glu Gly Glu Lys Ala
                100                 105                 110
Ser Leu Ala Lys Gln Ala Gly Ala Gly Gly Ser Ser Ala Glu
        115                 120                 125
Ala Lys Arg Asp Thr Arg Glu Glu Met Thr Tyr Met Pro Ala Asn Met
    130                 135                 140
Tyr Met Pro Gln Gln Arg
145                 150

<210> SEQ ID NO 23
<211> LENGTH: 507
<212> TYPE: DNA
<213> ORGANISM: Fragilariopsis cylindrus

<400> SEQUENCE: 23
atggccgacc ttccttcaaa tgcagatgca atagctgatg ctaagatctc tcctggggat      60
gattacgaag agattagaga acaggaccgt tatttgccaa tagccaatat tgctcggata     120
atgaagaata cgttacctga aaatgccaaa atcgctaagg attccaaaga aacagtacag     180
gaatgcgtat cggaatttat aagctttatc acatcggaag catccgataa atgcctacag     240
gaaaaacgaa aaacaataaa tggagacgac ttgttatggg caatgtcaac tcttggattt     300
gataagtacg ttgagcctct caaactgtat ttgagcaagt acagagaagc agttcgtgga     360
gataaaccag acaaagcggc ggcaagggct agtgccaatg cagctagtgc tgccgctagt     420
gcagctaatg ctgctaatgc agttaatgct agtgcagcta gtgctaatgt taatgctggc     480
ggggtagctg gacaaactaa atcttaa                                         507

<210> SEQ ID NO 24
<211> LENGTH: 168
<212> TYPE: PRT
<213> ORGANISM: Fragilariopsis cylindrus

<400> SEQUENCE: 24

Met Ala Asp Leu Pro Ser Asn Ala Asp Ala Ile Ala Asp Ala Lys Ile
1               5                   10                  15
Ser Pro Gly Asp Asp Tyr Glu Glu Ile Arg Glu Gln Asp Arg Tyr Leu
            20                  25                  30
Pro Ile Ala Asn Ile Ala Arg Ile Met Lys Asn Thr Leu Pro Glu Asn
        35                  40                  45
Ala Lys Ile Ala Lys Asp Ser Lys Glu Thr Val Gln Glu Cys Val Ser
    50                  55                  60
Glu Phe Ile Ser Phe Ile Thr Ser Glu Ala Ser Asp Lys Cys Leu Gln
65                  70                  75                  80
Glu Lys Arg Lys Thr Ile Asn Gly Asp Asp Leu Leu Trp Ala Met Ser
                85                  90                  95
Thr Leu Gly Phe Asp Lys Tyr Val Glu Pro Leu Lys Leu Tyr Leu Ser
            100                 105                 110
Lys Tyr Arg Glu Ala Val Arg Gly Asp Lys Pro Asp Lys Ala Ala Ala
        115                 120                 125
Arg Ala Ser Ala Asn Ala Ala Ser Ala Ala Ser Ala Ala Asn Ala
    130                 135                 140
Ala Asn Ala Val Asn Ala Ser Ala Ala Ser Ala Asn Val Asn Ala Gly
145                 150                 155                 160
Gly Val Ala Gly Gln Thr Lys Ser
                165
```

<210> SEQ ID NO 25
<211> LENGTH: 516
<212> TYPE: DNA
<213> ORGANISM: Fragaria vesca

<400> SEQUENCE: 25

```
atggcggagg taccgacgag cccgccgggc ggtaacgaca gcggcggcga gcaaagcccg      60
cagaacggga gcagcagcag cgtgagggag caggacaggt acctcccaat cgcgaacatc     120
agccggatta tgaagaaggc gctgccgcag aacggcaaga tcgccaagga cgccaaggac     180
actgtccagg aatgcgtctc tgaattcatc agcttcgtca ccagcgaggc tagcgataag     240
tgtcagaagg agaagaggaa gacgattaat ggtgatgatt tgctgtgggc gatggctacg     300
ttagggtttg aggactatat tgagccgctc aggatttact tggctaggta cagggagggt     360
gatgcaaagg gttctgcgag gggtggagaa ggatctgcta aagggaatcc tgttggagct     420
atgcctgggc aaaattcaca gtttgttcat cagccaccct tgaactatgt caatagtcaa     480
gcacagcatt tgggctcatt ctatgcaaag ctatga                               516
```

<210> SEQ ID NO 26
<211> LENGTH: 171
<212> TYPE: PRT
<213> ORGANISM: Fragaria vesca

<400> SEQUENCE: 26

```
Met Ala Glu Val Pro Thr Ser Pro Pro Gly Gly Asn Asp Ser Gly Gly
1               5                   10                  15

Glu Gln Ser Pro Gln Asn Gly Ser Ser Ser Val Arg Glu Gln Asp
            20                  25                  30

Arg Tyr Leu Pro Ile Ala Asn Ile Ser Arg Ile Met Lys Lys Ala Leu
        35                  40                  45

Pro Gln Asn Gly Lys Ile Ala Lys Asp Ala Lys Asp Thr Val Gln Glu
    50                  55                  60

Cys Val Ser Glu Phe Ile Ser Phe Val Thr Ser Glu Ala Ser Asp Lys
65                  70                  75                  80

Cys Gln Lys Glu Lys Arg Lys Thr Ile Asn Gly Asp Asp Leu Leu Trp
                85                  90                  95

Ala Met Ala Thr Leu Gly Phe Glu Asp Tyr Ile Glu Pro Leu Arg Ile
            100                 105                 110

Tyr Leu Ala Arg Tyr Arg Glu Gly Asp Ala Lys Gly Ser Ala Arg Gly
        115                 120                 125

Gly Glu Gly Ser Ala Lys Gly Asn Pro Val Gly Ala Met Pro Gly Gln
    130                 135                 140

Asn Ser Gln Phe Val His Gln Pro Pro Leu Asn Tyr Val Asn Ser Gln
145                 150                 155                 160

Ala Gln His Leu Gly Ser Phe Tyr Ala Lys Leu
                165                 170
```

<210> SEQ ID NO 27
<211> LENGTH: 621
<212> TYPE: DNA
<213> ORGANISM: Fragaria vesca

<400> SEQUENCE: 27

```
atggcggaag gtccagcgag ccccggcggc ggcggagcc acgacagcgg cgagcacagt       60
ccccgatcga atgtccggga gcaggatcgg tatcttccga tcgcgaatat tagccggatt     120
```

```
atgaagaagg cgcttccggc gaacggtaag atcgctaagg atgcgaagga gactgtgcag    180
gagtgcgttt cagagttcat cagcttcatc accagcgagg cgagcgacaa gtgccagagg    240
gaaaagagga agacgattaa tggtgacgac ttgctttggg ctatggcgac tttaggtttc    300
gaagactaca ttgatcctct caaggtttac cttgcgaaat acagagagat ggagggtgac    360
accaagggtt caggcaaggg tggagactct tcttctaaga agaagctcca gccaagtgcc    420
attgctcaga ttcctcacca aggttctttc tctcaaggag ctacttactc aaattctcaa    480
acacttggtt tgctcccaag tgctctgggg tttgactctc tcccgttgtg tacccaccta    540
ttattgctag agtttccggc ttcccaaatg ttgtggggtc aggcaggaag cctatggatt    600
atcgggtcaa agatccctta g                                              621
```

<210> SEQ ID NO 28
<211> LENGTH: 206
<212> TYPE: PRT
<213> ORGANISM: Fragaria vesca

<400> SEQUENCE: 28

```
Met Ala Glu Gly Pro Ala Ser Pro Gly Gly Gly Ser His Asp Ser
1               5                  10                  15

Gly Glu His Ser Pro Arg Ser Asn Val Arg Glu Gln Asp Arg Tyr Leu
            20                  25                  30

Pro Ile Ala Asn Ile Ser Arg Ile Met Lys Lys Ala Leu Pro Ala Asn
        35                  40                  45

Gly Lys Ile Ala Lys Asp Ala Lys Glu Thr Val Gln Glu Cys Val Ser
    50                  55                  60

Glu Phe Ile Ser Phe Ile Thr Ser Glu Ala Ser Asp Lys Cys Gln Arg
65                  70                  75                  80

Glu Lys Arg Lys Thr Ile Asn Gly Asp Asp Leu Leu Trp Ala Met Ala
                85                  90                  95

Thr Leu Gly Phe Glu Asp Tyr Ile Asp Pro Leu Lys Val Tyr Leu Ala
            100                 105                 110

Lys Tyr Arg Glu Met Glu Gly Asp Thr Lys Gly Ser Gly Lys Gly Gly
        115                 120                 125

Asp Ser Ser Lys Lys Glu Ala Gln Pro Ser Ala Ile Ala Gln Ile
    130                 135                 140

Pro His Gln Gly Ser Phe Ser Gln Gly Ala Thr Tyr Ser Asn Ser Gln
145                 150                 155                 160

Thr Leu Gly Leu Leu Pro Ser Ala Leu Gly Phe Asp Ser Leu Pro Leu
                165                 170                 175

Cys Thr His Leu Leu Leu Glu Phe Pro Ala Ser Gln Met Leu Trp
            180                 185                 190

Gly Gln Ala Gly Ser Leu Trp Ile Ile Gly Ser Lys Ile Pro
        195                 200                 205
```

<210> SEQ ID NO 29
<211> LENGTH: 645
<212> TYPE: DNA
<213> ORGANISM: Fragaria vesca

<400> SEQUENCE: 29

```
atggccgact cggacaacga ctccggcggc cacaacggcc actcgcaggg cggtgagctc     60
tcggcgcgtg agcaggaccg gttcctcccg atcgcgaacg tcagccgcat catgaagaag    120
gcattgccgg cgaacgccaa gatctccaag gacgccaaag agaccgtgca ggagtgcgtc    180
```

-continued

```
tccgagttca tcagcttcgt caccggcgag gcctccgaca agtgccagcg cgagaagcgc      240
aagaccatca acggcgacga tctcctctgg gccatgacca ccttgggatt cgaggagtac      300
gtcgagcccc tcaagatcta tctccagaag taccgcgaga tggagggcga aaaggcgcc       360 gccgtcggaa ccgccggtcg cgacaaggac ggcggctccg cggcggagg atcggctgca       420 ggcggcggcg gcggcggggg aggaggaagt agcggaggcg gattgagctc cgggaccagc      480
ggaggaggcg gcgcgtttaa tggtgtttat ggcgggatgg gaatgctagg tcatcatcag      540
ggacacgtgt acggctcggg cgggtatcaa catcaaatgg gagttggagt tggagcggag      600
aagcgcagtg gttccggcgg cggagcttcg gtgaggtcaa ggtag                      645
```

```
<210> SEQ ID NO 30
<211> LENGTH: 214
<212> TYPE: PRT
<213> ORGANISM: Fragaria vesca

<400> SEQUENCE: 30
```

Met Ala Asp Ser Asp Asn Asp Ser Gly Gly His Asn Gly His Ser Gln
1               5                   10                  15

Gly Gly Glu Leu Ser Ala Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Val Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Glu Tyr Val Glu Pro Leu Lys Ile Tyr Leu Gln Lys Tyr Arg
            100                 105                 110

Glu Met Glu Gly Glu Lys Gly Ala Ala Val Gly Thr Ala Gly Arg Asp
        115                 120                 125

Lys Asp Gly Gly Ser Gly Gly Gly Ser Ala Ala Gly Gly Gly Gly
    130                 135                 140

Gly Gly Gly Gly Ser Ser Gly Gly Leu Ser Ser Gly Thr Ser
145                 150                 155                 160

Gly Gly Gly Gly Ala Phe Asn Gly Val Tyr Gly Met Gly Met Leu
                165                 170                 175

Gly His His Gln Gly His Val Tyr Gly Ser Gly Tyr Gln His Gln
            180                 185                 190

Met Gly Val Gly Val Gly Ala Glu Lys Arg Ser Gly Ser Gly Gly
        195                 200                 205

Ala Ser Val Arg Ser Arg
    210

```
<210> SEQ ID NO 31
<211> LENGTH: 654
<212> TYPE: DNA
<213> ORGANISM: Fragaria vesca

<400> SEQUENCE: 31
```

```
atgagtggaa aaagaaacca aaccagcccg gttggaagcc ctttatccgg tgggaatgta      60
tccgacggcg gttccaaaga gcaagacagg ttcctcccca ttgctaatgt gagccggatc      120
atgaagaagt ccctccctgc aaatgccaag atttcaaagg aagccaagga aactgtccaa      180
```

```
gaatgcgtct ccgaattcat tagcttcatc actggggaag cctcggacaa gtgccaacga    240
gagaagagga agactatcaa tggcgatgat cttctttggg ccatgacaac tcttggtttt    300
gagaactatg ttggacccct tgaaggccat ctcaacaagt acagagaaac tgagggcgag    360
```
(Note: second occurrence — actual: `gagaactatg ttggacccct tgaagggcta tctcaacaagt acagagaaac tgagggcgag`)

```
gaatgcgtct ccgaattcat tagcttcatc actggggaag cctcggacaa gtgccaacga    240
gagaagagga agactatcaa tggcgatgat cttctttggg ccatgacaac tcttggtttt    300
gagaactatg ttggacccct tgaagggcta tctcaacaagt acagagaaac tgagggcgag    360
aagaactcca tggctagagg acaagaagat caagaccact cgtctcatga tgatcatcac    420
atcaacaaca acaagaagca actccaaaat ggtgctaatg ggatcaacac agtaggaact    480
aataaggtgg atcttctcag taatattggt ggattttatt cacttggagg acaacagatg    540
agtgctccaa aggcgtttgg agagagtgga agggttattg actatgggga tcagaatttg    600
atgacttatg gggatggaag tgcaaatcat cttcacaatg ggataggatg gtaa           654
```

<210> SEQ ID NO 32
<211> LENGTH: 217
<212> TYPE: PRT
<213> ORGANISM: Fragaria vesca

<400> SEQUENCE: 32

```
Met Ser Gly Lys Arg Asn Gln Thr Ser Pro Val Gly Ser Pro Leu Ser
 1               5                  10                  15

Gly Gly Asn Val Ser Asp Gly Ser Lys Glu Gln Asp Arg Phe Leu
            20                  25                  30

Pro Ile Ala Asn Val Ser Arg Ile Met Lys Lys Ser Leu Pro Ala Asn
        35                  40                  45

Ala Lys Ile Ser Lys Glu Ala Lys Glu Thr Val Gln Glu Cys Val Ser
    50                  55                  60

Glu Phe Ile Ser Phe Ile Thr Gly Glu Ala Ser Asp Lys Cys Gln Arg
 65                  70                  75                  80

Glu Lys Arg Lys Thr Ile Asn Gly Asp Asp Leu Leu Trp Ala Met Thr
                85                  90                  95

Thr Leu Gly Phe Glu Asn Tyr Val Gly Pro Leu Lys Gly Tyr Leu Asn
            100                 105                 110

Lys Tyr Arg Glu Thr Glu Gly Glu Lys Asn Ser Met Ala Arg Gly Gln
        115                 120                 125

Glu Asp Gln Asp His Ser His Asp His Ile Asn Asn
    130                 135                 140

Lys Lys Gln Leu Gln Asn Gly Ala Asn Gly Ile Asn Thr Val Gly Thr
145                 150                 155                 160

Asn Lys Val Asp Leu Leu Ser Asn Ile Gly Gly Phe Tyr Ser Leu Gly
                165                 170                 175

Gly Gln Gln Met Ser Ala Pro Lys Ala Phe Gly Glu Ser Gly Arg Val
            180                 185                 190

Ile Asp Tyr Gly Asp Gln Asn Leu Met Thr Tyr Gly Asp Gly Ser Ala
        195                 200                 205

Asn His Leu His Asn Gly Ile Gly Trp
    210                 215
```

<210> SEQ ID NO 33
<211> LENGTH: 393
<212> TYPE: DNA
<213> ORGANISM: Phaeodactylum tricornutum

<400> SEQUENCE: 33

```
atgtctgcag aaggtgacga aggaaaactt ccgccgggtg aagagtatga agagattcga    60
gaacaggatc ggtatttgcc catcgcaaac attgcgcgaa tcatgaaaaa cactcttcca   120
```

```
gagaatgcca agattgcaaa agactcgaaa gaaactgtgc aggaatgcgt ttcggaattt    180
atttcattta ttacttcaga ggcaagcgat aagtgccttc aagagaagag gaagacaatc    240
aatggggacg atctttatg gcaatgtca accttaggtt ttgataagta tgtggaaccc    300
ctcaagctat atcttagcaa gtatcgcgaa gcggtaaaag gcgaaaaacc tgaaaaaccc    360
ggtcgggtga ctgccatgca agaagactct tag                                393
```

<210> SEQ ID NO 34
<211> LENGTH: 130
<212> TYPE: PRT
<213> ORGANISM: Phaeodactylum tricornutum

<400> SEQUENCE: 34

```
Met Ser Ala Glu Gly Asp Glu Gly Lys Leu Pro Pro Gly Glu Glu Tyr
1               5                   10                  15

Glu Glu Ile Arg Glu Gln Asp Arg Tyr Leu Pro Ile Ala Asn Ile Ala
            20                  25                  30

Arg Ile Met Lys Asn Thr Leu Pro Glu Asn Ala Lys Ile Ala Lys Asp
        35                  40                  45

Ser Lys Glu Thr Val Gln Glu Cys Val Ser Glu Phe Ile Ser Phe Ile
    50                  55                  60

Thr Ser Glu Ala Ser Asp Lys Cys Leu Gln Glu Lys Arg Lys Thr Ile
65                  70                  75                  80

Asn Gly Asp Asp Leu Leu Trp Ala Met Ser Thr Leu Gly Phe Asp Lys
                85                  90                  95

Tyr Val Glu Pro Leu Lys Leu Tyr Leu Ser Lys Tyr Arg Glu Ala Val
            100                 105                 110

Lys Gly Glu Lys Pro Glu Lys Pro Gly Arg Val Thr Ala Met Gln Glu
        115                 120                 125

Asp Ser
    130
```

<210> SEQ ID NO 35
<211> LENGTH: 483
<212> TYPE: DNA
<213> ORGANISM: Volvox carteri

<400> SEQUENCE: 35

```
atgagcggcg acgagggaga cggccgcgat ggaaatagta atgctaggga gcaggaccgg     60
tacctgccta tagctaacat tagcaggatt atgaagaagg ctctgcctgg gaatgctaag   120
atagccaagt atgccaaaga aacagttcaa gaatgtgtct ccgagttcat tagcttcatc   180
acgtcggaag ccagcgataa atgtcagcga gaaaagcgga agaccatcaa cggtgatgac   240
ctcttgtggg cgatgacgac gctggggttt gaggaatatc ttgagcccct gaagctctac   300
ctggccaagt tccgagaggc ggaggctgct gtggcgaagc agcagccaag tagcgctggc   360
gcgggtgcgg aggctaagcg tgaggcagca gcggccgctg cagcagcggc tgcctcctca   420
cagcagcacc aggcggcggc acatcaccta catgctcagg tactcgacac tgatcagaaa   480
taa                                                                 483
```

<210> SEQ ID NO 36
<211> LENGTH: 160
<212> TYPE: PRT
<213> ORGANISM: Volvox carteri

<400> SEQUENCE: 36

```
Met Ser Gly Asp Glu Gly Asp Gly Arg Asp Gly Asn Ser Asn Ala Arg
1               5                   10                  15

Glu Gln Asp Arg Tyr Leu Pro Ile Ala Asn Ile Ser Arg Ile Met Lys
            20                  25                  30

Lys Ala Leu Pro Gly Asn Ala Lys Ile Ala Lys Asp Ala Lys Glu Thr
        35                  40                  45

Val Gln Glu Cys Val Ser Glu Phe Ile Ser Phe Ile Thr Ser Glu Ala
    50                  55                  60

Ser Asp Lys Cys Gln Arg Glu Lys Arg Lys Thr Ile Asn Gly Asp Asp
65                  70                  75                  80

Leu Leu Trp Ala Met Thr Thr Leu Gly Phe Glu Glu Tyr Leu Glu Pro
                85                  90                  95

Leu Lys Leu Tyr Leu Ala Lys Phe Arg Glu Ala Glu Ala Val Ala
                100                 105                 110

Lys Gln Gln Pro Ser Ser Ala Gly Ala Gly Ala Glu Ala Lys Arg Glu
            115                 120                 125

Ala Ala Ala Ala Ala Ala Ala Ala Ser Ser Gln Gln His Gln
        130                 135                 140

Ala Ala Ala His His Leu His Ala Gln Val Leu Asp Thr Asp Gln Lys
145                 150                 155                 160

<210> SEQ ID NO 37
<211> LENGTH: 420
<212> TYPE: DNA
<213> ORGANISM: Micromonas pusilla CCMP1545

<400> SEQUENCE: 37
atgagcgctg aaaaggaacc ggagtacggc ggcggggacg atgacgacga cgagcgcggg    60
gagaacgttc gcgagcagga ccgattcctc ccaatcgcga acatctcgcg gataatgaaa   120
aaagccctac ccgcgaacgc gaagatcgcc aaggacgcga aggagaccgt ccaggagtgc   180
gtctcggagt tcatctcgtt cataaccctc gaggcgtcgg ataagtgcca gcgagagaag   240
cggaagacga tcaacggcga cgacctcctg tgggcgatgt ccacgctagg gttcgaagag   300
tacgtcgaac gcctgaaggt gtacctgcac aagtaccgag agaccgaggg cgagaaggcg   360
gagaagtcga aggcgggcgc taacccgtcc aacgccgcgc aaggggactt gctgtcgtga   420

<210> SEQ ID NO 38
<211> LENGTH: 139
<212> TYPE: PRT
<213> ORGANISM: Micromonas pusilla CCMP1545

<400> SEQUENCE: 38

Met Ser Ala Glu Lys Glu Pro Glu Tyr Gly Gly Gly Asp Asp Asp
1               5                   10                  15

Asp Glu Arg Gly Glu Asn Val Arg Glu Gln Asp Arg Phe Leu Pro Ile
            20                  25                  30

Ala Asn Ile Ser Arg Ile Met Lys Lys Ala Leu Pro Ala Asn Ala Lys
        35                  40                  45

Ile Ala Lys Asp Ala Lys Glu Thr Val Gln Glu Cys Val Ser Glu Phe
    50                  55                  60

Ile Ser Phe Ile Thr Ser Glu Ala Ser Asp Lys Cys Gln Arg Glu Lys
65                  70                  75                  80

Arg Lys Thr Ile Asn Gly Asp Asp Leu Leu Trp Ala Met Ser Thr Leu
                85                  90                  95

Gly Phe Glu Glu Tyr Val Glu Pro Leu Lys Val Tyr Leu His Lys Tyr
```

```
                    100                 105                 110
Arg Glu Thr Glu Gly Glu Lys Ala Glu Lys Ser Lys Ala Gly Ala Asn
        115                 120                 125

Pro Ser Asn Ala Ala Gln Gly Asp Leu Leu Ser
    130                 135

<210> SEQ ID NO 39
<211> LENGTH: 417
<212> TYPE: DNA
<213> ORGANISM: Micromonas sp. RCC299

<400> SEQUENCE: 39
atgagcgatg ccaacgatcc cgatgtcgac gacgacgatg acgacaaggg cggcaacgtt      60
cgcgagcaag atcgtttcct tcctatcgca aacatcagcc gaataatgaa aaaagctttg     120
ccagcaaatg ccaagatagc gaaagacgca aagaaactg ttcaagagtg cgtctccgag      180
ttcatcagct tcatcacaag cgaagctagt gacaagtgtc agcgcgaaaa gcgtaaaaca     240
atcaacggag acgatctgct ctgggcaatg agcacgctcg gattcgaaga atatgttgaa     300
ccgttgaagg tttatctgca caagtaccgg gagacggaag tgaaaaagc cacaagcatc      360 aaacatggtg atgcagcagc gaagaaggct gatgtatctg gaaagcagac ctcttag       417

<210> SEQ ID NO 40
<211> LENGTH: 138
<212> TYPE: PRT
<213> ORGANISM: Micromonas sp. RCC299

<400> SEQUENCE: 40

Met Ser Asp Ala Asn Asp Pro Asp Val Asp Asp Asp Asp Asp Asp Lys
1               5                  10                  15

Gly Gly Asn Val Arg Glu Gln Asp Arg Phe Leu Pro Ile Ala Asn Ile
            20                  25                  30

Ser Arg Ile Met Lys Lys Ala Leu Pro Ala Asn Ala Lys Ile Ala Lys
        35                  40                  45

Asp Ala Lys Glu Thr Val Gln Glu Cys Val Ser Glu Phe Ile Ser Phe
    50                  55                  60

Ile Thr Ser Glu Ala Ser Asp Lys Cys Gln Arg Glu Lys Arg Lys Thr
65                  70                  75                  80

Ile Asn Gly Asp Asp Leu Leu Trp Ala Met Ser Thr Leu Gly Phe Glu
                85                  90                  95

Glu Tyr Val Glu Pro Leu Lys Val Tyr Leu His Lys Tyr Arg Glu Thr
            100                 105                 110

Glu Gly Glu Lys Ala Thr Ser Ile Lys His Gly Asp Ala Ala Ala Lys
        115                 120                 125

Lys Ala Asp Val Ser Gly Lys Gln Thr Ser
    130                 135

<210> SEQ ID NO 41
<211> LENGTH: 522
<212> TYPE: DNA
<213> ORGANISM: Arabidopsis thaliana

<400> SEQUENCE: 41
atggcggagt cgcaggccaa gagtcccgga ggctgtggaa gccatgagag tggtggagat      60
caaagtccca ggtcgttaca tgttcgtgag caagataggt tcttccgat tgctaacata     120 agccgtatca tgaaaagagg tcttcctgct aatgggaaaa tcgctaaaga tgctaaggag     180
```

```
attgtgcagg aatgtgtctc tgaattcatc agtttcgtca ccagcgaagc gagtgataaa      240
tgtcaaagag agaaaaggaa gactattaat ggagatgatt tgctttgggc aatggctact      300
ttaggatttg aagactacat ggaacctctc aaggtttacc tgatgagata tagagagatg      360
gagggtgaca caaagggatc agcaaaaggt ggggatccaa atgcaaagaa agatgggcaa      420
tcaagccaaa atggccagtt ctcgcagctt gctcaccaag gtccttatgg gaactctcaa      480
gctcagcagc atatgatggt tccaatgccg ggaacagact ag                        522
```

```
<210> SEQ ID NO 42
<211> LENGTH: 173
<212> TYPE: PRT
<213> ORGANISM: Arabidopsis thaliana

<400> SEQUENCE: 42
```

Met Ala Glu Ser Gln Ala Lys Ser Pro Gly Gly Cys Gly Ser His Glu
1               5                   10                  15

Ser Gly Gly Asp Gln Ser Pro Arg Ser Leu His Val Arg Glu Gln Asp
            20                  25                  30

Arg Phe Leu Pro Ile Ala Asn Ile Ser Arg Ile Met Lys Arg Gly Leu
        35                  40                  45

Pro Ala Asn Gly Lys Ile Ala Lys Asp Ala Lys Glu Ile Val Gln Glu
    50                  55                  60

Cys Val Ser Glu Phe Ile Ser Phe Val Thr Ser Glu Ala Ser Asp Lys
65                  70                  75                  80

Cys Gln Arg Glu Lys Arg Lys Thr Ile Asn Gly Asp Asp Leu Leu Trp
                85                  90                  95

Ala Met Ala Thr Leu Gly Phe Glu Asp Tyr Met Glu Pro Leu Lys Val
            100                 105                 110

Tyr Leu Met Arg Tyr Arg Glu Met Glu Gly Asp Thr Lys Gly Ser Ala
        115                 120                 125

Lys Gly Gly Asp Pro Asn Ala Lys Lys Asp Gly Gln Ser Ser Gln Asn
    130                 135                 140

Gly Gln Phe Ser Gln Leu Ala His Gln Gly Pro Tyr Gly Asn Ser Gln
145                 150                 155                 160

Ala Gln Gln His Met Met Val Pro Met Pro Gly Thr Asp
                165                 170

```
<210> SEQ ID NO 43
<211> LENGTH: 426
<212> TYPE: DNA
<213> ORGANISM: Arabidopsis lyrata

<400> SEQUENCE: 43
atggcggata cgccttcgag cccggccgga gatggcggag aaagcggcgg ctccgttagg       60
gagcaggatc gataccttcc tatagctaat atcagcagga tcatgaagaa agcgttgcct      120
cctaatggaa agattggtaa agatgctaag gatactgttc aggaatgtgt ttctgagttc      180
atcagcttca tcactagcga ggccagtgat aagtgtcaaa agagagaaag gaaaactgtg      240
aatggtgatg atttgttatg ggcaatggca acattaggat ttgaggatta cctggaacct      300
ctaaagatat atctagcgag gtacagggag ttggagggtg ataataaggg atcaggaaag      360
agcggagatg gatctaatag agatgcaggt ggaggtgttt ctggtgaaga aatgccgagc      420
tggtga                                                                426
```

```
<210> SEQ ID NO 44
```

```
<211> LENGTH: 141
<212> TYPE: PRT
<213> ORGANISM: Arabidopsis lyrata

<400> SEQUENCE: 44

Met Ala Asp Thr Pro Ser Ser Pro Ala Gly Asp Gly Glu Ser Gly
1               5                   10                  15

Gly Ser Val Arg Glu Gln Asp Arg Tyr Leu Pro Ile Ala Asn Ile Ser
            20                  25                  30

Arg Ile Met Lys Lys Ala Leu Pro Pro Asn Gly Lys Ile Gly Lys Asp
        35                  40                  45

Ala Lys Asp Thr Val Gln Glu Cys Val Ser Glu Phe Ile Ser Phe Ile
50                  55                  60

Thr Ser Glu Ala Ser Asp Lys Cys Gln Lys Glu Lys Arg Lys Thr Val
65                  70                  75                  80

Asn Gly Asp Asp Leu Leu Trp Ala Met Ala Thr Leu Gly Phe Glu Asp
                85                  90                  95

Tyr Leu Glu Pro Leu Lys Ile Tyr Leu Ala Arg Tyr Arg Glu Leu Glu
            100                 105                 110

Gly Asp Asn Lys Gly Ser Gly Lys Ser Gly Asp Gly Ser Asn Arg Asp
        115                 120                 125

Ala Gly Gly Gly Val Ser Gly Glu Glu Met Pro Ser Trp
    130                 135                 140

<210> SEQ ID NO 45
<211> LENGTH: 486
<212> TYPE: DNA
<213> ORGANISM: Arabidopsis lyrata

<400> SEQUENCE: 45
atggcggatt cggacaacga ttcaggagga cacaaagacg gtggaaatgc ttcaacacgt      60
gagcaagata ggtttctacc gattgctaac gttagcagga tcatgaagaa agcacttccg     120
gcgaacgcaa aaatctccaa ggacgctaaa gaaacggttc aagagtgtgt atcggaattc     180
ataagtttca tcaccggtga agcttctgac aagtgtcaga gagagaagag gaagacaatc     240
aacggtgacg atcttctttg gcgatgact acgctagggt ttgaggatta cgtggagcct     300
ctaaaggttt atctgcaaaa gtataggag gtggaaggag agaagactac tacggccggg     360
agactaggcg ataaggaagg tggaggagga ggtggtggag ctggaagtgg aagcggagga     420
gctccgatgt acggtggtgg catggtgact acgatggggc atcaattttc ccatcatttt     480
tcttaa                                                                486

<210> SEQ ID NO 46
<211> LENGTH: 161
<212> TYPE: PRT
<213> ORGANISM: Arabidopsis lyrata

<400> SEQUENCE: 46

Met Ala Asp Ser Asp Asn Asp Ser Gly Gly His Lys Asp Gly Gly Asn
1               5                   10                  15

Ala Ser Thr Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60
```

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Val Tyr Leu Gln Lys Tyr Arg Glu Val Glu
            100                 105                 110

Gly Glu Lys Thr Thr Thr Ala Gly Arg Leu Gly Asp Lys Glu Gly Gly
        115                 120                 125

Gly Gly Gly Gly Gly Ala Gly Ser Gly Ser Gly Ala Pro Met Tyr
    130                 135                 140

Gly Gly Gly Met Val Thr Thr Met Gly His Gln Phe Ser His His Phe
145                 150                 155                 160

Ser

<210> SEQ ID NO 47
<211> LENGTH: 717
<212> TYPE: DNA
<213> ORGANISM: Arabidopsis lyrata

<400> SEQUENCE: 47
atggaacgtg gagctcccct ctctcactat cagctaccaa atccatctc tgaattgaac      60 ttggaccagc acagcaacaa cccaacccca atgaccagct cagtcgtagt agccggcgcc    120
ggtgacaaga caatggtat cgtggtccag cagcaaccac catgtgtggc tcgtgagcaa    180
gaccaataca tgccaatcgc aaacgtcata agaatcatgc gtaaaacctt accgtctcac    240
gccaaaatct ctgacgacgc caaagaaacg attcaagaat gtgtctccga gtacatcagc    300
ttcgtgaccg gtgaagccaa cgagcgttgc aacgtgagc aacgtaagac cataactgct    360
gaagatatcc tttgggctat gagcaagctt gggttcgata actacgtgga ccccctcacc    420
gtgttcatta accggtaccg tgagatagag accgatcgtg ttctgcact tagaggtgag    480 ccaccgtcgt tgagacaaac ctatggagga aatggtattg gtttcacgg cccatctcat    540 ggcctacctc ctccgggtcc ttatggttat ggtatgttgg accaatccat ggttatggga    600
ggtggtcggt actaccaaaa cgggtcgtcg ggtcaagatg aatccagtgt tggtggtggc    660
tcttcgtctt ccattaacgg aatgccggct tttgaccatt atggtcagta taagtga       717

<210> SEQ ID NO 48
<211> LENGTH: 238
<212> TYPE: PRT
<213> ORGANISM: Arabidopsis thaliana

<400> SEQUENCE: 48

Met Glu Arg Gly Ala Pro Phe Ser His Tyr Gln Leu Pro Lys Ser Ile
1               5                   10                  15

Ser Glu Leu Asn Leu Asp Gln His Ser Asn Asn Pro Thr Pro Met Thr
            20                  25                  30

Ser Ser Val Val Val Ala Gly Ala Gly Asp Lys Asn Asn Gly Ile Val
        35                  40                  45

Val Gln Gln Gln Pro Pro Cys Val Ala Arg Glu Gln Asp Gln Tyr Met
    50                  55                  60

Pro Ile Ala Asn Val Ile Arg Ile Met Arg Lys Thr Leu Pro Ser His
65                  70                  75                  80

Ala Lys Ile Ser Asp Asp Ala Lys Glu Thr Ile Gln Glu Cys Val Ser
                85                  90                  95

Glu Tyr Ile Ser Phe Val Thr Gly Glu Ala Asn Glu Arg Cys Gln Arg

|  | 100 | | | | 105 | | | | 110 | | | |
|---|---|---|---|---|---|---|---|---|---|---|---|---|
| Glu | Gln | Arg | Lys | Thr | Ile | Thr | Ala | Glu | Asp | Ile | Leu | Trp | Ala | Met | Ser |
|  |  |  | 115 |  |  |  |  | 120 |  |  |  |  | 125 |  |  |

Glu Gln Arg Lys Thr Ile Thr Ala Glu Asp Ile Leu Trp Ala Met Ser
              115                 120                 125

Lys Leu Gly Phe Asp Asn Tyr Val Asp Pro Leu Thr Val Phe Ile Asn
    130                 135                 140

Arg Tyr Arg Glu Ile Glu Thr Asp Arg Gly Ser Ala Leu Arg Gly Glu
145                 150                 155                 160

Pro Pro Ser Leu Arg Gln Thr Tyr Gly Asn Gly Ile Gly Phe His
                165                 170                 175

Gly Pro Ser His Gly Leu Pro Pro Gly Pro Tyr Gly Tyr Gly Met
                180                 185                 190

Leu Asp Gln Ser Met Val Met Gly Gly Arg Tyr Tyr Gln Asn Gly
            195                 200                 205

Ser Ser Gly Gln Asp Glu Ser Ser Val Gly Gly Ser Ser Ser Ser
        210                 215                 220

Ile Asn Gly Met Pro Ala Phe Asp His Tyr Gly Gln Tyr Lys
225                 230                 235

<210> SEQ ID NO 49
<211> LENGTH: 573
<212> TYPE: DNA
<213> ORGANISM: Schizochytrium aggregatum

<400> SEQUENCE: 49

```
cagcaggcaa gcggagcgag cgagcgagcg agcgagcgag ccaggtgcgc gcgggtaggc      60
gactgcggcg gcgcgtcagc ggcagctgcg cgcggcgcgc ggggcgaaac cagaccgtct     120
ccggcagcca gcgcgggctc taggcgcgcg cggcgcaccg cggcccccga cgccaccatg     180
caggatgagg tgcgcgagca ggaccgctac ctgccggttg caaatatcaa ccgcatcatg     240
aagcgctccc tgccagccaa cgccaagatt gccaaggatg ccaaggagac tgtgcaggaa     300
tgcgtgtccg agttcatctc gttcatcacc tctgaggctt ccgacaaggt tcttgccgag     360
aagcggaaga cgatcacggg cgacgacgtg ctctgggcca tgagcaccct cggctttgac     420
aagtatgtgg agcctctcaa gatctacctg acccgctacc gcgagtctgt gaagggcgat     480
aaggcggaga aggggcctgg gccgagcccg atggaaggag ctggtgccgg ctttggcggt     540
gcttcttctt cttccacccc gcctatgcct taa                                  573
```

<210> SEQ ID NO 50
<211> LENGTH: 128
<212> TYPE: PRT
<213> ORGANISM: Schizochytrium aggregatum

<400> SEQUENCE: 50

Met Gln Asp Glu Val Arg Glu Gln Asp Arg Tyr Leu Pro Val Ala Asn
1               5                   10                  15

Ile Asn Arg Ile Met Lys Arg Ser Leu Pro Ala Asn Ala Lys Ile Ala
            20                  25                  30

Lys Asp Ala Lys Glu Thr Val Gln Glu Cys Val Ser Glu Phe Ile Ser
        35                  40                  45

Phe Ile Thr Ser Glu Ala Ser Asp Lys Val Leu Ala Glu Lys Arg Lys
    50                  55                  60

Thr Ile Thr Gly Asp Asp Val Leu Trp Ala Met Ser Thr Leu Gly Phe
65                  70                  75                  80

Asp Lys Tyr Val Glu Pro Leu Lys Ile Tyr Leu Thr Arg Tyr Arg Glu
                85                  90                  95

Ser Val Lys Gly Asp Lys Ala Glu Lys Gly Pro Gly Pro Ser Pro Met
            100                 105                 110

Glu Gly Ala Gly Ala Gly Phe Gly Gly Ala Ser Ser Ser Thr Pro
        115                 120                 125

<210> SEQ ID NO 51
<211> LENGTH: 360
<212> TYPE: DNA
<213> ORGANISM: Aplanochytrium sp.

<400> SEQUENCE: 51
atggctaaac caagcgaagg tgcagaaaag ggaggggaag aggttaggga gcaggatcga      60
taccttccaa tagcaaatat ttcacgaatt atgaagaagt cgctccctca gaatgccaaa    120
atagcaaagg atgcgaagga aactgttcaa gaatgtgtat cagaattcat atcttttatt    180
acaagcgagg ccagtgacaa agtacaaaat gaaaaacgca agacaattac aggtgatgat    240
gtactctggg caatgagtac tcttggattc gaaaaatacg tcgagcctct taagacatat    300
cttggaaagt accgagattc tgttaagggc gagaaaccag agatggcgg agattattga    360

<210> SEQ ID NO 52
<211> LENGTH: 119
<212> TYPE: PRT
<213> ORGANISM: Aplanochytrium sp.

<400> SEQUENCE: 52

Met Ala Lys Pro Ser Glu Gly Ala Glu Lys Gly Gly Glu Glu Val Arg
1               5                   10                  15

Glu Gln Asp Arg Tyr Leu Pro Ile Ala Asn Ile Ser Arg Ile Met Lys
            20                  25                  30

Lys Ser Leu Pro Gln Asn Ala Lys Ile Ala Lys Asp Ala Lys Glu Thr
        35                  40                  45

Val Gln Glu Cys Val Ser Glu Phe Ile Ser Phe Ile Thr Ser Glu Ala
    50                  55                  60

Ser Asp Lys Val Gln Asn Glu Lys Arg Lys Thr Ile Thr Gly Asp Asp
65                  70                  75                  80

Val Leu Trp Ala Met Ser Thr Leu Gly Phe Glu Lys Tyr Val Glu Pro
                85                  90                  95

Leu Lys Thr Tyr Leu Gly Lys Tyr Arg Asp Ser Val Lys Gly Glu Lys
            100                 105                 110

Pro Gly Asp Gly Gly Asp Tyr
        115

<210> SEQ ID NO 53
<211> LENGTH: 923
<212> TYPE: DNA
<213> ORGANISM: Nannochloropsis gaditana

<400> SEQUENCE: 53
aaagttgaaa atgctaacag tgaagtgata tccttttta atggagtgtt gaggtgaagt      60
ctagcatcgt aggggaaaac aggattctgt gtcttccatt ctactccttg ataaagcgaa    120
gaaatccgac aaaaccaaag agattgttca agtttaagat ttgtaagcgt acaactatga    180
acttcttctc tttgtaggcc tgagtggtcg tatgcatacg attcatgaag tgaatcagta    240
tcgctggatt ttgcttagga gtaaagcaca actaagaaaa tatgctgcct ggcaggcatc    300
ctgagacatg aggcaagcga cgtagcaatt gaatcctaat ttaagccagg gcatctgtat    360

```
gactctgtta gttaattgat gaaccaatga gctttaaaaa aaaatcgttg cgcgtaatgt    420
agttttaatt ctccgccttg aggtgcgggg ccatttcgga caaggttctt tggacggaga    480
tggcagcatg tgtcccttct ccaaattggt ccgtgtggta gttgagatgc tgccttaaaa    540
ttctgctcgg tcatcctgcc ttcgcattca ctcctttcga gctgtcgggt tcctcacgag    600
gcctccggga gcggattgcg cagaaaggcg acccggagac acagagacca tacaccgact    660
aaattgcact ggacgatacg gcatggcgac gacgatggcc aagcattgct acgtgattat    720
tcgccttgtc attcagggag aaatgatgac atgtgtggga cggtctttat atgggaagag    780
ggcatgaaaa taacatggcc tggcgggatg gagcgtcaca cctgtgtatg cgttcgatcc    840
acaagcaact caccatttgc gtcggggcct gtctccaatc tgctttaggc tacttttctc    900
taatttagcc tattctatac aga                                            923
```

```
<210> SEQ ID NO 54
<211> LENGTH: 927
<212> TYPE: DNA
<213> ORGANISM: Nannochloropsis gaditana

<400> SEQUENCE: 54
ctactctcca actgagacga aatttatagc gccatctcgc ttctgactac caggcttagg     60
aaggcctcat cacaagctgg atcggttcga attaagcagg cactgaagcc aagcttgcaa    120
gacagccacc ttttaattct ctcaaaacac tttctcaatt cagcccggta aatatgccga    180
ttcacagcgg ccaagataga ggggaggtta gcaagaatgt tgcgatccct ccccagtcgt    240
tgcctcgcac acaacctagg acttcacctt tccatggaaa attgagaagt gaatattggt    300
tttcttacgg catatcagat gaaatcatga cccctaaaca tgaagagctg caggcaaaac    360
acctgctctg gacgagcacg atgaaatctc gagaacccgc cgtacttcag ttgatcccgc    420
atgatgacgg ccgccattga aataagccac ctcactttat tctagcaccg atttccaccg    480
ttgtgagggc cgaacgagga caatttcgtg cgaaacaagc acgaacgcgc acacgattag    540
taggacagac gagcagatcg atggcatgcg gcacggtctc gcgttctcgg cgaccaggac    600
aacggagcag agggaggcct gccgagttcc gaggggcatt ttagtccaaa attgtgttga    660
cacgtgaaca agtggcttga aaagaggaag gaaatgcctg ggtttccctt cgagagcggg    720
aactcgcttg tgcgtcatcc tagctaccca tggtcccttt gtgggggagg ctgtttcgtc    780
ctaccgaatg tgtggcgctc catgcatctt ctgcctccca aaccaccaac atgagcacgc    840
gaaggaagga gaaaaagtg gccgcaacgt tctcttctca tatttattgt ctcatcacaa     900
acataggtac ataatacaac aatcatg                                        927
```

```
<210> SEQ ID NO 55
<211> LENGTH: 1504
<212> TYPE: DNA
<213> ORGANISM: Tetraselmis sp.

<400> SEQUENCE: 55
caccctcacc tctaaggatt actggtaccc caacatccag tagcgccccc ggccagctac     60
ggtgacccaa aaagctagta ctttatctga tagtggaaga actctaccgg atgtatatac    120
agcaggatat tcgtagccct gtcacatgga tgccagcaag acaccggtca ttctgtcatc    180
ttcgtaccat ataatgtcgg cctacgggta ccaagaggcg gtatgtacag gccccccgga    240
cggcgcggat gtcaggcagg cagcaaggat gtgtacgaat gcaccgtgt acatctcgcg    300 ctccatcggt agccgctgct atatagtcgc tagccacttt ttgtcgtccc gccggcatta    360
```

```
tgacatatag cgactacata gcgaccacac cagatatatc tagttgctac gttagagcga    420
cggcacgacg tacaatccta ctactgctgt cgtcgtgtac tgtgccgtgc catgttgctg    480
tgttgcgtct agctcatgta atccatgttg ctgtgtttca gcgcgcgcac accgcgagac    540
cgacgacgct cgcgcgggat ggtcagatta tttttagtac agtacagtga ggcagaaaca    600
catcaaagct tcggccgatg tcccggggcg aactttacat cacagcagaa tcgatttctc    660
aggtcgaatt gtcgtcatat agcgactata taaatgttct taattacatc agggattgca    720
caaatgcgca ctacaaacta tattattgtt cttaaaaata tacaaaaaga tgaaaaaagt    780
atcttcgtcc gcgcattatt accgtatgag caccgtgcg agtccgagcc ctcccggtgc     840
tagtggatcc aggacacgac tagcagtgat tacatgagct agacgcaaca ttcaagaaat    900
ccacacagaa atccagaagg aaataagcag taccagtatt aagtactcct ggtggtaaca    960
ccgactatac tggtctactg ctgacgcgac ctatcacgta tattaacata ttcaataccc   1020
gcatacatgg catatacgac ggataacacc aggtctgtat ctgtaatcaa aattatattc   1080
catatagttg ttcatccttt accggtactg gtagtgaatt acaaaaagga caattctcta   1140
gaattagaaa atcaacacat caagccgcct aaagaaaatc aacacatcct ttaccggtag   1200
agcatacgat gaatatattc gctgttacat ggtttcttgc tgtcggagcg cgcgacggcg   1260
acggcacggc tcatcgggcg tcgtatcgga agtcaggggc gcgcaaaact ccgagagcac   1320
atcagcagca catccgccgg agtattacgc aacatatcct tacagagttg cgcacggtgg   1380
cgtcgtatag tgcatcaaca acatagcaac ccctactttc tggcaaccct tccgagagct   1440
gaggatagtc gcgtcacccc acttccaact tccgtcttcc gtctcaacca ctacacccga   1500
cacc                                                                1504
```

<210> SEQ ID NO 56
<211> LENGTH: 1222
<212> TYPE: DNA
<213> ORGANISM: Tetraselmis sp.

<400> SEQUENCE: 56

```
gaggcctatc ctcgctgctc ataccaccat tcatccacaa atagcagtag ccagcacctg     60
ttgccctctg tgcgcaagtg tgtcagatag gactgcaaat atgaaaacca gccaaattcc    120
tgtactggaa ttggttactc tccactttt tttaggtaga actgtaacca tatcttgcaa     180
aaataccaac aatgcaagga aggagacatt gtgcaggaat acatgctacc taattctggg    240
ggcgacgttc tgaggtttc agttgcggac agcaatgcag cttcaagaca acaatggcat     300
gccttgtccc tttccgcaca tggttatggc atgaatagca agatgttcac tagcgggctg    360
ctgccattca ctgattgttg atgaatgcgc acatttctct gggtagtgga gggtaatttt    420
ggcgttttgg gtattatccg aaatgcctag tttccaacat cgtggatatg ctcttcagtc    480
tcattgtagc atgctgcccg cctgttttga aatgcagtgg gttaaattgg tgcagaagag    540
ggggcagatt ctgtcacatg caactaaaca tcaagggaca atgacaaaat tgtttcccac    600
taggacgata aatccgcact atataatgag acagtgagtg cttttccacc aacctccatg    660
ttgatagaaa tgcaacacc agatcgatgg gcaacattat cggcactcgg ccatgtaggc    720
actcatcgca aatcccggca ctggtggtgc gtgttgggct gccactgtaa gcgcatgccc    780
gctgcagaga ctccactgat gaaggcgctc cagcgaagat ataagcgaaa actgtgcacac   840 agcaacccac cagttgactt cactggcaag aagtaccttc tttgttagca tccagtagac    900
```

```
tgacctcaat atgcactcgc attaattcga ctataacgaa tcatggaact accgaagcat    960
gcaatacgta acatatccgc tgtgtaagta taaatgagcg gtgcgcatgt gctatgatgt   1020
tgcgcagcat agtttatgag ttgttattaa ggaggttgct actgggcttg ccaaatgatt   1080
cagttctgtg agccagatcc ttgagatttg tgtcgcgac gagcacatgt aaacctttaa    1140
aaccgttata tcacttaatt aatgacacag catatgaaac ctagcttaag ttggtaccgt   1200
cgtggacaag tacaagatcg cc                                            1222

<210> SEQ ID NO 57
<211> LENGTH: 378
<212> TYPE: DNA
<213> ORGANISM: Artificial Sequence
<220> FEATURE:
<223> OTHER INFORMATION: Codon optimized Streptoalloteichus hindustanus
      ble gene

<400> SEQUENCE: 57
atgttggcca agctgacgtc ggcggttccg gtcctgacag cgcgtgacgt ggccggagcg     60
gtggagtttt ggactgaccg gctcgggttt agccgggact cgtcgagga cgatttcgct    120 ggcgtagtac gcgatgacgt gaccctcttt atctcggcgg tgcaagacca ggtcgtcccc    180
gacaacacgc tggcttgggt ctgggtgcga ggccttgatg agctgtacgc cgagtggtcc    240
gaggtggttt ccaccaactt ccgcgacgcg agcggtcctg ccatgaccga gattggcgaa    300
cagccgtggg ggagggagtt cgcactccgc gacccagcag gcaattgcgt gcacttcgtc    360
gccgaagagc aggattag                                                  378

<210> SEQ ID NO 58
<211> LENGTH: 716
<212> TYPE: DNA
<213> ORGANISM: Tetraselmis sp.

<400> SEQUENCE: 58
cgtttctgat cctgggcctt ccccgcccgc tgtaccgccg cgcccgcgct cttcgctctt     60
cgctcttcgc gattcagctc gccgccgcca ccgcgaacta gatgcccgcc cctgcagtt    120 agcacaaccg acgcccggct agtattgcat caaccagcca ggtctggcat atggtggtac    180
cacacgtagt cgaagcaggt accccgcgtt tcgagttatc ccctggcccc ctttggtatc    240
ggatcgccgt tggcctctgg gtccagggta acgacgtgcc gcaggttgct gcagcctcgt    300
ttgaaccggc cgagggggc cgcccgcca gttgatgcac ggttcgcgac ccggcgcctc     360
tccgaaatat actgttcccc tctgctagct ttggtagtca ctagataccg tccggcgacg    420 tgccctgtc gggccctggg cgacagccca gcacgtccca gtcaaactcc ggctgaccgg    480
acgctcacac acagctgact gaccctccga cccctctctt tcgggtcaca ccatcccggc    540
ccgcggaccg catagcctgt ggctcctctt ttcgccatat ctcttcttgc gtaatcttgc    600
acgcaattcc ggcgcctctg ccccgtacat cgctcctgtc tgcctttttt gccccactct    660
gaccccctcc tgcatgtgcg ctttgctctc atagagctct tacgaagaaa ggcacc        716

<210> SEQ ID NO 59
<211> LENGTH: 1011
<212> TYPE: DNA
<213> ORGANISM: Tetraselmis sp.

<400> SEQUENCE: 59
agcaagcgct gtgcaatcaa atcaatgctg tctgcgaatg gcgcgtcgtg gcagcggtgc     60
```

```
atgtgccgga gcaaggtttg cgcgcacagg gttggcggtg cacgactgtg gctgttgggc    120
agcaagggg gggtagcaca gtccttgacg cggtgccaag gcggtcctgt ccgtcaggtg    180
agggctgctt ggcctgtgag ctggaggcgc cactgctagc aggacgccca cgatagagta    240
agcgctttct tctggcgcaa catttaatca cacttctgta tctccttttc cctgccagtc    300
tgcttgctgg cgcacttgta ccgtttagtg tggttgtacg ctcgcttcct ccctcagccc    360
gcggcaggag tgctagggaa attcttgcac agagcacaac cgctctcaat gtgacgttga    420
tcggcactct ttcccatgga cagtcaactt ccactggcat tgtttaaatg ctattagcca    480
cttccttaca cgcgaaaaat agcacaagaa ataagcgtcc ctactactca ccgcaccgtc    540
gtgaccatac atcactggtt ccatattgag ctcaggaact cttcagcgcg ttgcccgacg    600
ggagtgccag ggtgcggccg ccatccaaca tgaaactctg cccggtgatg aagccagatg    660
tgctggagga tcccaggaaa ataccgcct cggcaacgtc tgtgggctgc ctgcaatcag    720
aagtgcacag caattgagga tgctgccaaa tggttgatgt gaagtcaggg gagttttgtc    780
atctgcagta tggcacaggg ggggtagatt gagagtctca cccgatgcgg cccagtggat    840
ggcagctagc agactcagcc aggaaggtct cagtgccttc agtcccaagc ccagcacttg    900
ccaaaaagtc ggtctcaatc ctggcggttc acagcagcac atcttgaatg ttacgcgtat    960
gtgatggggc ctggatgggc agggctccaa ccaccaaaca cgaccatttg g             1011

<210> SEQ ID NO 60
<211> LENGTH: 816
<212> TYPE: DNA
<213> ORGANISM: Cyclotella sp.

<400> SEQUENCE: 60
attgttcaag ggccacaatc tgccacaatg aaagctgaag tggaggccaa gcgaatgtag     60
tgacagtttt gacaccatcc ttgaagtaaa aactatagac gtactccaag aagaagaaga    120
acgaatttga ttaagtacgt cacagtgatg tcatcctgaa gtatgcctgg ccatcgtttc    180
cactctccgc gacgttacga cttcgtgtgt cggcatttcg tcagtggttt tgtgctatac    240
atgacatcat ccaaaatcgt cacaaagatc caaaagatat aagagggagg tggagttcgc    300
attggatgta gaggagcttc cataataaaa aaatatatcg atacaagtaa catttttctac    360
aacgactta cgtaagaaaa aaatcgtaat ttcaaatata ttaccaattt tacttttgat    420
atcgcagccc ttgttccccg atatgtatct ttcaacgtgc tgacgtacgc ccctacgagc    480
cgttgatggc cgaaatcttc gtggatgtgt atcgtaaaat tataaaatat gaaagtatgg    540
taggtggtag gtacggtatt gtacgataca tctgtcttgt gatgcgttca ttcgccactg    600
gcgtacttcc atcaaaaact cacccaaagg cccgctcctg ccagccacgg tcgtcttttg    660
tggacgtcaa caaccttcaa tatcgagttc gttgtgattg acgcatcctc tccgaattgg    720
cattgcgttg ttgaacactc ttaactttcg gcatttcctc acgatagtca taaatcaact    780
gcacatcctc gtcgactttg aaaacgacat caaacc                              816

<210> SEQ ID NO 61
<211> LENGTH: 7
<212> TYPE: PRT
<213> ORGANISM: Schizochytrium aggregatum

<400> SEQUENCE: 61

Leu Pro Val Ala Asn Ile Asn
1               5
```

<210> SEQ ID NO 62
<211> LENGTH: 7
<212> TYPE: PRT
<213> ORGANISM: Aplanochytrium sp.

<400> SEQUENCE: 62

Leu Pro Ile Ala Asn Ile Ser
1               5

<210> SEQ ID NO 63
<211> LENGTH: 417
<212> TYPE: DNA
<213> ORGANISM: Nannochloropsis gaditana

<400> SEQUENCE: 63
atgagtggag catcggggaa tgggcaaac cctgctgtac agcaaccta catccccacc      60 gatgctgagc aagcggagca cttacaaaac ttgattagaa aattgaaaga ttttgggta   120 gagcaattgg cagaaatgga gacgttgagt ctcgcatctg aacaggactt caaaaattac   180
attgatctgc ccttggcgcg gatcaaacgc atcatgaaaa gcgacgaaga cgtgcacatg   240
atcagtgcgg aggtgctggt gctctttgca aaggcgtgtg agatgtttat ccttgagctg   300
acgattcgct cctggtgcta cagtgaacga agcaagcgtc gtacgctgca acgggaagac   360
atccaggcag ccattgccaa cgccgacata ttggactttc tcgtaaatat cgtttga      417

<210> SEQ ID NO 64
<211> LENGTH: 138
<212> TYPE: PRT
<213> ORGANISM: Nannochloropsis gaditana

<400> SEQUENCE: 64

Met Ser Gly Ala Ser Gly Asn Gly Ala Asn Pro Ala Val Gln Gln Pro
1               5                   10                  15

Tyr Ile Pro Thr Asp Ala Glu Gln Ala Glu His Leu Gln Asn Leu Ile
                20                  25                  30

Arg Lys Leu Lys Asp Phe Trp Val Glu Gln Leu Ala Glu Met Glu Thr
            35                  40                  45

Leu Ser Leu Ala Ser Glu Gln Asp Phe Lys Asn Tyr Ile Asp Leu Pro
        50                  55                  60

Leu Ala Arg Ile Lys Arg Ile Met Lys Ser Asp Glu Asp Val His Met
65                  70                  75                  80

Ile Ser Ala Glu Val Leu Val Leu Phe Ala Lys Ala Cys Glu Met Phe
                85                  90                  95

Ile Leu Glu Leu Thr Ile Arg Ser Trp Cys Tyr Ser Glu Arg Ser Lys
            100                 105                 110

Arg Arg Thr Leu Gln Arg Glu Asp Ile Gln Ala Ala Ile Ala Asn Ala
        115                 120                 125

Asp Ile Leu Asp Phe Leu Val Asn Ile Val
    130                 135

<210> SEQ ID NO 65
<211> LENGTH: 191
<212> TYPE: PRT
<213> ORGANISM: Thalassiosira oceanica

<400> SEQUENCE: 65

Met Asn Pro Ala Ala Ala Val Ala Thr Ala Thr Arg Ala Ala Thr Ala
1               5                   10                  15

```
Thr Lys Ile Ala Pro Pro Ala Gly Thr Ala Ala Ser Ile Pro Ser Gly
            20                  25                  30

Pro Met Ser Thr Ala Ala Pro Val Ala Pro Met His Ala Thr Met Ala
        35                  40                  45

His Tyr Asn Ile Pro Gly His Leu Pro Pro Gly Met Met Gly Glu Glu
    50                  55                  60

Val Gly Gln Val Met Asp Pro Glu Ser Pro Glu Phe His Ala Gln Leu
65                  70                  75                  80

Ser Glu His Leu Thr Arg Phe Trp Thr Glu Gln Leu Ala Glu Met Gln
                85                  90                  95

Val Leu Gly Thr Asp Lys Arg Gly Thr Glu Gln Asp Phe Lys Asn His
            100                 105                 110

Asn Asp Leu Pro Leu Ala Arg Ile Lys Arg Ile Met Lys Ser Asp Glu
        115                 120                 125

Asp Val Arg Met Ile Ser Ala Glu Ala Pro Val Leu Phe Ala Lys Ala
    130                 135                 140

Cys Glu Met Phe Ile Leu Glu Met Thr Val Arg Gly Trp Asn Tyr Ala
145                 150                 155                 160

Glu Asn Asn Lys Arg Lys Thr Leu Asn Arg Glu Asp Ile Leu Glu Ala
                165                 170                 175

Ile Gln Arg Thr Asn Ile Phe Asp Phe Leu Val Asp Val Ile Asn
            180                 185                 190

<210> SEQ ID NO 66
<211> LENGTH: 125
<212> TYPE: PRT
<213> ORGANISM: Thalassiosira pseudonana

<400> SEQUENCE: 66

Val Phe Asp Pro Glu Gly Pro Gln Phe Leu Gly Pro Leu Asn Asp Ala
1               5                   10                  15

Leu Thr Glu Phe Trp Ala Gly Gln Leu Gln Glu Met Arg Ala Leu Gly
            20                  25                  30

Glu Asp Gln Val Gln Asn Glu Gln Asp Phe Lys Asn His Asn Asp Leu
        35                  40                  45

Pro Leu Ala Arg Ile Lys Arg Ile Met Lys Ser Asp Glu Asp Val Arg
    50                  55                  60

Met Ile Ser Ala Glu Ala Pro Val Leu Phe Ala Lys Ala Cys Glu Met
65                  70                  75                  80

Phe Ile Leu Glu Met Ser Leu Arg Ser Phe His Tyr Ser Glu Asn Asn
                85                  90                  95

Lys Arg Lys Thr Leu Gln Lys Glu Asp Val Ile Glu Ala Ile Gln Arg
            100                 105                 110

Thr Asp Ile Phe Asp Phe Leu Val Asp Val Ile Ser Pro
        115                 120                 125

<210> SEQ ID NO 67
<211> LENGTH: 600
<212> TYPE: DNA
<213> ORGANISM: Nannochloropsis gaditana

<400> SEQUENCE: 67
atgcgtcttt acaggcaaat aaaaaaggca tcaatgtcgc gctcaccaga agtcctgcaa      60
acgtcgaact cagccctgtc ttatgcttca ccttcgcaag caccttcagg ggcggcaatc    120
atgatgccta ctgctccggc attgcccgga agatcaacga cacccccaaa tacgcagaca    180
```

-continued

```
ggcaccgagg agcgcaagcg tgacacacct gaagggccaa aaccttcccc gcttgcaggc    240
acgcccgcat ctatgaaagc agaggaggca cctgtttcgt cgaagaaagc aaggaatgct    300
ccgattccac cactatcaac atcgaatgct acgtgacag  aggacaccac gctggcaata    360
ccaagggcgt caataaagcg aattatgaag ctcgatccgg acacaaagca attgtcccaa    420
gatgctatta tggtgatggc aaaagccaca gagttgttca tcgacaagct agcgaaggcc    480
tcgcattcga tggccgtcac caacaaacga aaaacaataa agtacgagga cattgccgat    540
gcgcgctttt ctcagaaaaa catggagttc ttggacggtg tggttcctca aattccatag    600
```

<210> SEQ ID NO 68
<211> LENGTH: 199
<212> TYPE: PRT
<213> ORGANISM: Nannochloropsis gaditana

<400> SEQUENCE: 68

```
Met Arg Leu Tyr Arg Gln Ile Lys Lys Ala Ser Met Ser Arg Ser Pro
 1               5                  10                  15

Glu Val Leu Gln Thr Ser Asn Ser Ala Leu Ser Tyr Ala Ser Pro Ser
            20                  25                  30

Gln Ala Pro Ser Gly Ala Ala Ile Met Met Pro Thr Ala Pro Ala Leu
        35                  40                  45

Pro Gly Arg Ser Thr Asn Thr Pro Asn Thr Gln Thr Gly Thr Glu Glu
    50                  55                  60

Arg Lys Arg Asp Thr Pro Glu Gly Pro Lys Pro Ser Pro Leu Ala Gly
65                  70                  75                  80

Thr Pro Ala Ser Met Lys Ala Glu Glu Ala Pro Val Ser Ser Lys Lys
                85                  90                  95

Ala Arg Asn Ala Pro Ile Pro Pro Leu Ser Thr Ser Asn Ala Tyr Val
            100                 105                 110

Thr Glu Asp Thr Thr Leu Ala Ile Pro Arg Ala Ser Ile Lys Arg Ile
        115                 120                 125

Met Lys Leu Asp Pro Asp Thr Lys Gln Leu Ser Gln Asp Ala Ile Met
    130                 135                 140

Val Met Ala Lys Ala Thr Glu Leu Phe Ile Asp Lys Leu Ala Lys Ala
145                 150                 155                 160

Ser His Ser Met Ala Val Thr Asn Lys Arg Lys Thr Ile Lys Tyr Glu
                165                 170                 175

Asp Ile Ala Asp Ala Arg Phe Ser Gln Lys Asn Met Glu Phe Leu Asp
            180                 185                 190

Gly Val Val Pro Gln Ile Pro
        195
```

<210> SEQ ID NO 69
<211> LENGTH: 864
<212> TYPE: DNA
<213> ORGANISM: Nannochloropsis gaditana

<400> SEQUENCE: 69

```
atggatggag ctgagacggg gagcggtggc gactcggact caggaggagg acgcaagaag    60
attgtccgcc cttgtagctc agcggagacg tcactttcca tggatgtgac cgctacttct    120
taccagggca caaattttaa tcatatgctc tcgcacggag ctccagcgtc ggcaatggtt    180
gaaacacacg atggcgaggg cagcctttgt ccttttccgt ttcaaccgcc gccacaccag    240
cagcataatc tacaatacca caaccacag  gagcaccaaa tgcagcaaac gtattatggt    300
```

```
caaatgaatg acgatgggaa caattttac gatcactcgc cacatatgga aggtttcgag    360
cccttgggtg ctccccaaga agcggcaggc tcagacctgg gacctcaacc aatattcgtg    420
aaccccaagc aatacgaacg catcatgaaa cgtcgcgagg cgcgggcccg cttggaaaac    480
catcgaaaaa tcgcagccga gcggaagcca tttttgcata aatccaggca cttgcacgct    540
gtcaaaaggc cgcgtggacc cggaggtcgt ttttgacca aggaggaacg aatcgcatgg    600
gatgaggagc aggctcagtt ggaagggacc tccacgatgg gagctgtcca tgtttctaat    660
gaggtcgcgg caaagacctt gtattcgtcg gcgcaagcct ctatagctgc cgggcctcca    720
ttggcttcgc aacaggggtc cagacacgcg tccccgcctt ctcttctcc gctctcttcc    780
tcctcctgcc ttcctccctc cgcctccaca cctgtagctc cctccggccc ttcttcttat    840
tgctcatcct cgcctatcat ctag                                           864
```

```
<210> SEQ ID NO 70
<211> LENGTH: 287
<212> TYPE: PRT
<213> ORGANISM: Nannochloropsis gaditana

<400> SEQUENCE: 70

Met Asp Gly Ala Glu Thr Gly Ser Gly Gly Asp Ser Asp Ser Gly Gly
1               5                   10                  15

Gly Arg Lys Lys Ile Val Arg Pro Cys Ser Ser Ala Glu Thr Ser Leu
            20                  25                  30

Ser Met Asp Val Thr Ala Thr Ser Tyr Gln Gly Thr Asn Phe Asn His
        35                  40                  45

Met Leu Ser His Gly Ala Pro Ala Ser Ala Met Val Glu Thr His Asp
    50                  55                  60

Gly Glu Gly Ser Leu Cys Pro Phe Pro Phe Gln Pro Pro His Gln
65                  70                  75                  80

Gln His Asn Leu Gln Tyr Gln Gln Pro Gln Glu His Gln Met Gln Gln
                85                  90                  95

Thr Tyr Tyr Gly Gln Met Asn Asp Asp Gly Asn Asn Phe Tyr Asp His
            100                 105                 110

Ser Pro His Met Glu Gly Phe Glu Pro Leu Gly Ala Pro Gln Glu Ala
        115                 120                 125

Ala Gly Ser Asp Leu Gly Pro Gln Pro Ile Phe Val Asn Pro Lys Gln
    130                 135                 140

Tyr Glu Arg Ile Met Lys Arg Arg Glu Ala Arg Ala Arg Leu Glu Asn
145                 150                 155                 160

His Arg Lys Ile Ala Ala Glu Arg Lys Pro Phe Leu His Lys Ser Arg
                165                 170                 175

His Leu His Ala Val Lys Arg Pro Arg Gly Pro Gly Gly Arg Phe Leu
            180                 185                 190

Thr Lys Glu Glu Arg Ile Ala Trp Asp Glu Glu Gln Ala Gln Leu Glu
        195                 200                 205

Gly Thr Ser Thr Met Gly Ala Val His Val Ser Asn Glu Val Ala Ala
    210                 215                 220

Lys Thr Leu Tyr Ser Ser Ala Gln Ala Ser Ile Ala Ala Gly Pro Pro
225                 230                 235                 240

Leu Ala Ser Gln Gln Gly Ser Arg His Ala Ser Pro Pro Phe Ser Ser
                245                 250                 255

Pro Leu Ser Ser Ser Ser Cys Leu Pro Pro Ser Ala Ser Thr Pro Val
            260                 265                 270
```

Ala Pro Ser Gly Pro Ser Ser Tyr Cys Ser Ser Ser Pro Ile Ile
        275                 280                 285

<210> SEQ ID NO 71
<211> LENGTH: 51
<212> TYPE: DNA
<213> ORGANISM: Artificial Sequence
<220> FEATURE:
<223> OTHER INFORMATION: 5' Primer MCA-1185

<400> SEQUENCE: 71
ttccacccaa gcagtggtat caacgcagag tggcctaagg gaaaacaaca g         51

<210> SEQ ID NO 72
<211> LENGTH: 60
<212> TYPE: DNA
<213> ORGANISM: Artificial Sequence
<220> FEATURE:
<223> OTHER INFORMATION: 3' cDNA cloning primer

<400> SEQUENCE: 72
gtatcgatgc ccaccctcta gaggccgagg cggccgacac ggtacccgct tttttttttt   60

<210> SEQ ID NO 73
<211> LENGTH: 39
<212> TYPE: DNA
<213> ORGANISM: Artificial Sequence
<220> FEATURE:
<223> OTHER INFORMATION: Forward primer JLS-pGAD-1257F

<400> SEQUENCE: 73
ggaggccagt gaattcatgg atggagctga gacggggag                        39

<210> SEQ ID NO 74
<211> LENGTH: 38
<212> TYPE: DNA
<213> ORGANISM: Artificial Sequence
<220> FEATURE:
<223> OTHER INFORMATION: Reverse primer JLS-pGAD-1257R

<400> SEQUENCE: 74
cgagctcgat ggatccctag atgataggcg aggatgag                         38

<210> SEQ ID NO 75
<211> LENGTH: 40
<212> TYPE: DNA
<213> ORGANISM: Artificial Sequence
<220> FEATURE:
<223> OTHER INFORMATION: Forward primer JLC-pGBK-T7-Hap-1742-F

<400> SEQUENCE: 75
catggaggcc gaattcatgg atgaggcggg agccaacgag                       40

<210> SEQ ID NO 76
<211> LENGTH: 40
<212> TYPE: DNA
<213> ORGANISM: Artificial Sequence
<220> FEATURE:
<223> OTHER INFORMATION: Reverse primer JLC-pGBK-T7-Hap-1742-R

<400> SEQUENCE: 76
catggaggcc gaattcatgg atgaggcggg agccaacgag                       40